(12) United States Patent
Takemoto et al.

(10) Patent No.: US 8,351,574 B2
(45) Date of Patent: Jan. 8, 2013

(54) X-RAY DIAGNOSIS APPARATUS FOR CREATING A DISPLAY IMAGE FROM THREE-DIMENSIONAL MEDICAL IMAGE DATA

(75) Inventors: Hisato Takemoto, Nasushiobara (JP); Hajime Yoshida, Nasushiobara (JP); Satoru Ohishi, Otawara (JP)

(73) Assignees: Kabushiki Kaisha Toshiba, Tokyo (JP); Toshiba Medical Systems Corporation, Otaware-shi (JP)

( * ) Notice: Subject to any disclaimer, the term of this patent is extended or adjusted under 35 U.S.C. 154(b) by 257 days.

(21) Appl. No.: 12/707,882

(22) Filed: Feb. 18, 2010

(65) Prior Publication Data
US 2010/0215149 A1  Aug. 26, 2010

(30) Foreign Application Priority Data

Feb. 23, 2009 (JP) ................................. 2009-039869
Feb. 4, 2010  (JP) ................................. 2010-023363

(51) Int. Cl.
*A61B 6/03* (2006.01)
(52) U.S. Cl. ............................... 378/98; 378/4; 382/131
(58) Field of Classification Search .................... 378/20, 378/42, 65, 205, 4, 98; 382/131
See application file for complete search history.

(56) References Cited

U.S. PATENT DOCUMENTS

| | | | | |
|---|---|---|---|---|
| 5,278,887 A * | 1/1994 | Chiu et al. | | 378/156 |
| 5,901,199 A * | 5/1999 | Murphy et al. | | 378/65 |
| 6,516,046 B1 * | 2/2003 | Frohlich et al. | | 378/65 |
| 6,714,810 B2 * | 3/2004 | Grzeszczuk et al. | | 600/427 |
| 7,187,792 B2 * | 3/2007 | Fu et al. | | 382/128 |
| 7,204,640 B2 * | 4/2007 | Fu et al. | | 378/205 |
| 7,231,076 B2 * | 6/2007 | Fu et al. | | 382/131 |
| 7,260,426 B2 * | 8/2007 | Schweikard et al. | | 600/407 |
| 7,327,865 B2 * | 2/2008 | Fu et al. | | 382/128 |
| 7,330,578 B2 * | 2/2008 | Wang et al. | | 382/131 |
| 7,359,541 B2 * | 4/2008 | Kawano | | 382/132 |
| 7,366,278 B2 * | 4/2008 | Fu et al. | | 378/4 |
| 7,426,318 B2 * | 9/2008 | Fu et al. | | 382/294 |

(Continued)

FOREIGN PATENT DOCUMENTS

JP  2001-204718  7/2001

(Continued)

OTHER PUBLICATIONS

Office Action issued Nov. 25, 2011, in Chinese Patent Application No. 201010118882.3.

*Primary Examiner* — Allen C. Ho
(74) *Attorney, Agent, or Firm* — Oblon, Spivak, McClelland, Maier & Neustadt, L.L.P.

(57) ABSTRACT

An X-ray diagnosis apparatus includes a display-image creating unit that creates a display image from three-dimensional medical image data such that a display image of three-dimensional medical image data substantially matches up with an anatomical structure on an acquired image by the X-ray diagnosis apparatus. Moreover, the X-ray diagnosis apparatus includes a display-image changing unit that changes a display image so as to maintain consistency of an anatomical structure in accordance with change in acquiring conditions by the X-ray diagnosis apparatus. Furthermore, the X-ray diagnosis apparatus includes a display unit that displays a display image that is at least one of created and changed by at least one of the display-image creating unit and the display-image changing unit.

23 Claims, 28 Drawing Sheets

U.S. PATENT DOCUMENTS

| | | | |
|---|---|---|---|
| 7,453,984 B2 * | 11/2008 | Chen et al. | 378/65 |
| 7,522,779 B2 * | 4/2009 | Fu et al. | 382/254 |
| 7,623,623 B2 * | 11/2009 | Raanes et al. | 378/65 |
| 7,672,429 B2 * | 3/2010 | Urano et al. | 378/65 |
| 7,684,647 B2 * | 3/2010 | Fu et al. | 382/294 |
| 7,756,567 B2 * | 7/2010 | Kuduvalli et al. | 600/427 |
| 7,831,073 B2 * | 11/2010 | Fu et al. | 382/128 |
| 7,835,500 B2 * | 11/2010 | Fu et al. | 378/128 |
| 7,889,902 B2 * | 2/2011 | Zhang et al. | 382/128 |
| 7,894,649 B2 * | 2/2011 | Fu et al. | 382/128 |
| 7,940,999 B2 * | 5/2011 | Liao et al. | 382/294 |
| 8,009,885 B2 * | 8/2011 | Grass et al. | 382/128 |
| 8,126,236 B2 * | 2/2012 | Harer et al. | 382/130 |
| 2006/0181551 A1 | 8/2006 | Matsumoto | |

FOREIGN PATENT DOCUMENTS

| | | |
|---|---|---|
| JP | 2002-136507 | 5/2002 |
| JP | 2006-187531 | 7/2006 |
| WO | WO 2009/019640 A2 | 2/2009 |

* cited by examiner

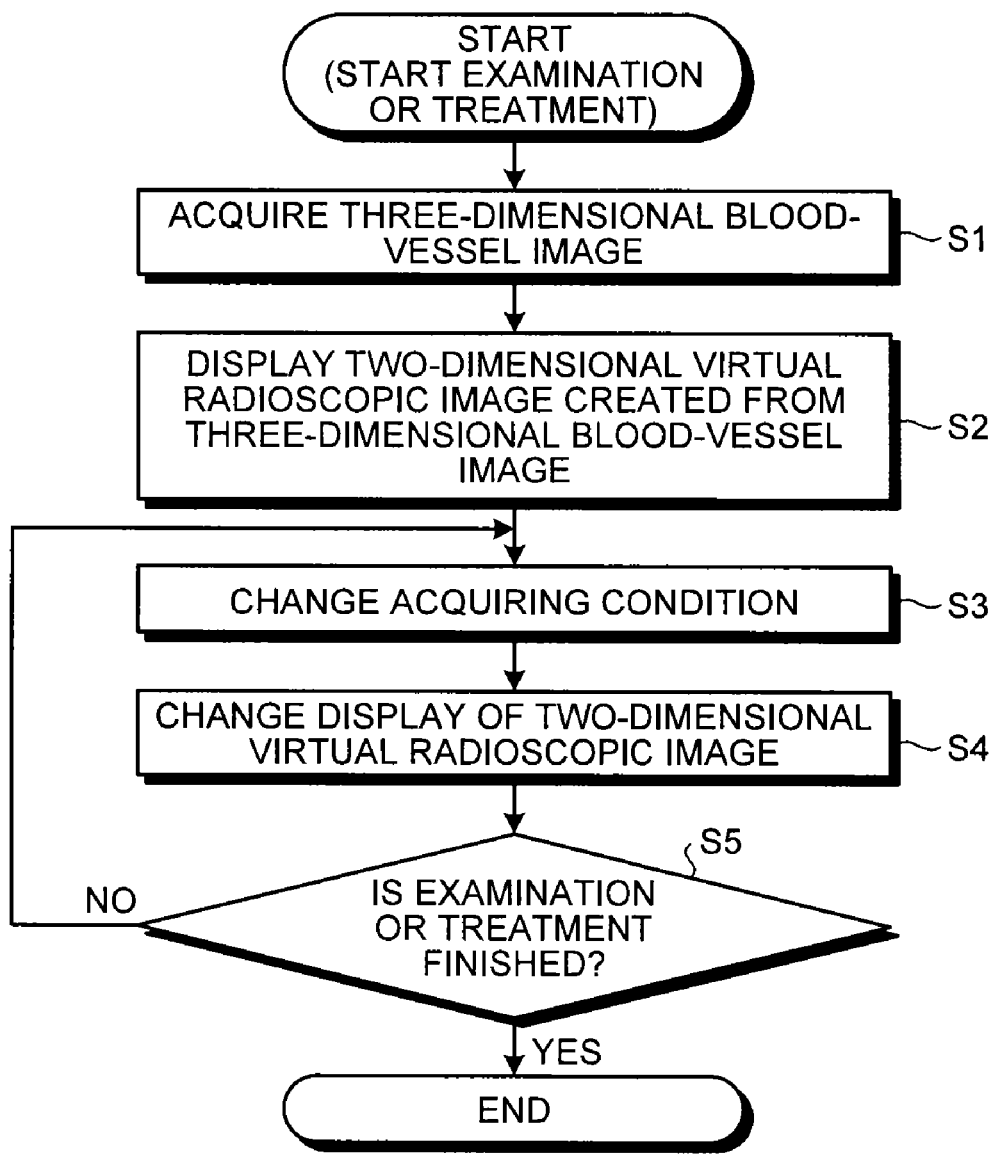

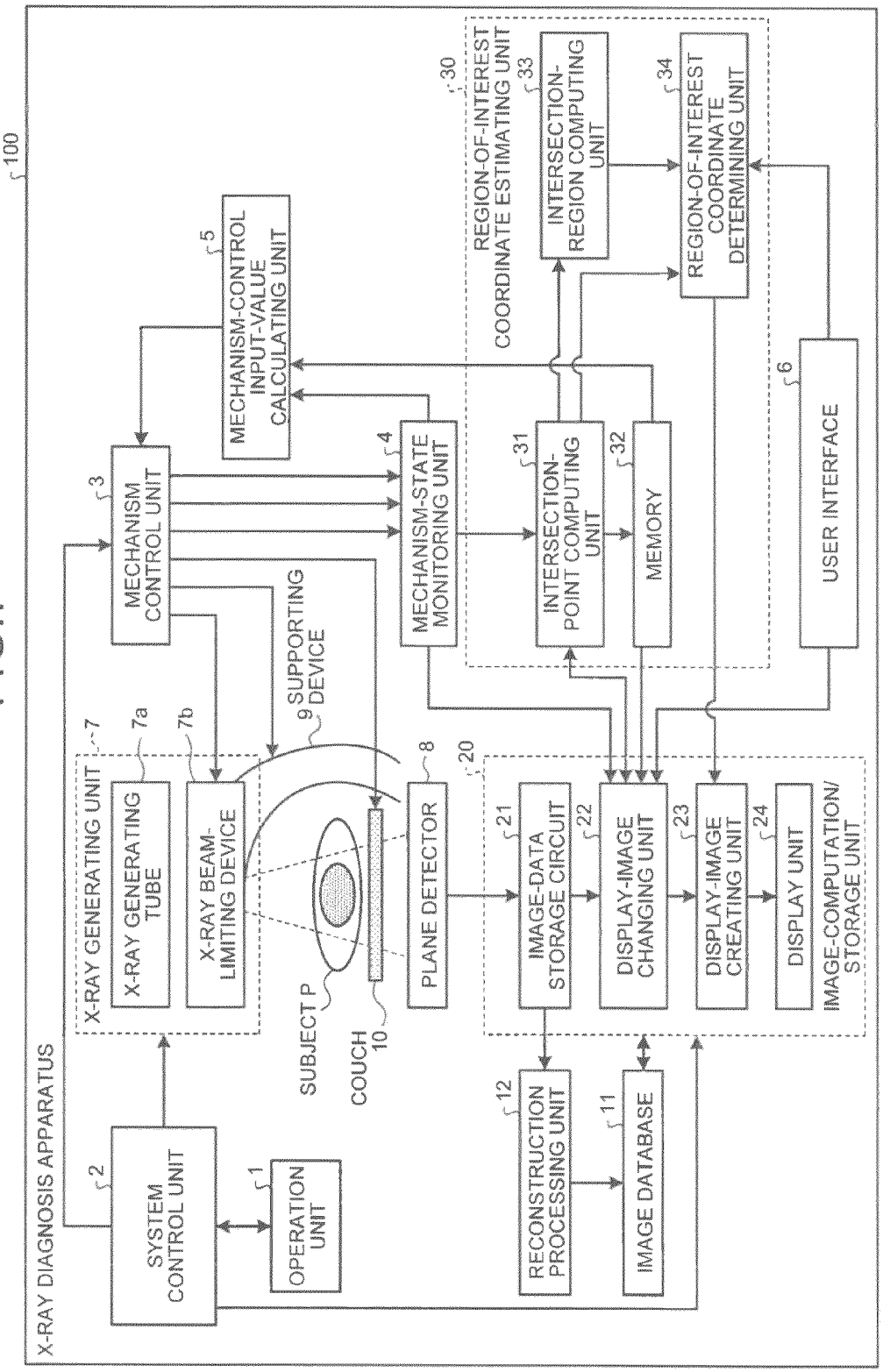

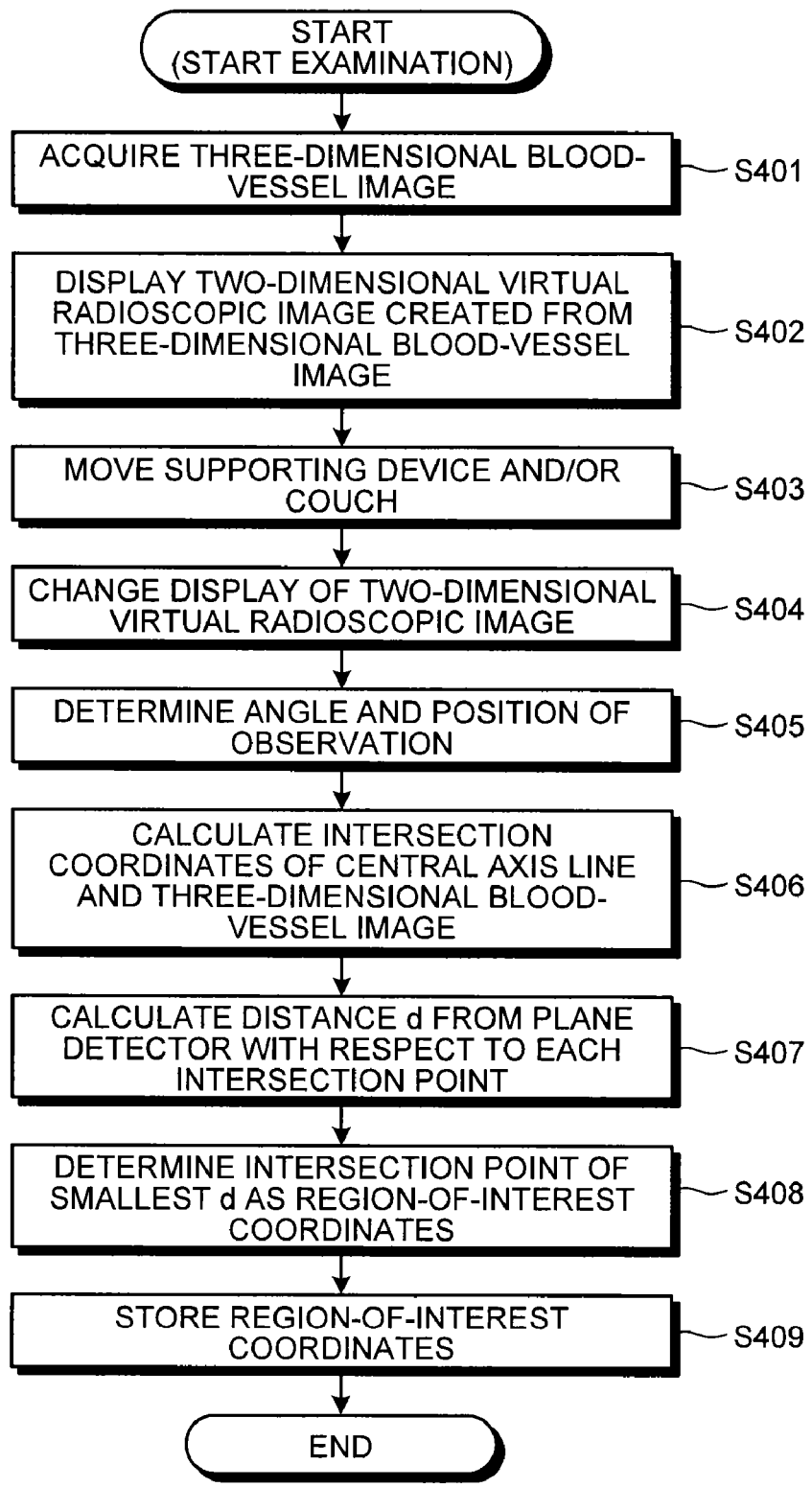

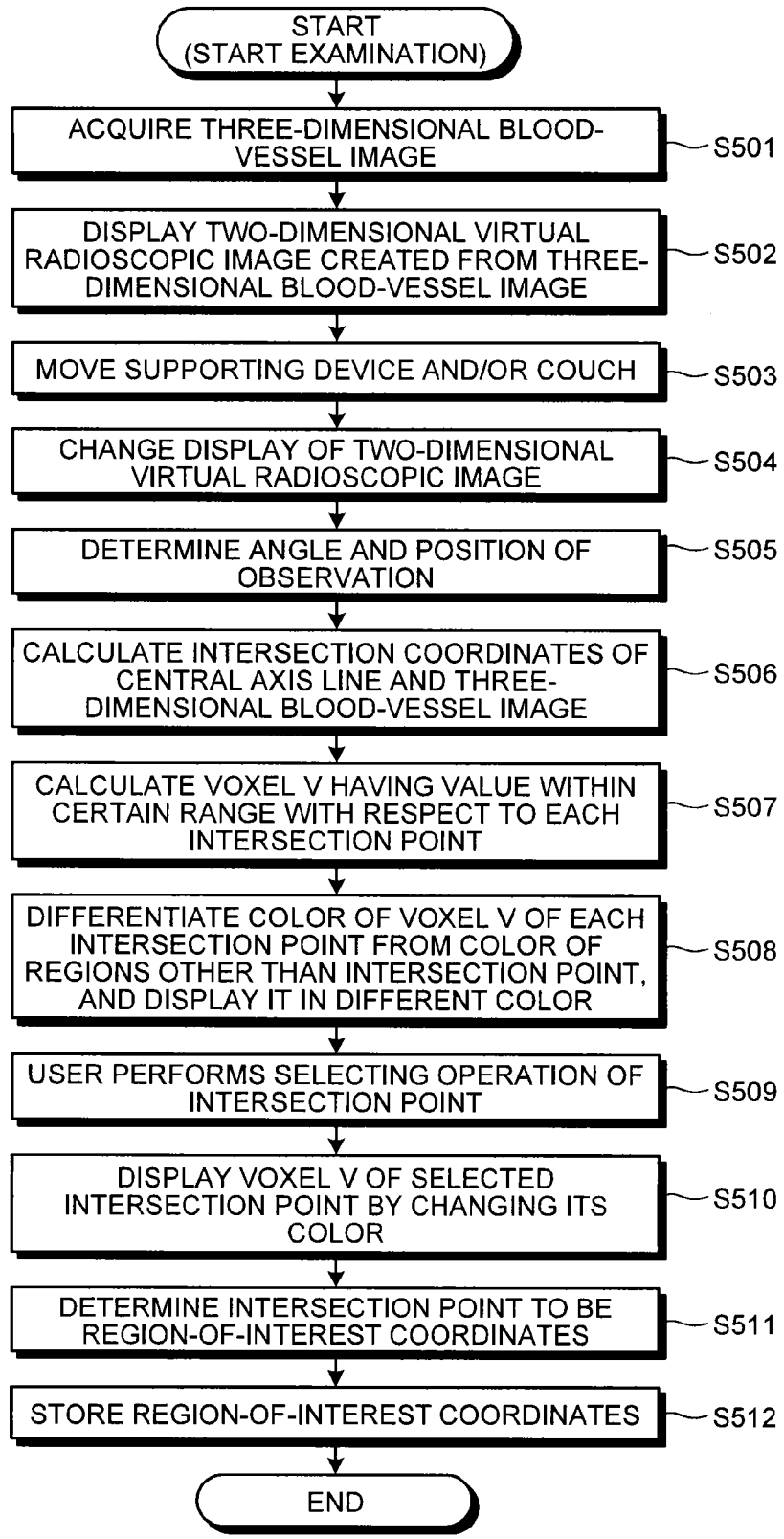

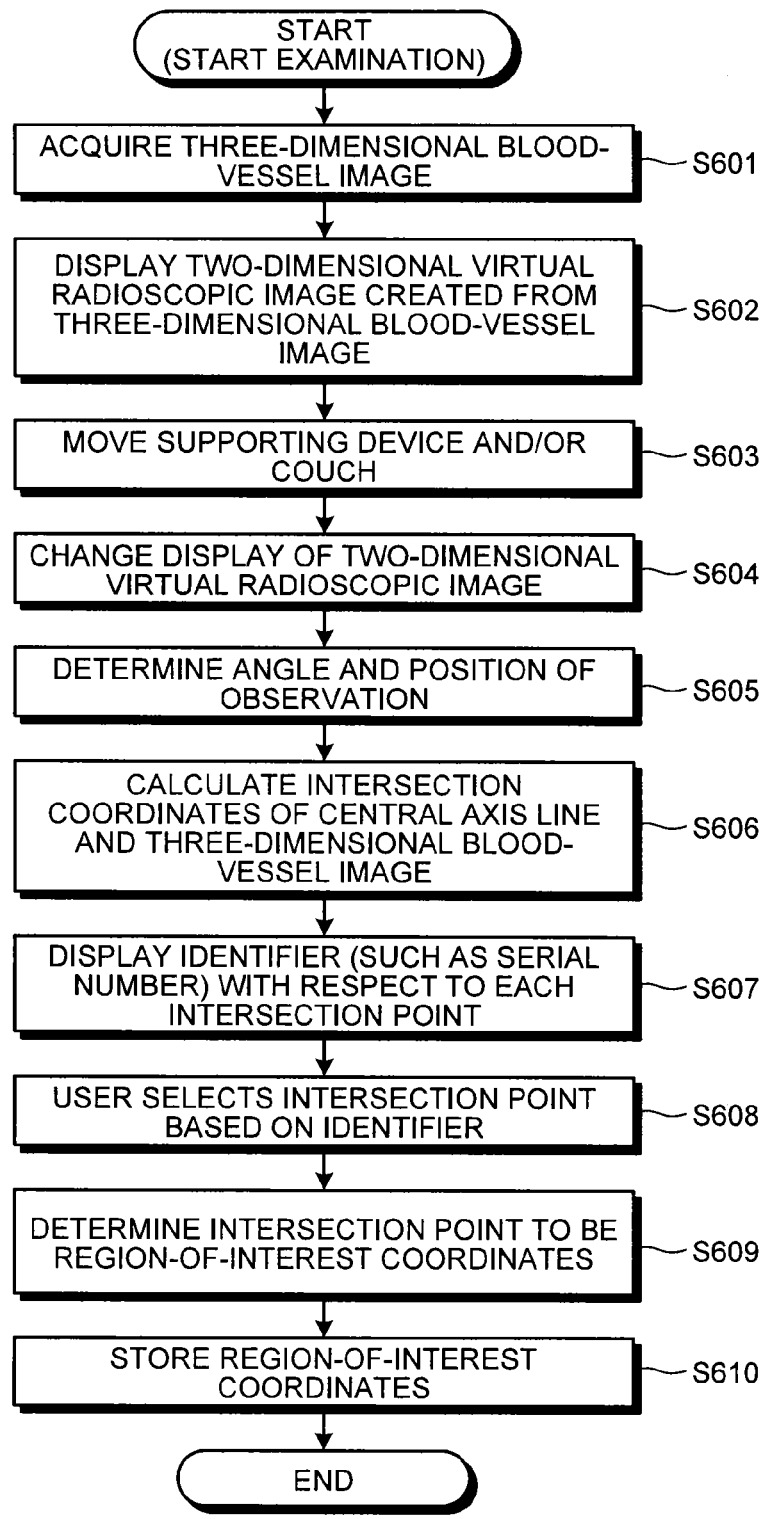

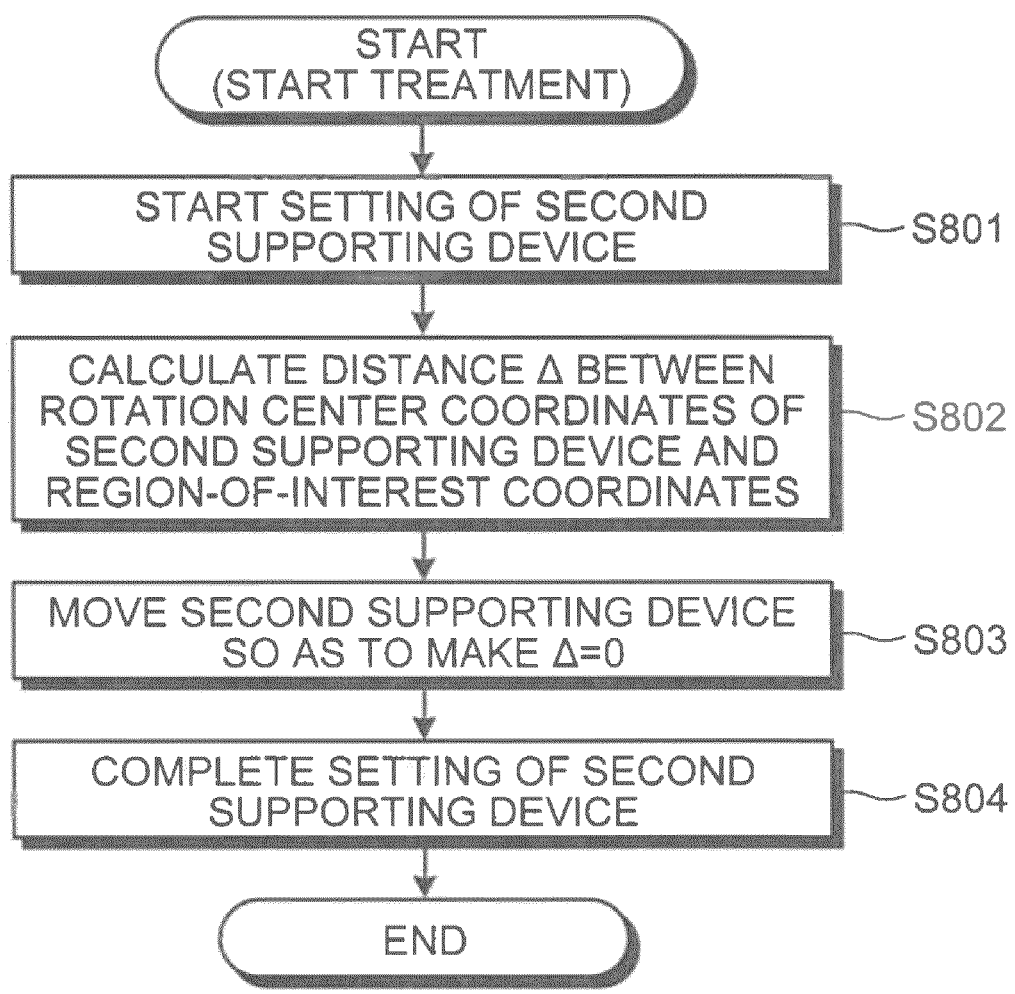

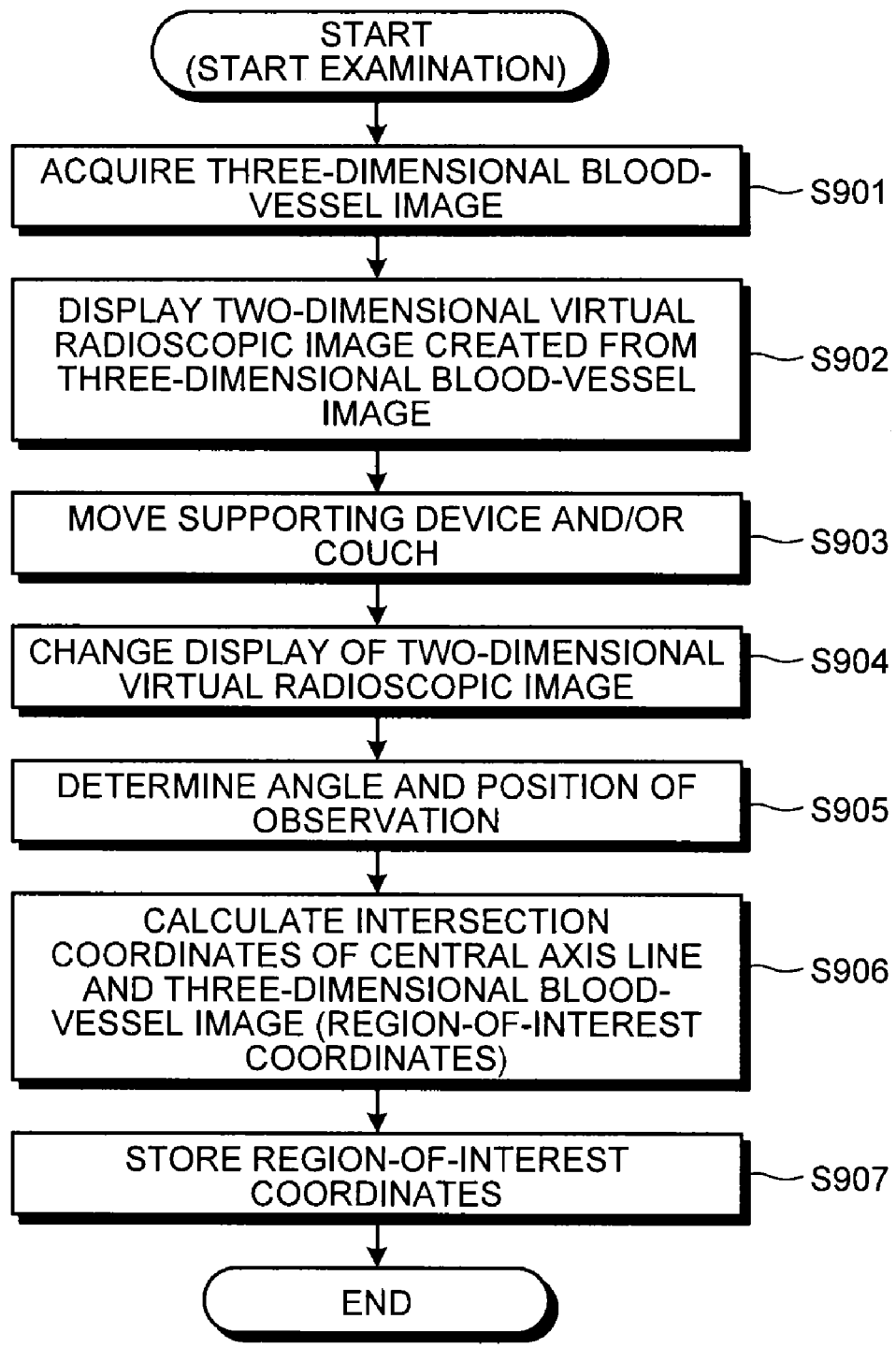

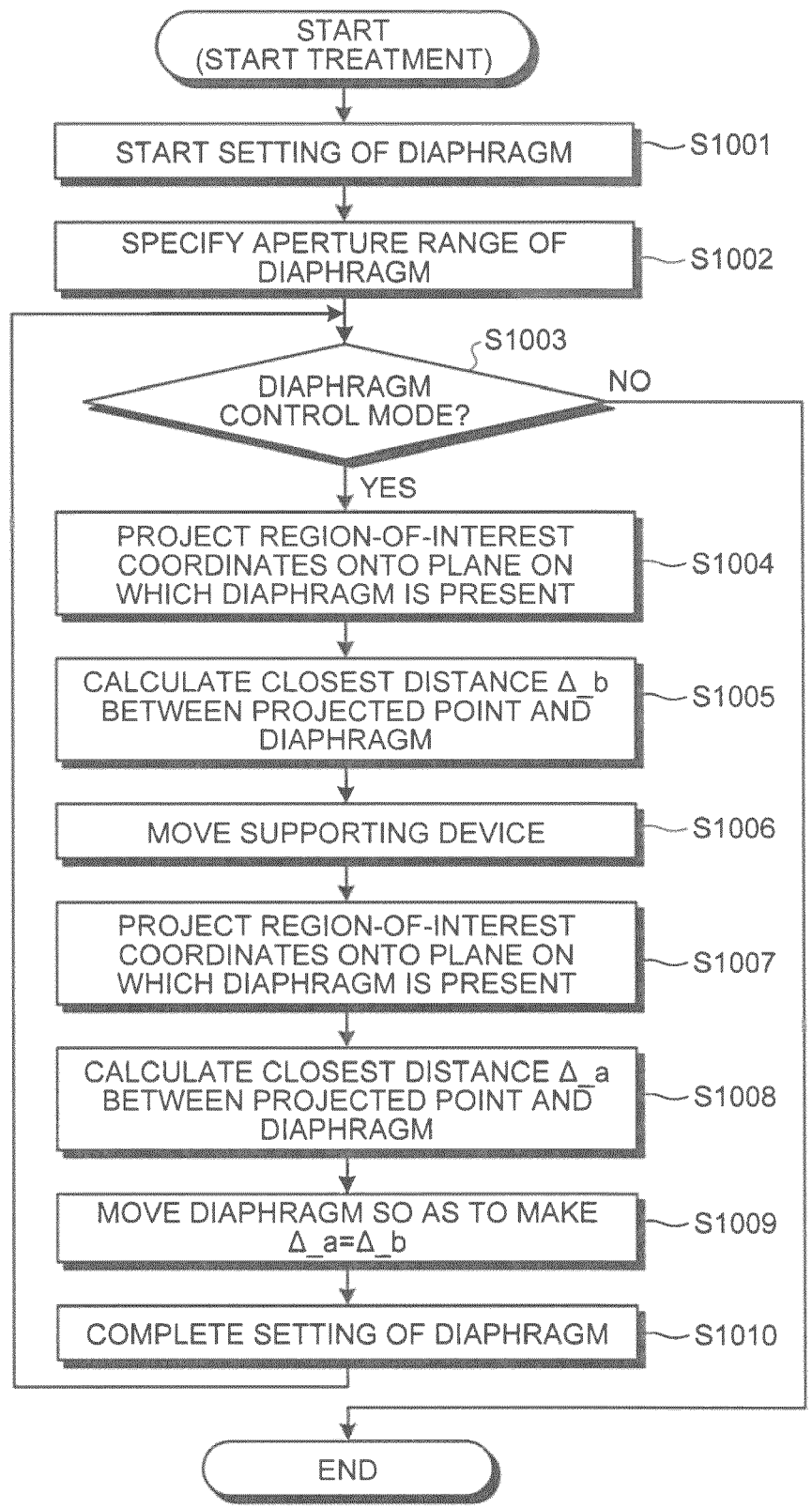

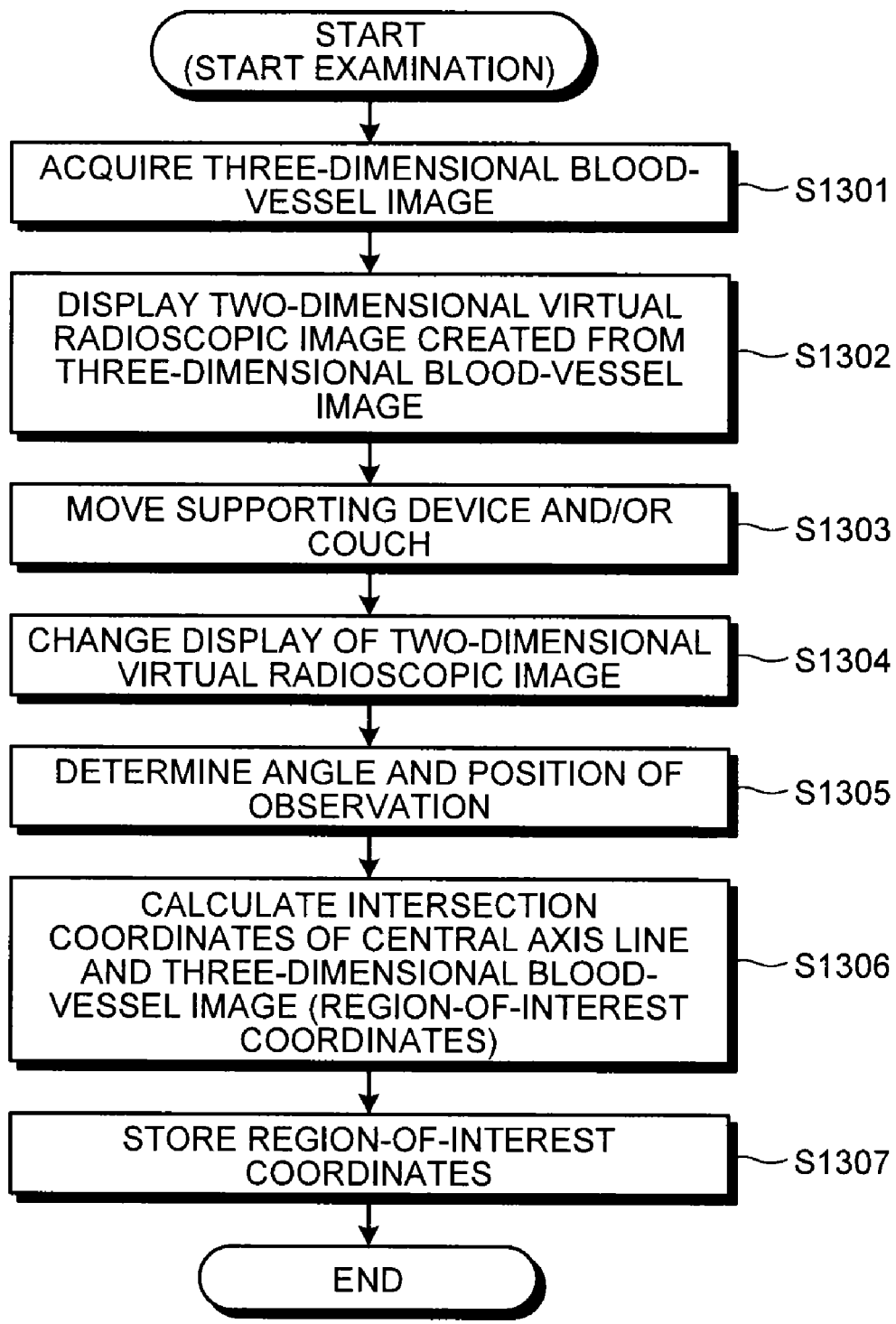

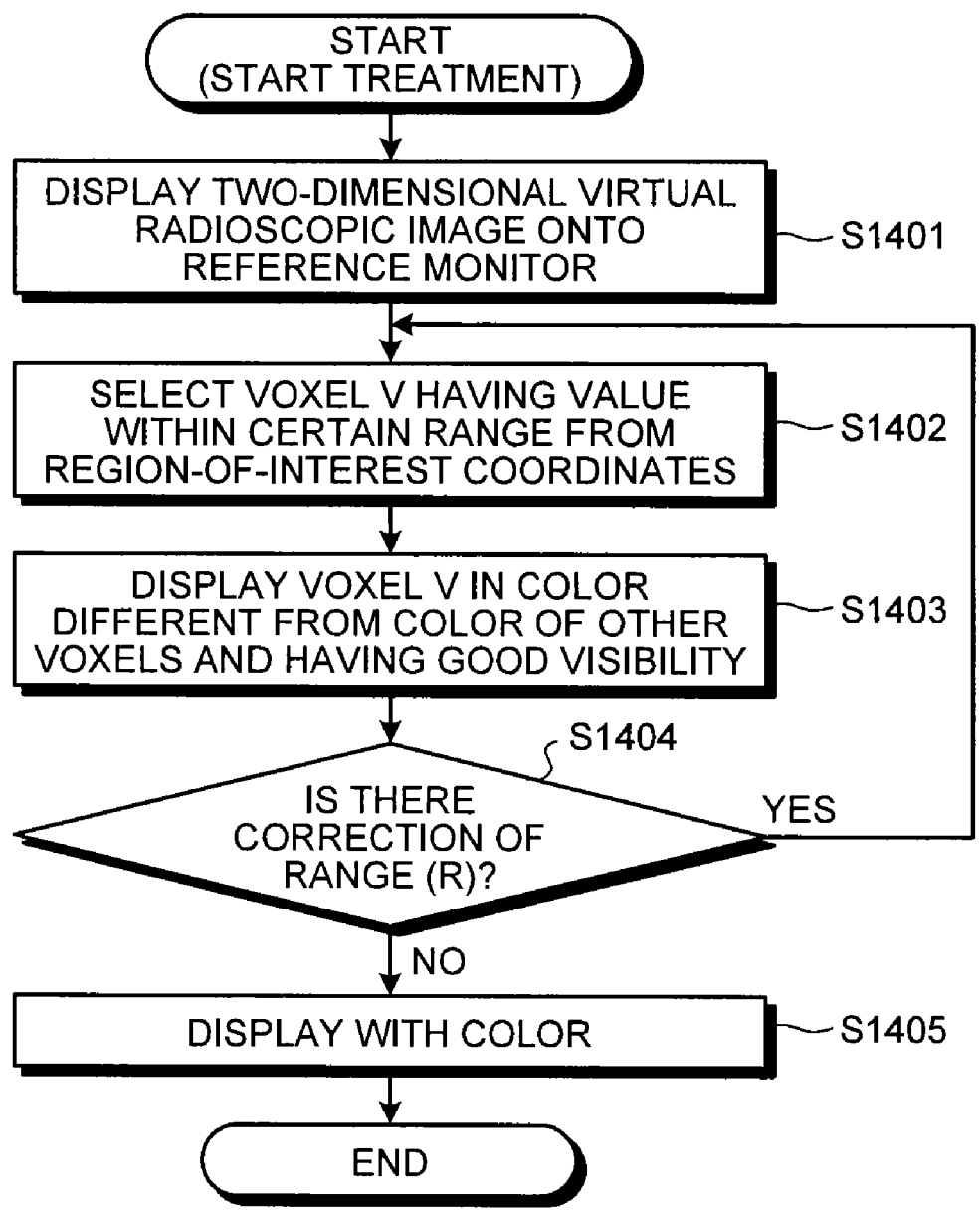

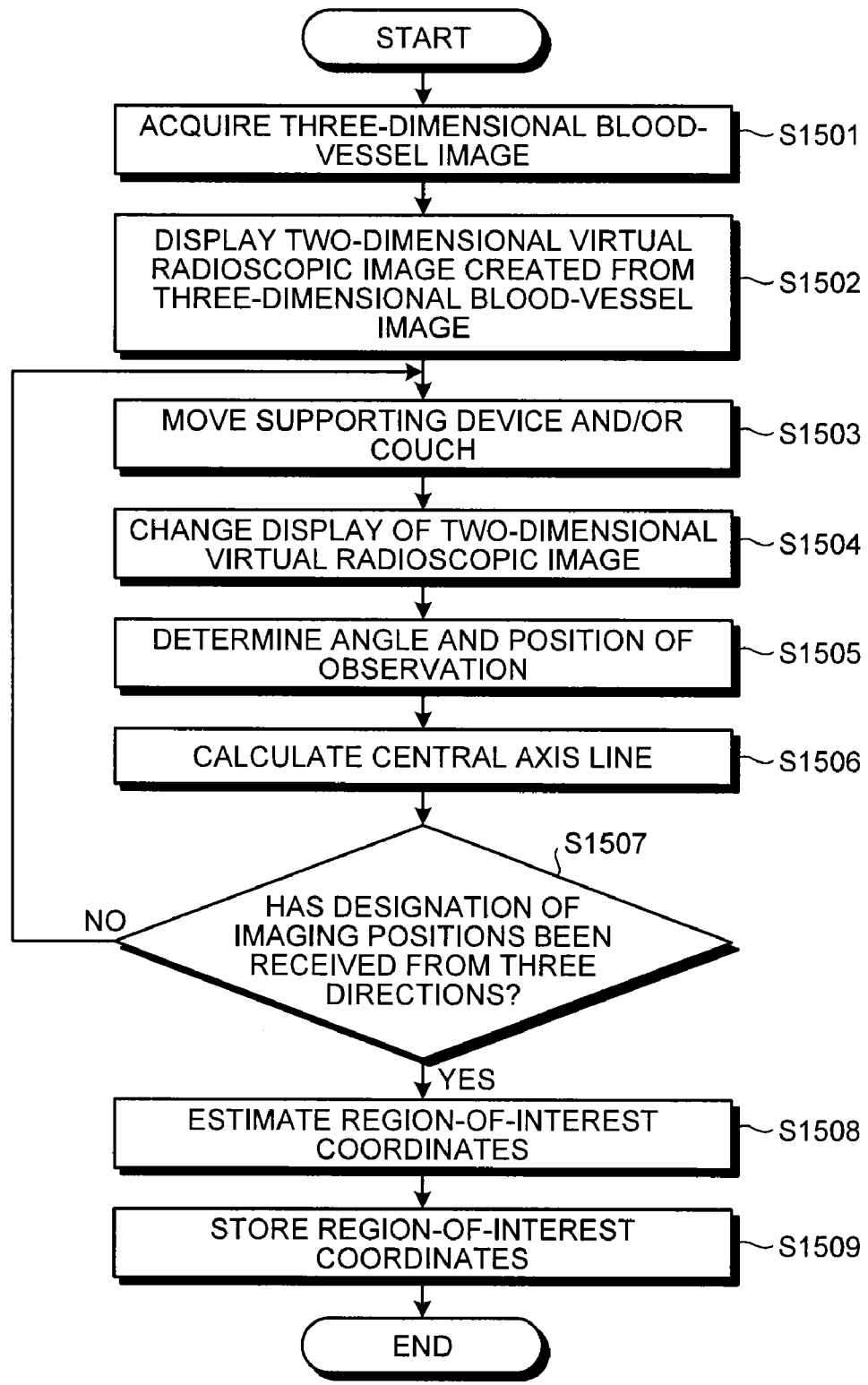

X-RAY DIAGNOSIS APPARATUS FOR CREATING A DISPLAY IMAGE FROM THREE-DIMENSIONAL MEDICAL IMAGE DATA

CROSS-REFERENCE TO RELATED APPLICATIONS

This application is based upon and claims the benefit of priority from the prior Japanese Patent Application No. 2009-039869, filed on Feb. 23, 2009, and No. 2010-023363, filed on Feb. 4, 2010; the entire contents of which are incorporated herein by reference.

BACKGROUND OF THE INVENTION

1. Field of the Invention

The present invention relates to an X-ray diagnosis apparatus.

2. Description of the Related Art

Recently, an X-ray diagnosis apparatus is used during a treatment as well as during an examination. For example, according to a coil embolization that is an intervention treatment for a head aneurysm, a filling state of a coil is an important factor that leads to a successful treatment. For this reason, to begin with, during an examination, an operator of the X-ray diagnosis apparatus carries out rotational imaging of a head of a subject by using the X-ray diagnosis apparatus, thereby specifying the shape and the position of an aneurysm from acquired three-dimensional blood-vessel image data. During a treatment, the operator then performs imaging while changing an imaging angle, or performs imaging from several directions by using an X-ray diagnosis apparatus of a bi plane type, and confirms a filling state of a coil from taken X-ray images.

However, because an aneurysm is small, usually 10 millimeters or smaller, an operator often performs imaging by enlarging a field of view of the imaging during a treatment; if the imaging angle is changed, a region of interest of the subject may be sometimes dislocated from the field of view (dislocated from an effective image reception area of a detector) in some cases. In such case, to find the region of interest, the operator reduces the scale of image enlargement at first so as to observe a wider region, and while observing a radioscopic image by further radiating X-rays onto the subject, the operator adjusts imaging positions (for example, the angle of a supporting device, the position of the supporting device, the position of a couch, and the height of the couch), and arranges the region of interest to the center of the field of view so as to observe the region of interest easily. After that, to observe the region of interest easily, the operator again performs a fine adjustment of the scale of image enlargement and the imaging positions while observing a radioscopic image by radiating X-rays onto the subject. Moreover, when using the X-ray diagnosis apparatus of the bi plane type during a treatment, the operator needs to position the region of interest of the subject at the center of the field of view by repeating the same procedure as described above as an initial setting, and to perform a fine adjustment to make the scale of image enlargement and the imaging positions more suitable for the treatment.

For this reason, conventionally a technology has been disclosed that the operator specifies the position of a region of interest by imaging the subject from a plurality of directions such that the specified position comes to the center of rotation of a C-arm of the X-ray diagnosis apparatus. A technology of specifying the position of a region of interest on a three-dimensional image is also disclosed (for example, JP-A 2001-204718 (KOKAI), and JP-A 2002-136507 (KOKAI)).

However, the conventional technologies described above have a problem that operation efficiency is decreased. Precisely, according to JP-A 2001-204718 (KOKAI), the position of a region of interest needs to be specified by performing imaging from at least two directions; and according to JP-A 2002-136507 (KOKAI), the position of a region of interest needs to be specified on a three-dimensional image. However, such specifying operations are not included in a clinical work flow, consequently produce additional time and effort onto the operator, and reduce operation efficiency. In addition, only specifying a region of interest to come to the center of a field of view is not enough to carry out a treatment, and a fine adjustment of the scale of image enlargement and imaging positions need to be further performed while confirming a radioscopic image by radiating X-rays onto the subject, still there is radiation exposure during the fine adjustment that is irrelevant to the essence of the treatment.

SUMMARY OF THE INVENTION

According to one aspect of the present invention, an X-ray diagnosis apparatus includes a display-image creating unit that creates a display image from three-dimensional medical image data such that a display image of three-dimensional medical image data substantially matches up with an anatomical structure on an acquired image by the X-ray diagnosis apparatus; a display-image changing unit that changes a display image so as to maintain consistency of an anatomical structure in accordance with change in an acquiring condition by the X-ray diagnosis apparatus; and a display unit that displays a display image that is at least one of created and changed by at least one of the display-image creating unit and the display-image changing unit.

BRIEF DESCRIPTION OF THE DRAWINGS

FIG. 3 is a flowchart of a process procedure performed by the X-ray diagnosis apparatus according to the first embodiment;

FIG. 7 is a functional block diagram of a configuration of the X-ray diagnosis apparatus according to the second embodiment;

FIG. 11 is a flowchart of a process procedure during an examination performed by an X-ray diagnosis apparatus according to a modification 2-2 of the second embodiment;

FIG. 12 is a flowchart of a process procedure during an examination performed by an X-ray diagnosis apparatus according to a modification 2-3 of the second embodiment;

FIG. 13 is a flowchart of a process procedure during an examination performed by an X-ray diagnosis apparatus according to a modification 2-4 of the second embodiment;

FIGS. 14A and 14B are flowcharts of process procedures during an examination performed by an X-ray diagnosis apparatus according to a third embodiment of the present invention;

FIGS. 15A and 15B are flowcharts of process procedures during an examination performed by an X-ray diagnosis apparatus according to a fourth embodiment of the present invention;

FIGS. 19A and 19B are flowcharts of process procedures during an examination performed by an X-ray diagnosis apparatus according to a sixth embodiment of the present invention;

FIG. 20 is a flowchart of a process procedure by an X-ray diagnosis apparatus according to a seventh embodiment of the present invention;

DETAILED DESCRIPTION OF THE INVENTION

Exemplary embodiments of an X-ray diagnosis apparatus according to the present invention will be explained below in detail with reference to the accompanying drawings. The present invention is not limited to the following embodiments.

During an intervention treatment of a head aneurysm, to grasp the shape of an aneurysm, a three-dimensional blood-vessel image is taken substantially without exception, and three-dimensional blood-vessel image data is acquired. An X-ray diagnosis apparatus according to a first embodiment of the present invention determines imaging conditions (such as an observation field of view, and imaging positions) by using the preliminarily acquired three-dimensional blood-vessel image data. Specifically, conventionally, X-rays are actually radiated onto a subject, and an operator determines the scale of image enlargement and imaging positions, such as the angle of a supporting device, the position of the supporting device, the position of a couch, and the height of the couch, while confirming on a radioscopic image. Compared to this, the X-ray diagnosis apparatus according to the first embodiment calculates a virtual radioscopic image by calculation from preliminarily acquired three-dimensional blood-vessel image data, and then determines imaging conditions by using the calculated virtual radioscopic image. Consequently, it can be expected that X-ray radiation irrelevant to the essence of a treatment can be reduced, and unnecessary exposure to radiation can be reduced.

Figure 1:
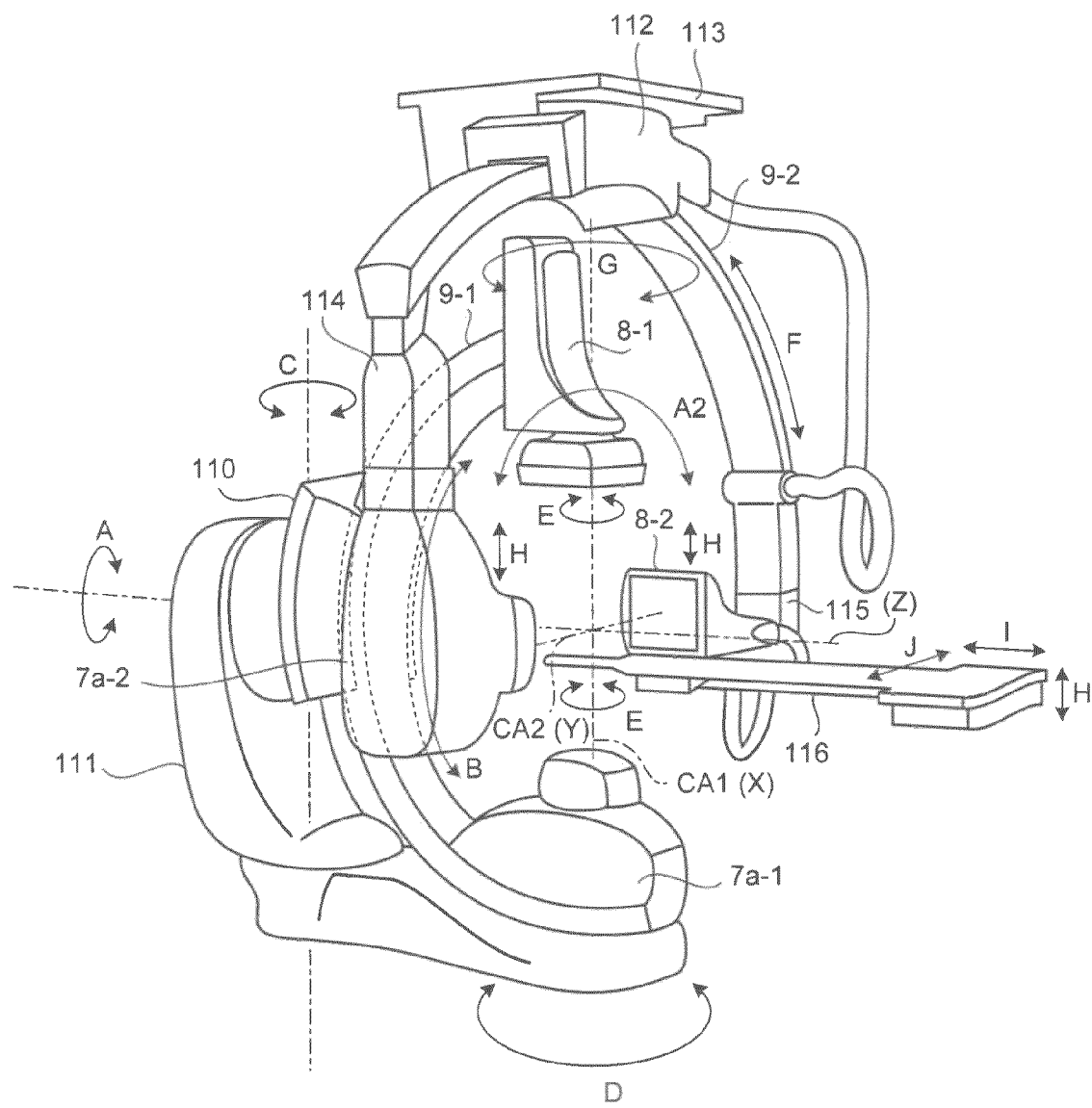
FIG. 1 is a perspective view of an appearance of the X-ray diagnosis apparatus according to a first embodiment of the present invention.

First of all, an appearance of the X-ray diagnosis apparatus according to the first embodiment is explained below with reference to FIG. 1. FIG. 1 is a perspective view of an appearance of the X-ray diagnosis apparatus according to the first embodiment. As explained below, according to the first embodiment, although it is assumed that the X-ray diagnosis apparatus is that of a bi plane type, it is not limited to this, and can be similarly applied to a case where the X-ray diagnosis apparatus is that of a single plane type.

As shown in FIG. 1, the X-ray diagnosis apparatus according to the first embodiment is an X-ray diagnosis apparatus of the bi plane type, and includes an X-ray imaging system of a front side system (first X-ray imaging system), and an X-ray imaging system of a lateral side system (second X-ray imaging system), and it is configured capable to image a subject P placed on a top plate 116 simultaneously from two directions. Moreover, the first X-ray imaging system is equipped with a five-axis rotation mechanism as explained below.

At first, the first X-ray imaging system is explained below. A first X-ray generating tube 7a-1 is mounted on an end of a first supporting device 9-1 (C-arm), and a first plane detector 8-1 is mounted on the other end of the first supporting device 9-1 (C-arm). CA1 denotes a first imaging central-axis of the first X-ray imaging system that connects the center of an image reception area of the first plane detector 8-1, a focus point of the first X-ray generating tube 7a-1, and a fixed point called an iso center.

In the first X-ray imaging system, the first supporting device 9-1 (C-arm) that is formed in an arc and designed to be placed on a floor is supported via an arm holder 110 by a stand 111 that is fixed on the floor. The arm holder 110 and the stand 111 are included in a first supporting device supporting mechanism that rotatably supports the first supporting device 9-1 (C-arm).

The first X-ray imaging system is equipped with a five-axis rotation mechanism that two axes of floor rotation and plane-detector/X-ray beam-limiting device rotation are added to a three-axis rotation mechanism of main rotation, slide rotation, and column rotation of the first supporting device 9-1 (C-arm). Specifically, the stand 111 has a structure that allows the arm holder 110 to rotate axially along an arrow A (A2). The arm holder 110 has a structure that allows the first supporting device 9-1 (C-arm) to slide and to rotate along an arrow B. Moreover, the stand 111 has a structure that allows column rotation (turn) along an arrow C. Furthermore, the stand 111 has a structure that allows floor rotation along an arrow D. The first plane detector 8-1 and the first X-ray generating tube 7a-1 mounted on the first supporting device 9-1 (C-arm) have a structure that allows rotation along an arrow E.

According to such structures, the first X-ray imaging system can arbitrarily tilt an imaging angle with respect to the arrow A (A2) and the arrow B. Moreover, the first X-ray imaging system can move between (two-directional) imaging positions and a waiting position located inside a second supporting device 9-2 (Ω-arm) by turning with respect to the arrow C and the arrow D. Furthermore, the first X-ray imaging system can arbitrarily rotate the image reception area by turning with respect to the arrow E.

The rotational axis of the arrow D and the rotational axis of the arrow E match the first imaging central-axis CA1. The rotational axis of the arrow A is orthogonal to the first imaging central-axis CA1. The rotational axis of the arrow B is orthogonal to the first imaging central-axis CA1. The rotational axis of the arrow A is orthogonal to the rotational axis of the arrow B. The rotational axes of the three orthogonal axes (the first imaging central-axis CA1, the rotational axis of the arrow A, and the rotational axis of the arrow B) are provided so as to intersect one another at one point. The point is the iso center. In this way, because the rotational axes of the three orthogonal axes are provided so as to intersect one another at the iso center, even if the imaging direction is changed by rotating the first supporting device 9-1 (C-arm), the center point of a display image (the center of the field of view) matches the iso center.

Then, the second X-ray imaging system is explained below. In the second X-ray imaging system, a second X-ray generating tube 7a-2 is mounted on one end of the second supporting device 9-2 (Ω-arm) via a first elevating mechanism 114, and a second plane detector 8-2 is mounted on the other end of the second supporting device 9-2 (Ω-arm) via a second elevating mechanism 115. CA2 denotes a second imaging central-axis of the second X-ray imaging system that connects the center of an image reception area of the second plane detector 8-2, a focus point of the second X-ray generating tube 7a-2, and a fixed point called an iso center.

In the second X-ray imaging system, the second supporting device 9-2 (Ω-arm) that is formed in an arc and designed to be hung from a ceiling is hung from a slider base 113 via an arm holder 112. The arm holder 112 supports the second supporting device 9-2 (Ω-arm) in a slidably rotatable manner in the direction of an arrow F along an arc. The slider base 113 supports the arm holder 112 in an axially rotatable manner along an arrow G. Respective ends of the second supporting device 9-2 (Ω-arm) are provided with the first elevating mechanism 114 and the second elevating mechanism 115 respectively extending downward. The second X-ray generating tube 7a-2 is supported under the bottom end of the first elevating mechanism 114. The second plane detector 8-2 is supported at the bottom end of the second elevating mechanism 115. The second X-ray generating tube 7a-2 and the second plane detector 8-2 are opposed to each other on the second imaging central-axis CA2. The first elevating mechanism 114 and the second elevating mechanism 115 elevate and lower the second X-ray generating tube 7a-2 and the second plane detector 8-2 upward and downward along an arrow H while keeping the opposition. The slider base 113 is supported in a movable manner in crisscrossing directions by being engaged to a running rail (omitted in the figure) provided on the ceiling surface. The arm holder 112 and the slider base 113 are included in a second supporting device supporting mechanism that supports the second supporting device 9-2 (Ω-arm) in a rotatable manner.

The not-shown couch supports the top plate 116 in a liftable and lowerable manner with respect to the upward-downward direction H, and in a slidable manner in a direction I that is parallel to a longitudinal-axis direction Z of the top plate 116, and a direction J that is parallel to a transverse-axis direction X of the top plate 116.

The first imaging central-axis CA1 of the first X-ray imaging system and the second imaging central-axis CA2 of the second X-ray imaging system intersect each other at the iso center. A position of the first X-ray imaging system when the first imaging central-axis CA1 passes through the iso center is referred to as the imaging position of the first X-ray imaging system, and similarly, a position of the second X-ray imaging system when the second imaging central-axis CA2 passes through the iso center is referred to as the imaging position of the second X-ray imaging system. When the both systems are located at the respective imaging positions, such state is referred to as two-directional imaging positions.

The first X-ray imaging system and the second X-ray imaging system according to such configurations carry out imaging operation by being controlled on movement by a mechanism control unit 3, which is not shown, so as to match up, for example, an intersection point of the first imaging central-axis CA1 and the second imaging central-axis CA2 with a region of interest of the subject, where the first imaging central-axis CA1 corresponding to the first X-ray generating tube 7a-1 and the first plane detector 8-1, and the second imaging central-axis CA2 corresponding to the second X-ray generating tube 7a-2 and the second plane detector 8-2.

Figure 2:
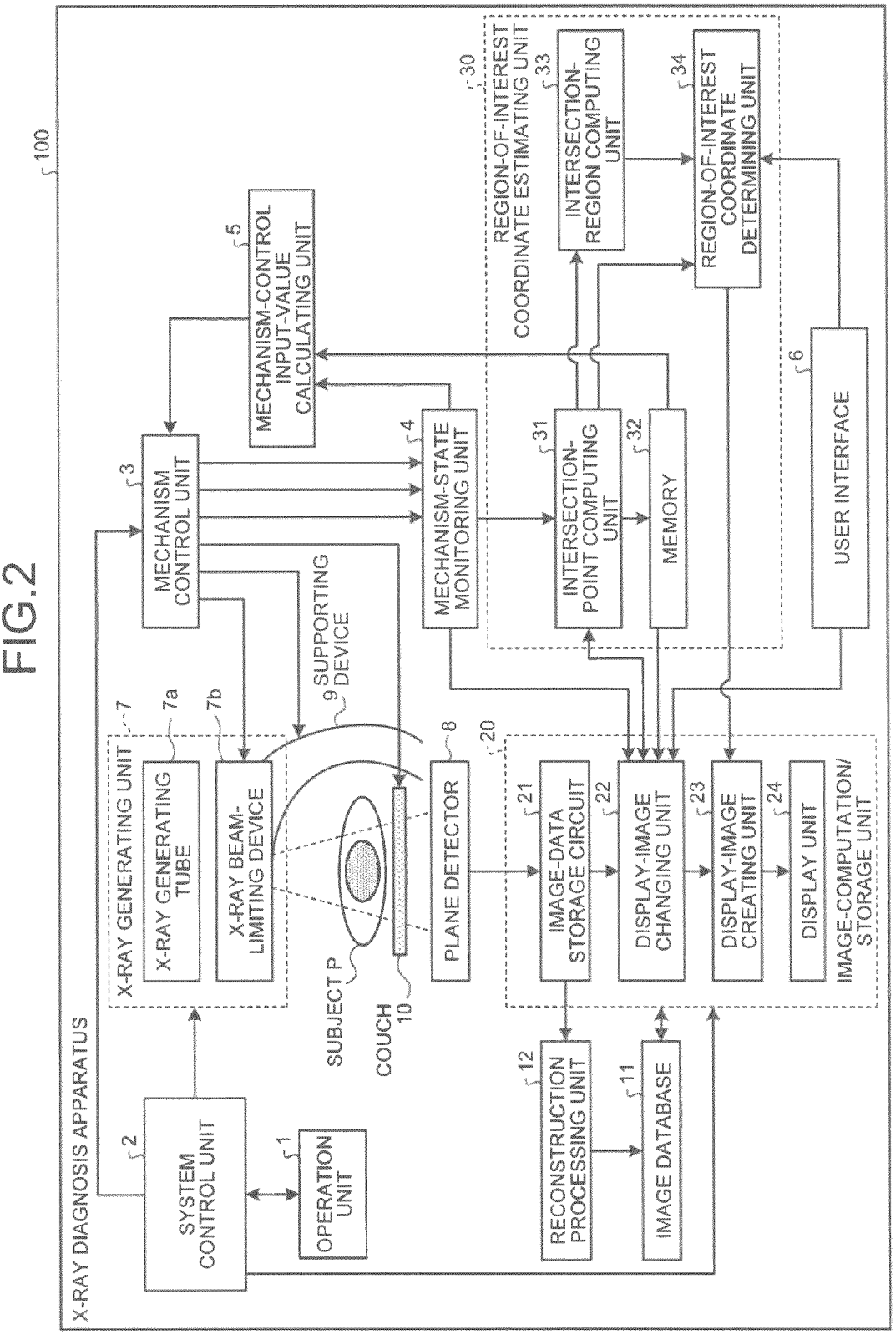
FIG. 2 is a functional block diagram of a configuration of the X-ray diagnosis apparatus according to the first embodiment.

Then, a configuration of the X-ray diagnosis apparatus according to the first embodiment is explained below with reference to FIG. 2. FIG. 2 is a functional block diagram of a configuration of the X-ray diagnosis apparatus according to the first embodiment. Specific operation of each unit will be described in detail when explaining a process procedure.

As shown in FIG. 2, an X-ray diagnosis apparatus 100 according to the first embodiment includes an operation unit 1, a system control unit 2, the mechanism control unit 3, a mechanism-state monitoring unit 4, a mechanism-control input-value calculating unit 5, a user interface 6, an X-ray generating unit 7, a plane detector 8, a supporting device 9, a couch 10, an image database 11, a reconstruction processing unit 12, an image-computation/storage unit 20, and a region-of-interest coordinate estimating unit 30.

The operation unit 1 includes a mouse, a key board, a button, a track ball, a joy stick, and the like, for the operator, such as a doctor or an engineer, who operates the X-ray diagnosis apparatus 100, to input various commands, and transfers a command received from the operator to the system control unit 2.

The system control unit 2 controls operation of the whole of the X-ray diagnosis apparatus 100. Precisely, the system control unit 2 performs rotation and movement control on the supporting device 9, movement control on the couch 10, adjustment of X-ray dosage, and ON/OFF control of X-ray radiation by controlling the mechanism control unit 3 and the X-ray generating unit 7 based on a command from the operator transferred from the operation unit 1.

Moreover, the system control unit 2 provides control so as to display image data stored by the image database 11, image data processed through image processing by the image-computation/storage unit 20, a Graphical User Interface (GUI) for receiving a command from the operator, and the like, onto a display unit 24, by controlling the image-computation/storage unit 20 based on a command from the operator.

The mechanism control unit 3 controls rotation and movement of the supporting device 9, movement of the couch 10, and a diaphragm of an X-ray beam-limiting device 7b. Specifically, the mechanism control unit 3 controls the supporting device 9, the couch 10, and/or the X-ray beam-limiting device 7b in accordance with an amount of control calculated by the mechanism-control input-value calculating unit 5.

The mechanism-state monitoring unit 4 acquires current state information about the supporting device 9 and the couch 10 (for example, the angle of the supporting device 9) from the mechanism control unit 3.

The mechanism-control input-value calculating unit 5 calculates an amount of control to be used for control of the supporting device 9 and/or the couch 10 by using region-of-interest coordinates.

The user interface 6 receives from the operator a selection instruction to select a certain intersection point as region-of-interest coordinates, when a plurality of intersection points is calculated as region-of-interest coordinate candidates.

The X-ray generating unit 7 includes an X-ray generating tube 7a and the X-ray beam-limiting device 7b. The X-ray generating tube 7a (the first X-ray generating tube 7a-1 and the second X-ray generating tube 7a-2) generates an X-ray by using a high voltage. The X-ray beam-limiting device 7b (a first X-ray beam-limiting device 7b-1, and a second X-ray beam-limiting device 7b-2) limits X-rays generated by the X-ray generating tube 7a so as to be selectively radiated onto a region of interest of the subject P. For example, the X-ray beam-limiting device 7b includes four slidable diaphragm blades, and causes X-rays generated by the X-ray generating tube 7a to be limited and radiated onto the subject P by sliding the diaphragm blades.

The plane detectors 8 (the first plane detector 8-1 and the second plane detector 8-2) is a device in which X-ray detecting elements for detecting an X-ray passed through the subject P are arranged in a matrix, and each of the X-ray detecting elements converts an X-ray passed through the subject P into an electric signal and stores it, and transmits the stored electric signal to an image-data storage circuit 21, which will be described later.

The supporting device 9 (the first supporting device 9-1 and the second supporting device 9-2) is an arm that supports the X-ray generating tube 7a, the X-ray beam-limiting device 7b, and the plane detector 8, so that the X-ray generating tube 7a and the X-ray beam-limiting device 7b, and the plane detector 8 are arranged with the supporting device 9 on opposite sides of the subject P.

The couch 10 is a bed on which the subject P is to be placed.

The image database 11 stores therein image data processed through image processing by the image-computation/storage unit 20, image data reconstructed by the reconstruction processing unit 12, image data imaged by the X-ray diagnosis apparatus 100, and the like. The image data stored by the image database 11 is also processed through display and image processing by the image-computation/storage unit 20.

The reconstruction processing unit 12 performs reconstruction processing on raw data stored by the image-data storage circuit 21 based on an instruction from the operator received via the operation unit 1, and creates three-dimensional reconstruction image.

The image-computation/storage unit 20 performs display, storage, and image processing of image data imaged by the X-ray diagnosis apparatus 100. Specifically, the image-computation/storage unit 20 includes the image-data storage circuit 21, a display-image changing unit 22, a display-image creating unit 23, and the display unit 24. The image-data storage circuit 21 stores therein raw data detected by the plane detector 8. The display-image changing unit 22 calculates a value required to change a virtual radioscopic image based on present state information received from the mechanism-state monitoring unit 4 about the angle of the supporting device 9, the position of the supporting device 9, the position of the couch 10, the height of the couch 10, the scale of image enlargement, the X-ray beam-limiting device 7b, and a compensating filter. The display-image creating unit 23 creates a two-dimensional virtual radioscopic image from three-dimensional medical image data. The display unit 24 displays a GUI for receiving a command from the operator via the operation unit 1, image data stored by the image database 11, image data processed through image processing by the display-image creating unit 23 and the display-image changing unit 22, and the like.

The region-of-interest coordinate estimating unit 30 estimates region-of-interest coordinates indicating the center of a region of interest of the subject P from three-dimensional image data of rendering the region of interest. Specifically, the region-of-interest coordinate estimating unit 30 includes an intersection-point computing unit 31, a memory 32, an intersection-region computing unit 33, and a region-of-interest coordinate determining unit 34. The intersection-point computing unit 31 estimates region-of-interest coordinates (or calculates an intersection point to be a candidate of region-of-interest coordinates) by calculating the central axis that connects the image reception area of the plane detector 8, the focus point of the X-ray generating tube 7a, and the iso center, and calculating the center point with respect to an aggregation of pixels continuously present on the central axis. The memory 32 stores therein region-of-interest coordinates estimated by the intersection-point computing unit 31. When a plurality of intersection points is calculated by the intersection-point computing unit 31, the intersection-region computing unit 33 calculates an intersection region required for selecting as region-of-interest coordinates (the volume of a region that has pixel values within a certain range from an intersection point, a distance between the intersection point and the end point on the central axis on the side of the plane detector 8, and the like). The region-of-interest coordinate determining unit 34 determines region-of-interest coordinates from among a plurality of intersection points by using an intersection region calculated by the intersection-region computing unit 33.

A process procedure performed by the X-ray diagnosis apparatus according to the first embodiment is explained below with reference to FIG. 3. FIG. 3 is a flowchart of a process procedure performed by the X-ray diagnosis apparatus according to the first embodiment. The following description explains an intervention treatment for a head aneurysm as an example.

As shown in FIG. 3, when an examination is started, to begin with, the X-ray diagnosis apparatus 100 rotationally images a head of the subject P, and acquires three-dimensional blood-vessel image data (Step S1). For example, when raw data acquired by the plane detector 8 is stored in the image-data storage circuit 21, the reconstruction processing unit 12 performs reconstruction processing, and stores reconstructed three-dimensional blood-vessel image data into the image database 11.

The X-ray diagnosis apparatus 100 then displays the three-dimensional blood-vessel image data (Step S2). Specifically, the display-image creating unit 23 reads the three-dimensional blood-vessel image data from the image database 11, and furthermore, creates an initial two-dimensional virtual radioscopic image based on present state information received from the mechanism-state monitoring unit 4 about the angle of the supporting device 9, the position of the supporting device 9, the position of the couch 10, the height of the couch 10, the scale of image enlargement, the X-ray beam-limiting device 7b, and the compensating filter.

Figure 4A:
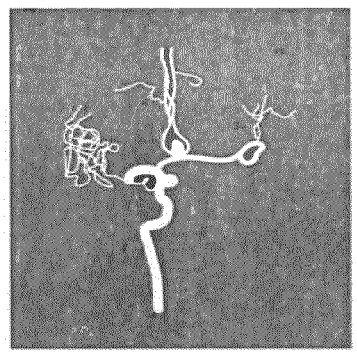
FIGS. 4A to 4G are schematic diagrams that depict an example of display images of two-dimensional virtual radioscopic images.

For example, the first X-ray imaging system shown in FIG. 1 is considered below. It is assumed that when creating a display image, the first X-ray imaging system is in the initial state as shown in FIG. 1 equal to a state when the head is rotationally imaged. Precisely, assuming that the system coordinate system is a three-dimensional coordinate system having the origin at the iso center, the state is such that the origin of the three-dimensional coordinate system of acquired three-dimensional blood-vessel image data fully matches up with the coordinate system of the system. However, it is assumed that the first supporting device 9-1 (C-arm) does not rotate with respect to the rotational axis of the arrow A (vertical to the ground). In such state, the display-image creating unit 23 creates a two-dimensional projection image (hereinafter, "initial position image", which means an image at the initial position) from three-dimensional blood-vessel image data, by assuming a projection viewpoint is the focus point of the X-ray generating tube 7a, and a projection plane is a detector surface of the plane detector 8. For example, FIG. 4A is an example of an initial position image.

Subsequently, the X-ray diagnosis apparatus 100 receives change in acquiring conditions by the operator (Step S3); and changes display of the three-dimensional blood-vessel image data (Step S4).

Figure 4B:
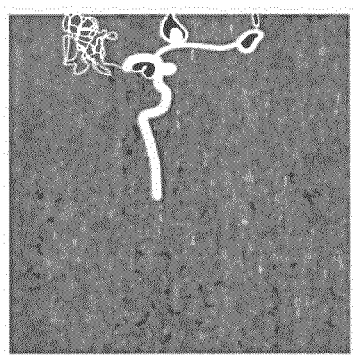

For example, as an example of a change in the acquiring conditions, horizontal movement of the couch 10 is explained below. For example, suppose the operator moves the couch 10 via the operation unit 1 to a head side of a patient (the subject P) in the direction I shown in FIG. 1. The mechanism-state monitoring unit 4 then calculates a transition amount $\Delta I$ from the initial state of the couch 10. The display-image changing unit 22 then calculates an amount of translation $\Delta v$ of a three-dimensional image based on $\Delta I$ received from the mechanism-state monitoring unit 4. In addition, the display-image creating unit 23 changes the display position of the two-dimensional projection image based on $\Delta v$. Precisely, the display-image creating unit 23 displays a two-dimensional projection image that the image is translated upward as shown in FIG. 4B as synchronized with that the couch 10 moves toward the head side of the patient.

Figure 4C:
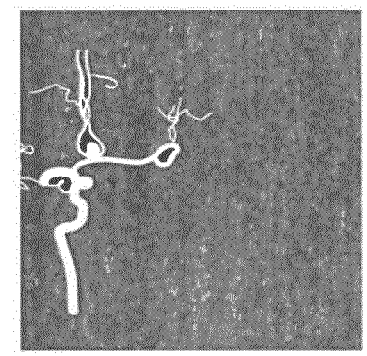

Moreover, for example, as another example of a change in the acquiring conditions, horizontal movement of the couch 10 is explained below. For example, suppose the operator moves the couch 10 via the operation unit 1 to the right side of the patient in the direction J shown in FIG. 1. The mechanism-state monitoring unit 4 then calculates a transition amount $\Delta J$ from the initial state of the couch 10. The display-image changing unit 22 then calculates an amount of translation $\Delta h$ of a three-dimensional image based on $\Delta J$ received from the mechanism-state monitoring unit 4. In addition, the display-image creating unit 23 changes the display position of the two-dimensional projection image based on $\Delta h$. Precisely, the display-image creating unit 23 displays a two-dimensional projection image that the image is translated leftward as shown in FIG. 4C as synchronized with that the couch 10 moves toward the right side of the patient.

Figure 4D:
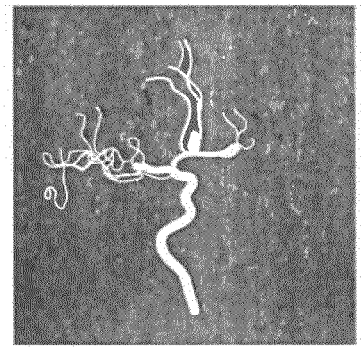

Furthermore, for example, as another example of a change in the acquiring conditions, rotation of the supporting device 9 is explained below. For example, suppose the operator rotates the first supporting device 9-1 via the operation unit 1 to the right side of the patient in the direction A shown in FIG. 1. The mechanism-state monitoring unit 4 then calculates a transition angle amount $\Delta A$ from the initial state of the first supporting device 9-1. The display-image changing unit 22 then calculates a transition angle amount $\Delta a$ of a three-dimensional image in the projection direction based on $\Delta A$ received from the mechanism-state monitoring unit 4. In addition, the display-image creating unit 23 changes the projection direction based on $\Delta a$, and displays a two-dimensional projection image that the image is rotationally moved as shown in FIG. 4D as synchronized with that the first supporting device 9-1 rotates around the rotational axis of the arrow A.

Figure 4E:
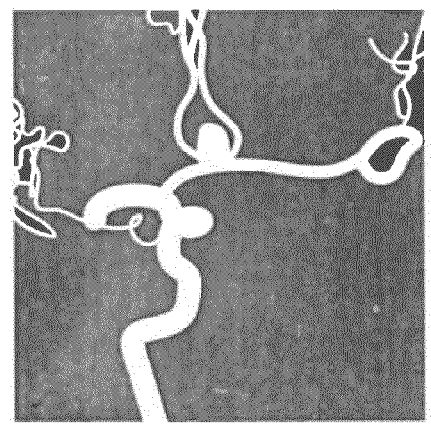

Moreover, for example, as another example of a change in the acquiring conditions, change in the scale of image enlargement is explained below. For example, suppose the operator changes the scale of enlargement of image via the operation unit 1. The mechanism-state monitoring unit 4 then outputs a scale of enlargement Ma in the initial state, and a scale of enlargement Mb after the change, to the display-image changing unit 22. The display-image changing unit 22 then calculates a ratio of scale of image enlargement Mr=Mb/Ma, based on the scale of enlargement Ma in the initial state and the scale of enlargement Mb after the change. In addition, the display-image creating unit 23 changes the scale of enlargement of display image based on Mr, and displays a two-dimensional projection image that the scale of enlargement of display image is changed as shown in FIG. 4E as synchronized with change in the scale of enlargement.

For example, also when the operator elevates or lowers the couch 10 via the operation unit 1 in the direction H shown in FIG. 1, a distance between the subject P and the focus point of the X-ray generating tube 7a and the plane detector 8 is changed, consequently the scale of image enlargement is changed. The mechanism-state monitoring unit 4 then calculates a transition amount $\Delta H$ from the initial state of the couch 10 in the straight direction between the focus of the X-ray generating tube 7a and the center of the plane detector 8. The display-image changing unit 22 then calculates a change scale of enlargement Mh of projection image based on $\Delta H$. In addition, the display-image creating unit 23 changes the scale of enlargement of display image based on Mh, and displays a two-dimensional projection image that the scale of enlargement of image is changed as shown in FIG. 4E as synchronized with upward/downward movement of the couch 10.

Figure 4F:
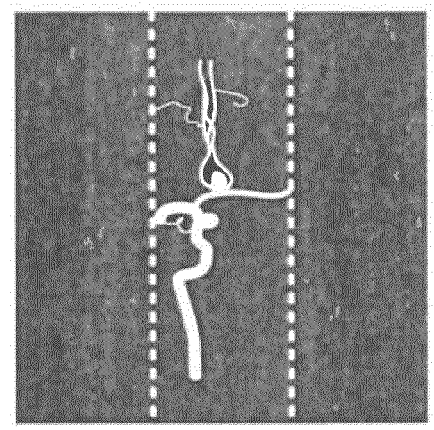
Figure 4G:
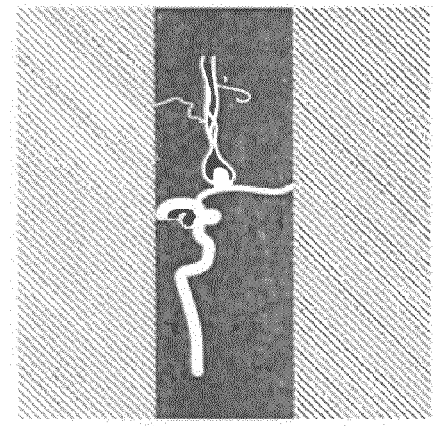

Furthermore, for example, as another example of a change in the acquiring conditions, an X-ray diaphragm is explained below. To reduce unnecessary radiation exposure, an X-ray diaphragm can be sometimes inserted by the operator into a region other than a region intended to be observed in some cases. The mechanism-state monitoring unit 4 then calculates a transition amount $\Delta C$ from the initial state of the X-ray diaphragm. The display-image changing unit 22 then calculates a region S covered with the X-ray diaphragm on a projection of the three-dimensional image based on $\Delta C$. In addition, the display-image creating unit 23 displays such that the region S is not to be displayed on a display image based on the region S, as shown in FIG. 4F. Alternatively, the display-image creating unit 23 can change a display pattern of the region S as shown in FIG. 4G. As well as pattern, color and brightness can be changed. Furthermore, not limited to the X-ray diaphragm, the compensating filter can be similarly displayed.

After that, the X-ray diagnosis apparatus 100 determines whether the examination or the treatment is finished (Step S5); and if it is finished (Yes at Step S5), the processing is terminated. By contrast, if it is not finished (No at Step S5), the X-ray diagnosis apparatus 100 goes back to the processing at Step S3, and again receives a change in the acquiring conditions by the operator.

The above examples are not limited to the respective cases, and can be used in combination. Although the examples are explained above about an example of a blood vessel image, not only a blood vessel, but also an image of a bone or soft tissue, and a Computed Tomography (CT) image or an image of Magnetic Resonance Imaging (MRI) can be used as a three-dimensional medical image.

As described above, according to the first embodiment, the display-image creating unit 23 creates a display image from three-dimensional medical image data such that a display image of three-dimensional medical image data substantially matches up with an anatomical structure on an acquired image by the X-ray diagnosis apparatus 100. The display-image changing unit 22 changes a display image so as to maintain consistency of an anatomical structure in accordance with change in acquiring conditions by the X-ray diagnosis apparatus 100. The display unit 24 displays a display image that is created and/or changed by the display-image creating unit 23 and/or the display-image changing unit 22. The acquiring condition is one of the angle of the supporting device, the position of the supporting device, the scale of image enlargement, the position of the couch, the height of the couch, the X-ray beam-limiting device, and the compensating filter, or a combination of them.

Moreover, according to the first embodiment, the display-image creating unit 23 and/or the display-image changing unit 22 creates and/or changes a display image not to display a region that is made invisible by the X-ray beam-limiting device. Furthermore, according to the first embodiment, the display-image creating unit 23 and/or the display-image changing unit 22 creates and/or changes a display image so as to change at least one of the color, the pattern, and the brightness of a region onto which all or part of X-rays are blocked by the X-ray beam-limiting device and/or the compensating filter.

In this way, according to the first embodiment, a clinical work flow is improved, so that operation efficiency can be improved. Moreover, according to the first embodiment, radiation exposure during a fine adjustment that is irrelevant to the essence of a treatment is eliminated, consequently, unnecessary radiation exposure can be reduced.

Figure 5A:
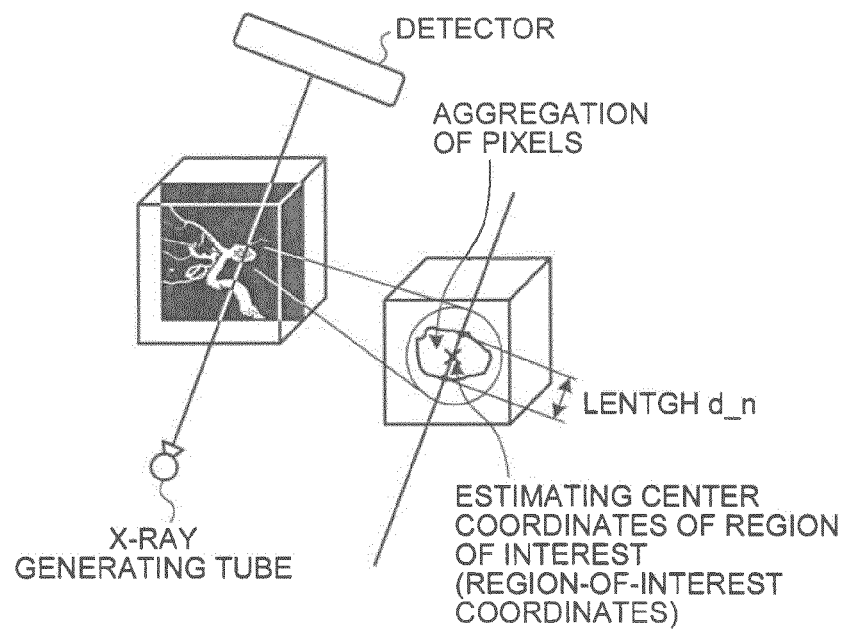
FIGS. 5A to 5C are schematic diagrams for explaining an outline of an X-ray diagnosis apparatus according to a second embodiment of the present invention.
Figure 5B:
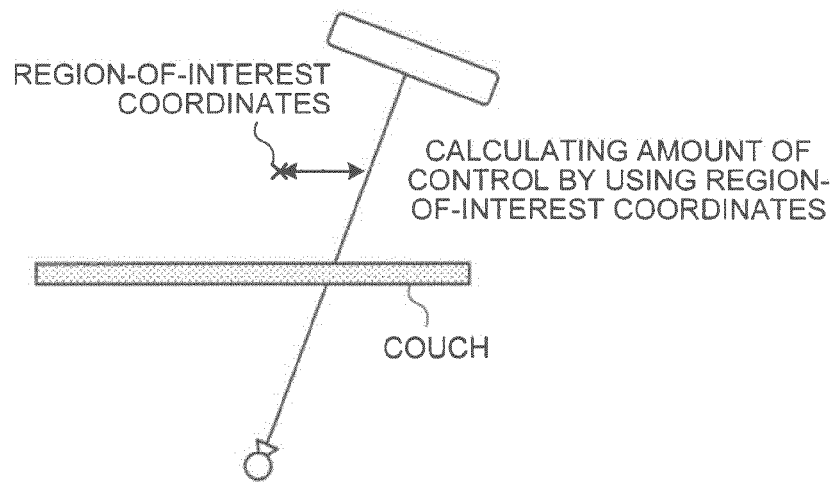
Figure 5C:
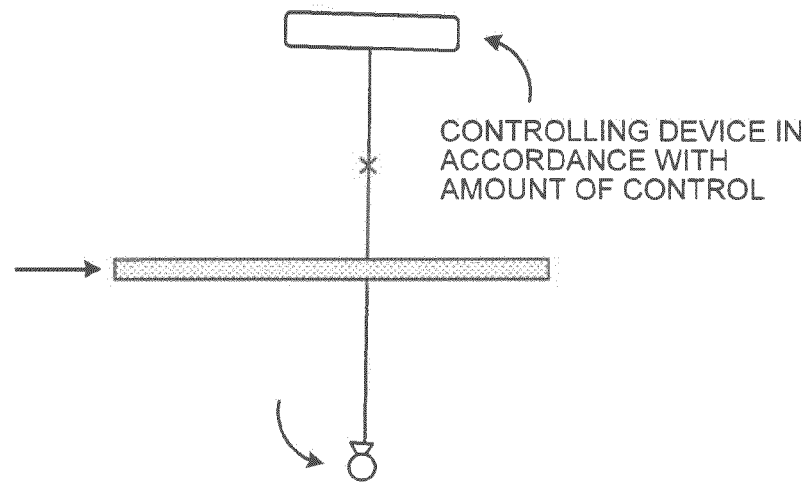

First of all, an outline of an X-ray diagnosis apparatus according to a second embodiment of the present invention is explained below with reference to FIGS. 5A to 5C. FIGS. 5A to 5C are schematic diagrams for explaining an outline of the X-ray diagnosis apparatus according to the second embodiment.

The X-ray diagnosis apparatus according to the second embodiment creates a display image of rendering a region of interest of a subject in a two-dimensional space from medical image data of rendering the region of interest in a three-dimensional space. For example, as shown in FIG. 5A, the X-ray diagnosis apparatus creates a display image of rendering an aneurysm in a two-dimensional space.

Moreover, the X-ray diagnosis apparatus estimates region-of-interest coordinates that indicate the position of the region of interest in a three-dimensional space based on information specified about the display image. For example, when a doctor moves a supporting device and a couch such that the center of a region of interest comes to the center of a field of view and determines the angle and the position of observation; as shown in FIG. 5A, the X-ray diagnosis apparatus calculates a central axis that connects the center of an image reception area of a detector, a focus point of an X-ray generating tube, and an iso center (omitted in the figure), and calculates the center point with respect to an aggregation of pixels continuously present on the central axis based on the determined information about the display image, thereby estimating region-of-interest coordinates that indicate, for example, the center of an aneurysm.

The X-ray diagnosis apparatus then calculates an amount of control to be used for control of a certain device by using the estimated region-of-interest coordinates. For example, as shown in FIG. 5B, the X-ray diagnosis apparatus calculates an amount of control to be used for control of the supporting device (omitted in the figure) mounted with the X-ray generating tube and the detector, and an amount of control to be used for control of the couch.

The X-ray diagnosis apparatus then controls a certain device in accordance with the calculated amount of control. For example, the X-ray diagnosis apparatus controls the supporting device and the couch as shown in FIG. 5C.

In this way, the X-ray diagnosis apparatus according to the second embodiment controls the supporting device and the couch such that the region of interest is not to be dislocated from the field of view. Accordingly, the operator can constantly capture a region of interest in the center of the field of view, and saves time and effort for manually adjusting the X-ray diagnosis apparatus, thereby improving operation efficiency. Consequently, a time of imaging irrelevant to the essence of a treatment is shortened, and exposure to radiation can be also reduced.

Figure 6:
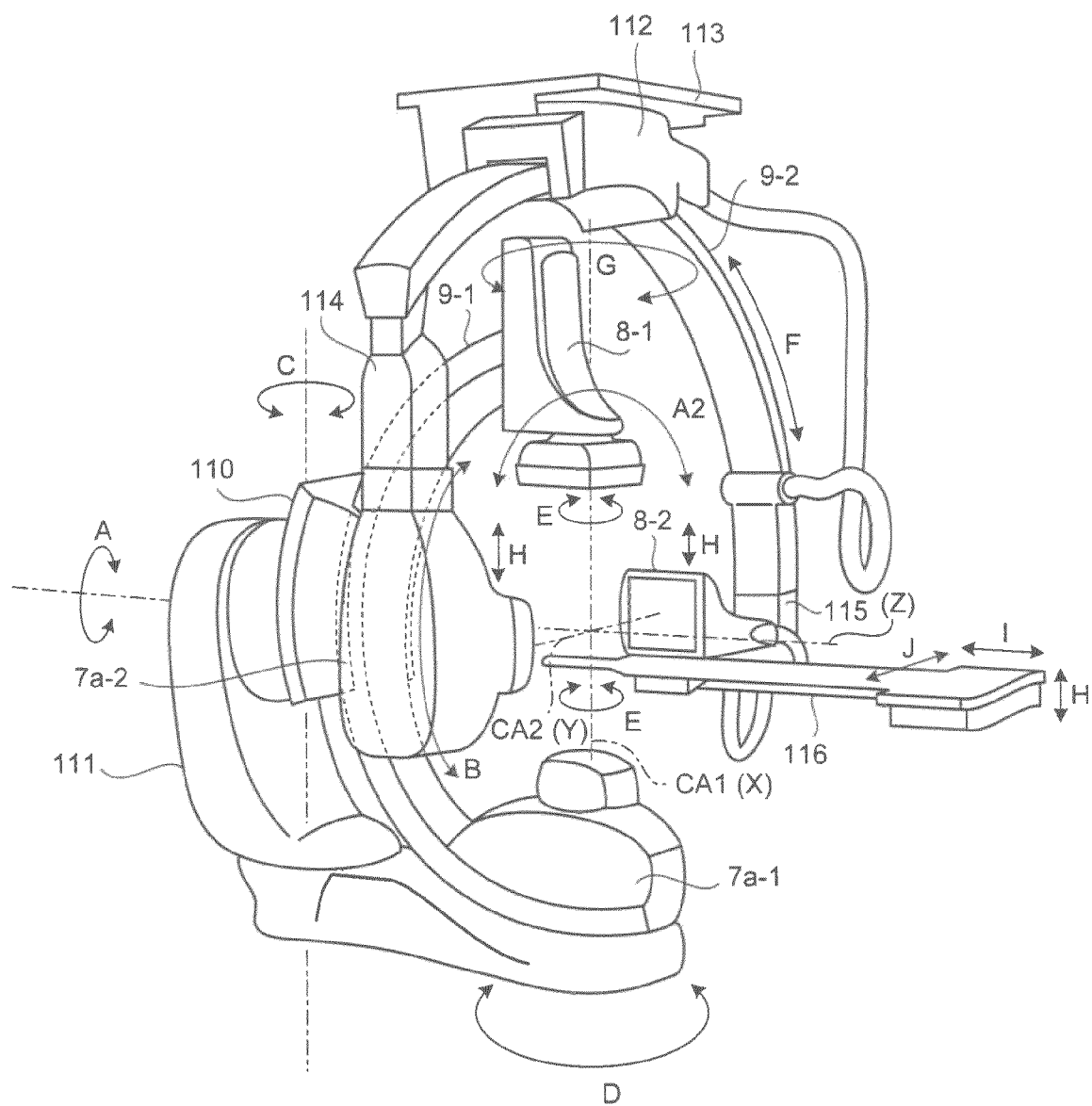
FIG. 6 is a perspective view of an appearance of the X-ray diagnosis apparatus according to the second embodiment.

Then, an appearance of the X-ray diagnosis apparatus according to the second embodiment is explained below with reference to FIG. 6. FIG. 6 is a perspective view of an appearance of the X-ray diagnosis apparatus according to the second embodiment. As explained below, according to the second embodiment, although it is assumed that the X-ray diagnosis apparatus is that of a bi plane type, it is not limited to this, and can be similarly applied to a case where the X-ray diagnosis apparatus is that of a single plane type.

As shown in FIG. 6, the X-ray diagnosis apparatus according to the second embodiment is an X-ray diagnosis apparatus of the bi plane type, and includes an X-ray imaging system of a front side system (first X-ray imaging system), and an X-ray imaging system of a lateral side system (second X-ray imaging system), and it is configured capable to image the subject P placed on the top plate 116 simultaneously from two directions. Moreover, the first X-ray imaging system is equipped with a five-axis rotation mechanism as explained below.

At first, the first X-ray imaging system is explained below. The first X-ray generating tube 7a-1 is mounted on an end of the first supporting device 9-1 (C-arm), and the first plane detector 8-1 is mounted on the other end of the first supporting device 9-1 (C-arm). CA1 denotes the first imaging central-axis of the first X-ray imaging system that connects the center of the image reception area of the first plane detector 8-1, a focus point of the first X-ray generating tube 7a-1, and a fixed point called an iso center.

In the first X-ray imaging system, the first supporting device 9-1 (C-arm) that is formed in an arc and designed to be placed on a floor is supported via the arm holder 110 by the stand 111 that is fixed on the floor. The arm holder 110 and the stand 111 are included in a first supporting device supporting mechanism that rotatably supports the first supporting device 9-1 (C-arm).

The first X-ray imaging system is equipped with a five-axis rotation mechanism that two axes of floor rotation and plane-detector/X-ray beam-limiting device rotation are added to a three-axis rotation mechanism of main rotation, slide rotation, and column rotation of the first supporting device 9-1 (C-arm). Specifically, the stand 111 has a structure that allows the arm holder 110 to rotate axially along an arrow A (A2). The arm holder 110 has a structure that allows the first supporting device 9-1 (C-arm) to slide and to rotate along an arrow B. Moreover, the stand 111 has a structure that allows column rotation (turn) along an arrow C. Furthermore, the stand 111 has a structure that allows floor rotation along an arrow D. The first plane detector 8-1 and the first X-ray generating tube 7a-1 mounted on the first supporting device 9-1 (C-arm) have a structure that allows rotation along an arrow E.

According to such structures, the first X-ray imaging system can arbitrarily tilt an imaging angle with respect to the arrow A (A2) and the arrow B. Moreover, the first X-ray imaging system can move between (two-directional) imaging positions and a waiting position located inside the second supporting device 9-2 (Ω-arm) by turning with respect to the arrow C and the arrow D. Furthermore, the first X-ray imaging system can arbitrarily rotate the image reception area by turning with respect to the arrow E.

The rotational axis of the arrow D and the rotational axis of the arrow E match the first imaging central-axis CA1. The rotational axis of the arrow A is orthogonal to the first imaging central-axis CA1. The rotational axis of the arrow B is orthogonal to the first imaging central-axis CA1. The rotational axis of the arrow A is orthogonal to the rotational axis of the arrow B. The rotational axes of the three orthogonal axes (the first imaging central-axis CA1, the rotational axis of the arrow A, and the rotational axis of the arrow B) are provided so as to intersect one another at one point. The point is the iso center. In this way, because the rotational axes of the three orthogonal axes are provided so as to intersect one another at the iso center, even if the imaging direction is changed by rotating the first supporting device 9-1 (C-arm), the center point of a display image (the center of the field of view) matches the iso center.

Then, the second X-ray imaging system is explained below. In the second X-ray imaging system, the second X-ray generating tube 7a-2 is mounted on one end of the second supporting device 9-2 (Ω-arm) via the first elevating mechanism 114, and the second plane detector 8-2 is mounted on the other end of the second supporting device 9-2 (Ω-arm) via the second elevating mechanism 115. CA2 denotes the second imaging central-axis of the second X-ray imaging system that connects the center of an image reception area of the second plane detector 8-2, a focus point of the second X-ray generating tube 7a-2, and a fixed point called an iso center.

In the second X-ray imaging system, the second supporting device 9-2 (Ω-arm) that is formed in an arc and designed to be hung from a ceiling is hung from the slider base 113 via the arm holder 112. The arm holder 112 supports the second supporting device 9-2 (Ω-arm) in a slidably rotatable manner in the direction of an arrow F along an arc. The slider base 113 supports the arm holder 112 in an axially rotatable manner along an arrow G. Respective ends of the second supporting device 9-2 (Ω-arm) are provided with the first elevating mechanism 114 and the second elevating mechanism 115 respectively extending downward. The second X-ray generating tube 7a-2 is supported under the bottom end of the first elevating mechanism 114. The second plane detector 8-2 is supported at the bottom end of the second elevating mechanism 115. The second X-ray generating tube 7a-2 and the second plane detector 8-2 are opposed to each other on the second imaging central-axis CA2. The first elevating mechanism 114 and the second elevating mechanism 115 elevate and lower the second X-ray generating tube 7a-2 and the second plane detector 8-2 upward and downward along an arrow H while keeping the opposition. The slider base 113 is supported in a movable manner in crisscrossing directions by being engaged to a running rail (omitted in the figure) provided on the ceiling surface. The arm holder 112 and the slider base 113 are included in a second supporting device supporting mechanism that supports the second supporting device 9-2 (Ω-arm) in a rotatable manner.

The not-shown couch supports the top plate 116 in a liftable and lowerable manner with respect to the upward-downward direction H, and in a slidable manner in a direction I that is parallel to a longitudinal-axis direction Z of the top plate 116, and a direction J that is parallel to a transverse-axis direction X of the top plate 116.

The first imaging central-axis CA1 of the first X-ray imaging system and the second imaging central-axis CA2 of the second X-ray imaging system intersect each other at the iso center. A position of the first X-ray imaging system when the first imaging central-axis CA1 passes through the iso center is referred to as the imaging position of the first X-ray imaging system, and similarly, a position of the second X-ray imaging system when the second imaging central-axis CA2 passes through the iso center is referred to as the imaging position of the second X-ray imaging system. When the both systems are located at the respective imaging positions, such state is referred to as two-directional imaging positions.

The first X-ray imaging system and the second X-ray imaging system according to such configurations carry out imaging operation by being controlled on movement by the mechanism control unit 3, which is not shown, so as to match up, for example, an intersection point of the first imaging central-axis CA1 and the second imaging central-axis CA2 with a region of interest of the subject, where the first imaging central-axis CA1 corresponding to the first X-ray generating tube 7a-1 and the first plane detector 8-1, and the second imaging central-axis CA2 corresponding to the second X-ray generating tube 7a-2 and the second plane detector 8-2.

Then, a configuration of the X-ray diagnosis apparatus according to the second embodiment is explained below with reference to FIG. 7. FIG. 7 is a functional block diagram of a configuration of the X-ray diagnosis apparatus according to the second embodiment. Specific operation of each unit will be described in detail when explaining a process procedure.

The X-ray diagnosis apparatus 100 according to the second embodiment that has an appearance as shown in FIG. 6 includes the operation unit 1, the system control unit 2, the mechanism control unit 3, the mechanism-state monitoring unit 4, the mechanism-control input-value calculating unit 5, the user interface 6, the X-ray generating unit 7, the plane detector 8, the supporting device 9, the couch 10, the image database 11, the reconstruction processing unit 12, the image-computation/storage unit 20, and the region-of-interest coordinate estimating unit 30, as shown in FIG. 7.

The operation unit 1 includes a mouse, a key board, a button, a track ball, a joy stick, and the like, for the operator, such as a doctor or an engineer, who operates the X-ray diagnosis apparatus 100, to input various commands, and transfers a command received from the operator to the system control unit 2.

The system control unit 2 controls operation of the whole of the X-ray diagnosis apparatus 100. Precisely, the system control unit 2 performs rotation and movement control on the supporting device 9, movement control on the couch 10, adjustment of X-ray dosage, and ON/OFF control of X-ray radiation by controlling the mechanism control unit 3 and the X-ray generating unit 7 based on a command from the operator transferred from the operation unit 1.

Moreover, the system control unit 2 provides control so as to display image data stored by the image database 11, image data processed through image processing by the image-computation/storage unit 20, a Graphical User Interface (GUI) for receiving a command from the operator, and the like, onto the display unit 24, by controlling the image-computation/storage unit 20 based on a command from the operator.

The mechanism control unit 3 controls rotation and movement of the supporting device 9, movement of the couch 10, and a diaphragm of the X-ray beam-limiting device 7b. Specifically, the mechanism control unit 3 controls the supporting device 9, the couch 10, and/or the X-ray beam-limiting device 7b in accordance with an amount of control calculated by the mechanism-control input-value calculating unit 5.

The mechanism-state monitoring unit 4 acquires current state information about the supporting device 9 and the couch (for example, the angle of the supporting device 9) from the mechanism control unit 3.

The mechanism-control input-value calculating unit 5 calculates an amount of control to be used for control of the supporting device 9 and/or the couch 10 by using region-of-interest coordinates.

The user interface 6 receives from the operator a selection instruction to select a certain intersection point as region-ofinterest coordinates, when a plurality of intersection points is calculated as region-of-interest coordinate candidates.

The X-ray generating unit 7 includes the X-ray generating tube 7a and the X-ray beam-limiting device 7b. The X-ray generating tube 7a (the first X-ray generating tube 7a-1 and the second X-ray generating tube 7a-2) generates an X-ray by using a high voltage. The X-ray beam-limiting device 7b (the first X-ray beam-limiting device 7b-1, and the second X-ray beam-limiting device 7b-2) limits X-rays generated by the X-ray generating tube 7a so as to be selectively radiated onto a region of interest of the subject P. For example, the X-ray beam-limiting device 7b includes four slidable diaphragm blades, and causes X-rays generated by the X-ray generating tube 7a to be limited and radiated onto the subject P by sliding the diaphragm blades.

The plane detectors 8 (the first plane detector 8-1 and the second plane detector 8-2) is a device in which X-ray detecting elements for detecting an X-ray passed through the subject P are arranged in a matrix, and each of the X-ray detecting elements converts an X-ray passed through the subject P into an electric signal and stores it, and transmits the stored electric signal to the image-data storage circuit 21, which will be described later.

The supporting device 9 (the first supporting device 9-1 and the second supporting device 9-2) is an arm that supports the X-ray generating tube 7a, the X-ray beam-limiting device 7b, and the plane detector 8, so that the X-ray generating tube 7a and the X-ray beam-limiting device 7b, and the plane detector 8 are arranged with the supporting device 9 on opposite sides of the subject P.

The couch 10 is a bed on which the subject P is to be placed.

The image database 11 stores therein image data processed through image processing by the image-computation/storage unit 20, image data reconstructed by the reconstruction processing unit 12, image data imaged by the X-ray diagnosis apparatus 100, and the like. The image data stored by the image database 11 is also processed through display and image processing by the image-computation/storage unit 20.

The reconstruction processing unit 12 performs reconstruction processing on raw data stored by the image-data storage circuit 21 based on an instruction from the operator received via the operation unit 1, and creates three-dimensional reconstruction image.

The image-computation/storage unit 20 performs display, storage, and image processing of image data imaged by the X-ray diagnosis apparatus 100. Specifically, the image-computation/storage unit 20 includes the image-data storage circuit 21, the display-image changing unit 22, the display-image creating unit 23, and the display unit 24. The image-data storage circuit 21 stores therein raw data detected by the plane detector 8. The display-image changing unit 22 calculates a value required to change a virtual radioscopic image based on present state information received from the mechanism-state monitoring unit 4 about the angle of the supporting device 9, the position of the supporting device 9, the position of the couch 10, the height of the couch 10, the scale of image enlargement, the X-ray beam-limiting device 7b, and a compensating filter. The display-image creating unit 23 creates a two-dimensional virtual radioscopic image from three-dimensional medical image data. The display unit 24 displays a GUI for receiving a command from the operator via the operation unit 1, image data stored by the image database 11, image data processed through image processing by the display-image creating unit 23 and the display-image changing unit 22, and the like.

The region-of-interest coordinate estimating unit 30 estimates region-of-interest coordinates indicating the center of a region of interest of the subject P from three-dimensional image data of rendering the region of interest. Specifically, the region-of-interest coordinate estimating unit 30 includes the intersection-point computing unit 31, the memory 32, the intersection-region computing unit 33, and the region-of-interest coordinate determining unit 34. The intersection-point computing unit 31 estimates region-of-interest coordinates (or calculates an intersection point to be a candidate of region-of-interest coordinates) by calculating the central axis that connects the image reception area of the plane detector 8, the focus point of the X-ray generating tube 7a, and the iso center, and calculating the center point with respect to an aggregation of pixels continuously present on the central axis. The memory 32 stores therein region-of-interest coordinates estimated by the intersection-point computing unit 31. When a plurality of intersection points is calculated by the intersection-point computing unit 31, the intersection-region computing unit 33 calculates an intersection region required for selecting as region-of-interest coordinates (the volume of a region that has pixel values within a certain range from an intersection point, a distance between the intersection point and the end point on the central axis on the side of the plane detector 8, and the like). The region-of-interest coordinate determining unit 34 determines region-of-interest coordinates from among a plurality of intersection points by using an intersection region calculated by the intersection-region computing unit 33.

Figure 8A:
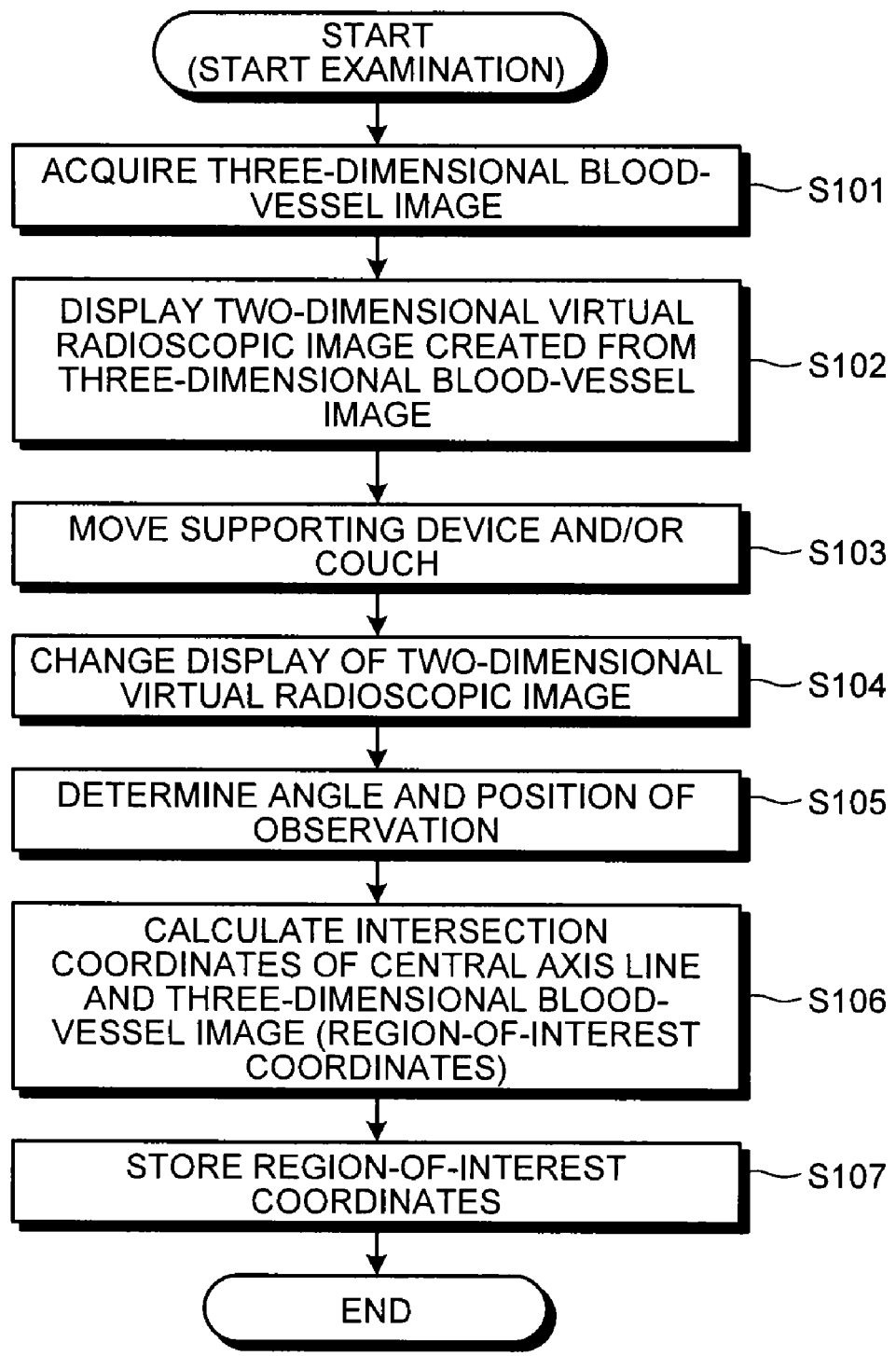
FIGS. 8A and 8B are flowcharts of process procedures during an examination performed by the X-ray diagnosis apparatus according to the second embodiment.
Figure 8B:
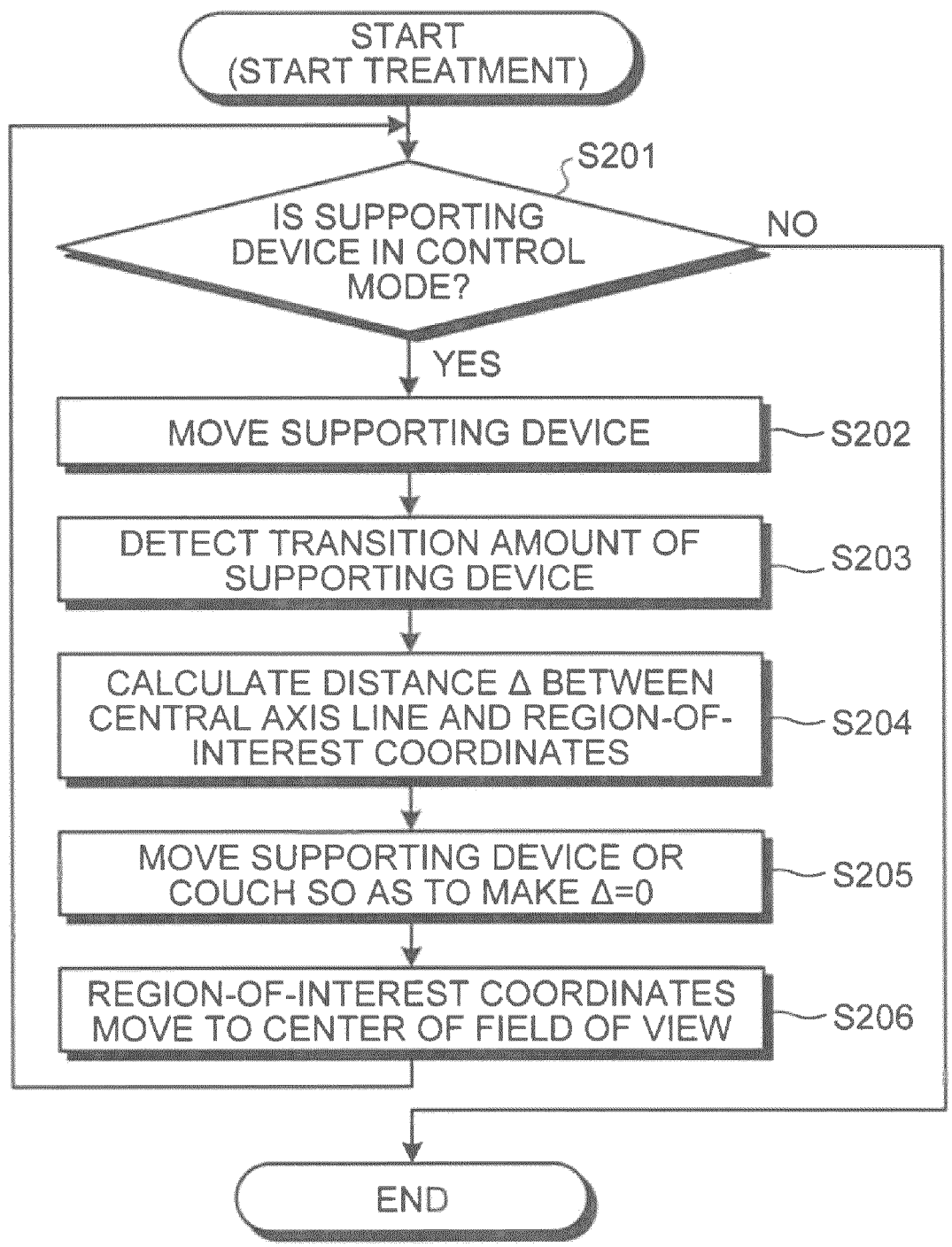
Figure 9A:
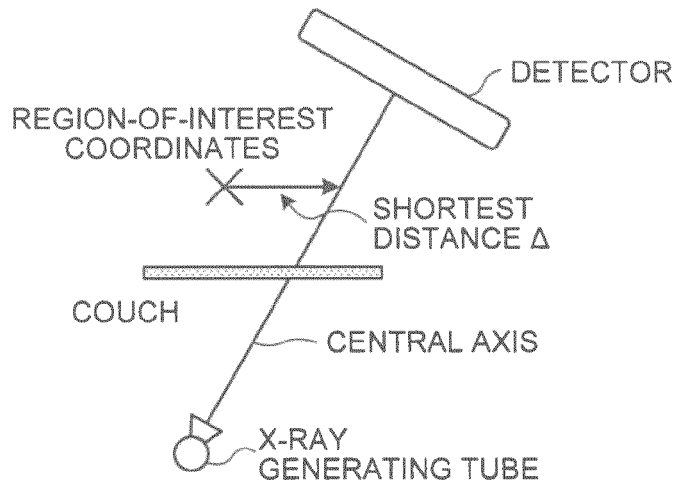
FIGS. 9A to 9C are schematic diagrams for explaining a distance between a central axis line and region-of-interest coordinates.
Figure 9B:
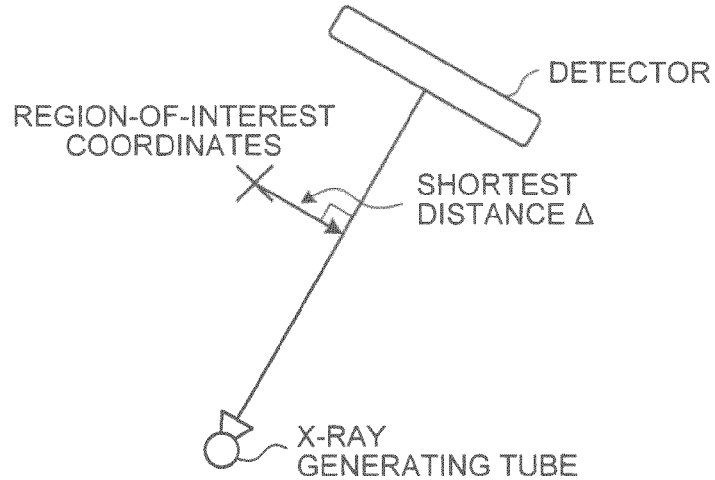
Figure 9C:
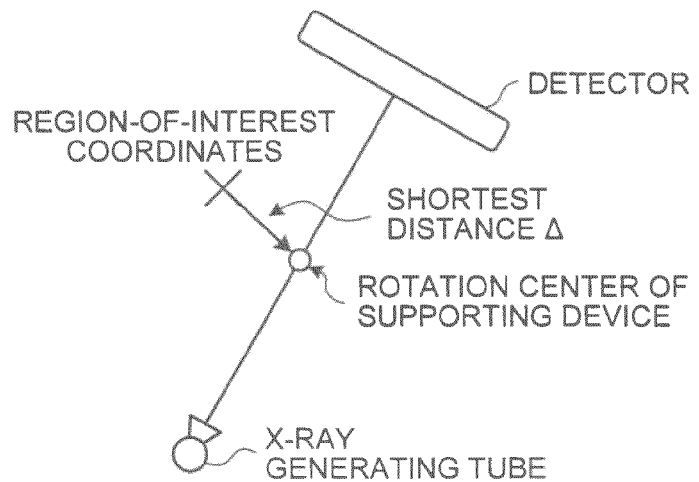

Process procedures by the X-ray diagnosis apparatus according to the second embodiment are explained below with reference to FIGS. 8A to 9C. FIG. 8A is a flowchart of a process procedure during an examination performed by the X-ray diagnosis apparatus according to the second embodiment; and FIG. 8B is a flowchart of a process procedure during a treatment performed by the X-ray diagnosis apparatus according to the second embodiment. FIGS. 9A to 9C are schematic diagrams for explaining a distance between the central axis line and region-of-interest coordinates. The following description explains a coil embolization that is an intervention treatment for a head aneurysm, as an example.

As shown in FIG. 8A, when an examination is started, to begin with, the X-ray diagnosis apparatus 100 rotationally images a head of the subject P, and acquires three-dimensional blood-vessel image data (Step S101). For example, when raw data acquired by the plane detector 8 is stored in the image-data storage circuit 21, the reconstruction processing unit 12 performs reconstruction processing, and stores reconstructed three-dimensional blood-vessel image data into the image database 11.

The X-ray diagnosis apparatus 100 then displays the three-dimensional blood-vessel image data (Step S102). For example, the display-image creating unit 23 reads the three-dimensional blood-vessel image data from the image database 11, creates a display image of rendering a blood-vessel image in a two-dimensional space, and displays the created display image onto the display unit 24.

Subsequently, the doctor moves the supporting device 9 and/or the couch 10 (Step S103). For example, after checking a state of the shape and the position of an aneurysm, the doctor moves the supporting device 9 and/or the couch 10 by using the operation unit 1 such that a region of interest comes to the center of the field of view (the center of the image reception area). When the supporting device 9 and/or the couch 10 is moved by being operated by the doctor, a transition amount of the movement is acquired by the mechanism-state monitoring unit 4, and sent to the display-image changing unit 22. When the doctor moves the supporting device 9 and/or the couch 10 at Step S103, the X-ray diagnosis apparatus 100 can be configured to display a target marker indicating the center of the field of view onto the display unit 24.

The X-ray diagnosis apparatus 100 then changes the display of the three-dimensional blood-vessel image data (Step S104). For example, the display-image changing unit 22 changes the display angle, the position, the scale of enlargement, and the like, of the three-dimensional blood-vessel image data based on the transition amount of the supporting device 9 and/or the couch 10 sent from the mechanism-state monitoring unit 4, changes the three-dimensional blood-vessel image data as like observing it in current geometrical positional relation of the supporting device 9 and the couch 10, and displays it onto the display unit 24. In other words, the X-ray diagnosis apparatus 100 virtually creates three-dimensional blood-vessel image data in accordance with operation by the doctor, creates a display image in a two-dimensional space from the virtually created three-dimensional blood-vessel image data, and displays it onto the display unit 24, meanwhile X-ray has not been radiated onto the subject P.

After accordingly determining the angle and the position of observation, the doctor presses a confirmation button included in the operation unit 1 (Step S105). This means that a region of interest is specified with respect to the display image in a two-dimensional space. Because the doctor moves the supporting device 9 and/or the couch 10 such that the region of interest comes to the center of the field of view, it is considered that the three-dimensional blood-vessel image data virtually created at that time is supposed to include the region of interest positioned at a substantial center. For this reason, the X-ray diagnosis apparatus 100 according to the first embodiment estimates region-of-interest coordinates by using the three-dimensional blood-vessel image data as explained below.

Precisely, subsequently to Step S105, the X-ray diagnosis apparatus 100 calculates intersection coordinates of the central axis line and the three-dimensional blood-vessel image data (region-of-interest coordinates) (Step S106). For example, the intersection-point computing unit 31 acquires current state information about the supporting device 9 from the mechanism-state monitoring unit 4 at first, and calculates a central axis line. The central axis line is a line that connects the center of the image reception area of the plane detector 8, the focus point of the X-ray generating tube 7$a$, and a fixed point called the iso center. The intersection-point computing unit 31 then acquires three-dimensional blood-vessel image data from the display-image changing unit 22, and calculates a section that has a pixel value on the central axis line. For example, the intersection-point computing unit 31 calculates a section having a certain pixel value (which means, for example, having a pixel value supposed to be included when a region of interest or a blood vessel is rendered, and hereinafter, simply referred to as "having a pixel value", or "including a pixel value"). The intersection-point computing unit 31 then calculates a midpoint of the section, and determines that the calculated midpoint is an intersection point.

At that time, if an aneurysm and a normal blood vessel are present, for example, on the central axis line, there is a possibility that a plurality of intersection points is present. A method of determining an aneurysm in such case is explained below. To begin with, a length d_n of a section having a pixel value within a certain range on the central axis line (the length d_n is shown in FIG. 5A). Because an aneurysm is usually a swollen blood-vessel wall that is inflated like a balloon, by using a characteristic that it has a larger blood-vessel diameter than a normal blood-vessel diameter, it can be determined that an intersection point having the largest length from among a plurality of d_n is the intersection point of an aneurysm.

The X-ray diagnosis apparatus 100 then stores region-of-interest coordinates (Step S107). For example, the intersection-point computing unit 31 stores the intersection point calculated at Step S106 into the memory 32 as region-of-interest coordinates.

Then, when a treatment is started, the doctor moves the supporting device 9 and changes the observation angle during the coiling treatment in order to confirm an embolization state of the coil. At that time, if the region of interest is not in the rotation center of the supporting device 9, the region of interest is dislocated from the field of view.

Therefore, as shown in FIG. 8B, to begin with, the X-ray diagnosis apparatus 100 determines whether the supporting device 9 is in a control mode (Step S201). For example, the mechanism-state monitoring unit 4 determines whether the supporting device 9 is in the control mode.

If the supporting device 9 is in the control mode (Yes at Step S201), the supporting device 9 moves (Step S202), and the X-ray diagnosis apparatus 100 detects a transition amount of the supporting device 9 (Step S203). For example, the mechanism-state monitoring unit 4 detects a transition amount of the supporting device 9, and calculates a current angle of the supporting device 9.

The X-ray diagnosis apparatus 100 then calculates a distance $\Delta$ between the central axis line and the region-of-interest coordinates (Step S204). For example, the mechanism-control input-value calculating unit 5 acquires current state information about the supporting device 9 from the mechanism-state monitoring unit 4, and calculates a central axis line. Moreover, the mechanism-control input-value calculating unit 5 reads the region-of-interest coordinates from the memory 32, and acquires current state information about the couch 10 from the mechanism-state monitoring unit 4. The mechanism-control input-value calculating unit 5 then calculates the distance $\Delta$ in the direction parallel to the couch 10 as shown in FIG. 9A as the shortest distance from the region-of-interest coordinates to the central axis line. Furthermore, the mechanism-control input-value calculating unit 5 calculates an amount of control of the supporting device 9 and/or the couch 10 in order to make the distance $\Delta=0$.

The shortest distance from the region-of-interest coordinates to the central axis line is not limited to the distance $\Delta$ in the direction parallel to the couch 10 as shown in FIG. 9A, and, for example, can be the distance $\Delta$ on the normal line pulling down from the region-of-interest coordinates to the central axis line as shown in FIG. 9B, or alternatively, can be the distance $\Delta$ connecting the region-of-interest coordinates and the rotation center (the iso center IC) of the supporting device 9 on the central axis line as shown in FIG. 9C.

Subsequently, the X-ray diagnosis apparatus 100 moves the supporting device 9 and/or the couch 10 so as to make the distance $\Delta=0$ (Step S205). For example, the mechanism control unit 3 reads an amount of control of the supporting device 9 and/or the couch 10 from the mechanism-control input-value calculating unit 5, and moves the supporting device 9 and/or the couch 10 in accordance with the amount of control.

The region of interest then moves to the center of the field of view (Step S206). In other words, as a result of that the supporting device 9 and/or the couch 10 is moved at Step S205, the region of interest moves to the center of the field of view on the display unit 24.

Accordingly, the doctor can constantly capture the region of interest in the center of the field of view, and saves time and effort for manually adjusting the X-ray diagnosis apparatus, thereby improving operation efficiency. Consequently, a time of imaging irrelevant to the essence of a treatment is shortened, and exposure to radiation can be also reduced.

The X-ray diagnosis apparatus 100 according to the second embodiment extracts a region of a certain range from estimated region-of-interest coordinates, from three-dimensional medical image data, and creates a display image by using only the extracted region.

Figure 10:
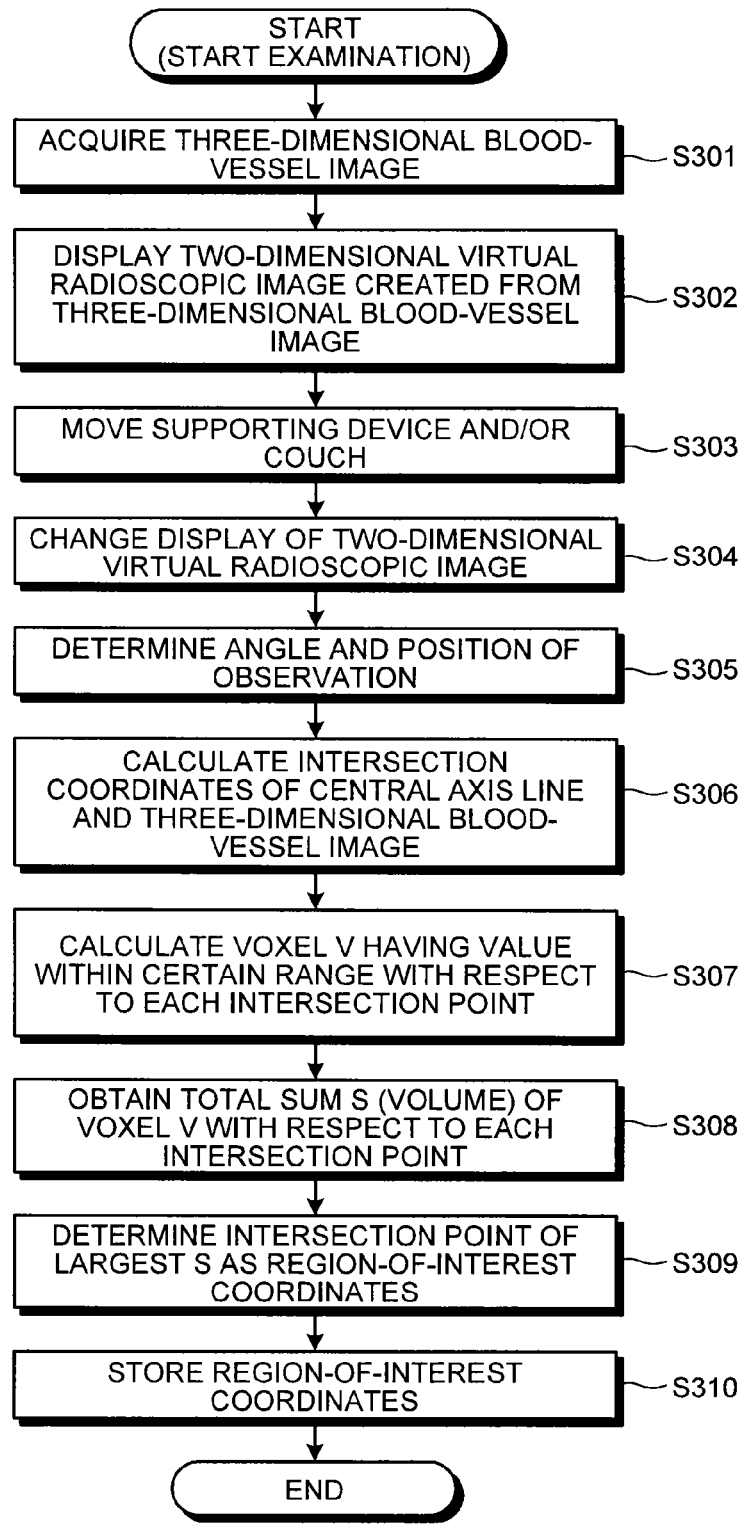
FIG. 10 is a flowchart of a process procedure during an examination performed by an X-ray diagnosis apparatus according to a modification 2-1 of the second embodiment.

Although it is assumed in the above case that an intersection point calculated at Step S106 is one, a case of a plurality of intersection points can be assumed. In such case, it may be sometimes difficult to determine region-of-interest coordinates in some cases. Therefore, a method of estimating region-of-interest coordinates when particularly assuming presence of a plurality of intersection points is explained below as a modification 2-1 of the second embodiment. FIG. 10 is a flowchart of a process procedure during an examination performed by an X-ray diagnosis apparatus according to the modification 2-1.

For example, an aneurysm that is a treatment subject of a head aneurysm has a volume compared with other blood vessels. Therefore, according to the modification 2-1, the volume of a region that has a pixel value within a specific range from an intersection point is calculated with respect to each of intersection points, and it is determined that coordinates of an intersection point of the largest volume are region-of-interest coordinates. As a result, even when there is a plurality of intersection points, region-of-interest coordinates can be correctly selected. Steps S301 to S305 in FIG. 10 are the same as Steps S101 to S105 in FIG. 8A, therefore a process procedure afterward is described below.

To begin with, the X-ray diagnosis apparatus 100 calculates intersection coordinates of the central axis line and the three-dimensional blood-vessel image data (Step S306). For example, the intersection-point computing unit 31 acquires current state information about the supporting device 9 from the mechanism-state monitoring unit 4 at first, and calculates a central axis line. The intersection-point computing unit 31 then acquires the three-dimensional blood-vessel image data from the display-image changing unit 22, and calculates a section that continuously has a pixel value on the central axis line. The intersection-point computing unit 31 then calculates a midpoint of the section, and determines that the calculated midpoint is an intersection point. When there are a number of sections, the intersection-point computing unit 31 calculates a midpoint with respect to each of the sections as an intersection point C_n.

The X-ray diagnosis apparatus 100 then calculates a voxel V that has a pixel value within a certain range with respect to each intersection point (Step S307). For example, the intersection-region computing unit 33 reads the three-dimensional blood-vessel image data and each intersection point C_n from the intersection-point computing unit 31, and calculates a voxel V_n that has a pixel value within a range R that is preliminarily set by a user. It is assumed in this example that the range R is the radius of a spherical region having the center at an intersection point C_n, for example, five millimeters as a standard. As the range R, ½ of the length d_n of a section having a pixel value within a certain range on the central axis line can be used.

The X-ray diagnosis apparatus 100 then obtains a total sum S (volume) of voxel V with respect to each intersection point (Step S308). For example, the intersection-region computing unit 33 calculates a total volume S_n of the voxel V_n with respect to each intersection point C_n. However, when using the length d_n of the intersection-point section as the range R, it is assumed that S_n is a value divided by a value of the third power of d_n.

Subsequently, the X-ray diagnosis apparatus 100 determines an intersection point of the largest value in volume as region-of-interest coordinates (Step S309). For example, the region-of-interest coordinate determining unit 34 acquires S_n from the intersection-region computing unit 33, and stores an intersection point having the largest value of S into the memory 32 as region-of-interest coordinates (Step S310). In other words, it uses a fact that an aneurysm as a treatment subject generally has a large volume compared with the other blood vessels.

As a result, even when there is a plurality of intersection points, region-of-interest coordinates can be correctly selected.

As a method of estimating region-of-interest coordinates when assuming presence of a plurality of intersection points, a modification 2-2 of the second embodiment is explained below. FIG. 11 is a flowchart of a process procedure during an examination performed by an X-ray diagnosis apparatus according to the modification 2-2.

When a doctor determines the observation angle of an aneurysm of a treatment subject, it is considered that the observation angle is generally selected such that the other blood vessels do not overlap the aneurysm as a region of interest in the direction of the plane detector 8. Therefore, it is assumed in the modification 2-2 that region-of-interest coordinates are coordinates of an intersection point at the shortest distance from the plane detector 8. As a result, even when there is a plurality of intersection points, region-of-interest coordinates can be correctly selected. Steps S401 to S405 in FIG. 11 are the same as Steps S101 to S105 in FIG. 8A, therefore a process procedure afterward is described below.

To begin with, the X-ray diagnosis apparatus 100 calculates intersection coordinates of the central axis line and the three-dimensional blood-vessel image data (Step S406). For example, the intersection-point computing unit 31 acquires current state information about the supporting device 9 from the mechanism-state monitoring unit 4 at first, and calculates a central axis line. The intersection-point computing unit 31 then acquires the three-dimensional blood-vessel image data from the display-image changing unit 22, and calculates a section that has a pixel value on the central axis line. The intersection-point computing unit 31 then calculates a midpoint of the section, and determines that the calculated midpoint is an intersection point. When there are a number of sections, the intersection-point computing unit 31 calculates a midpoint with respect to each of the sections as an intersection point C_n.

The X-ray diagnosis apparatus 100 then calculates a distance d from the plane detector 8 with respect to each intersection point (Step S407). For example, the intersection-region computing unit 33 reads the three-dimensional blood-vessel image data and each intersection point C_n from the intersection-point computing unit 31, and calculates a distance d between the end point of the central axis line on the side of the plane detector 8 and the intersection point C_n.

The X-ray diagnosis apparatus 100 then determines that an intersection point of the smallest value of the distance value is region-of-interest coordinates (Step S408). For example, the region-of-interest coordinate determining unit 34 acquires d from the intersection-region computing unit 33, and stores an intersection point having the smallest value of d into the memory 32 as region-of-interest coordinates (Step S409). In other words, it uses a practice that when determining the observation angle of an aneurysm of a treatment subject, the doctor generally selects an observation angle such that the other blood vessels do not overlap the aneurysm as a region of interest in the direction of the plane detector.

As a result, even when there is a plurality of intersection points, region-of-interest coordinates can be correctly selected.

The modification 2-1 and the modification 2-2 are explained above about the methods of determining region-of-interest coordinates from among a plurality of intersection points; however, if a region of interest has poor characteristics, determination is sometimes difficult in some cases. Therefore, according to a modification 2-3 of the second embodiment, when there is a plurality of intersection points, intersection regions are displayed in different colors, thereby allowing the user to select one. FIG. 12 is a flowchart of a process procedure during an examination performed by an X-ray diagnosis apparatus according to the modification 2-3.

As a result, even when there is a plurality of intersection points, and a region of interest has poor characteristics, region-of-interest coordinates can be correctly selected. Steps S501 to S505 in FIG. 12 are the same as Steps S101 to S105 in FIG. 8A, therefore a process procedure afterward is described below.

To begin with, the X-ray diagnosis apparatus 100 calculates intersection coordinates of the central axis line and the three-dimensional blood-vessel image data (Step S506). For example, the intersection-point computing unit 31 acquires current state information about the supporting device 9 from the mechanism-state monitoring unit 4 at first, and calculates a central axis line. The intersection-point computing unit 31 then acquires the three-dimensional blood-vessel image data from the display-image changing unit 22, and calculates a section that has a pixel value on the central axis line. The intersection-point computing unit 31 then calculates a midpoint of the section, and determines that the calculated midpoint is an intersection point. When there are a number of sections, the intersection-point computing unit 31 calculates a midpoint with respect to each of the sections as an intersection point C_n.

The X-ray diagnosis apparatus 100 then calculates a voxel V that has a pixel value within a certain range with respect to each intersection point (Step S507). For example, the intersection-region computing unit 33 reads the three-dimensional blood-vessel image data and each intersection point C_n from the intersection-point computing unit 31, and calculates a voxel V_n that has a pixel value within the range R that is preliminarily set by a user. It is assumed in this example that the range R is, for example, five millimeters as a standard.

The X-ray diagnosis apparatus 100 then differentiates the color of the voxel V_n of each intersection point from regions other than the intersection points, and displays it in different color (Step S508). For example, the region-of-interest coordinate determining unit 34 reads the three-dimensional blood-vessel image data and the voxel V_n from the intersection-region computing unit 33, assigns the voxel V_n a display color different from the other voxels, and displays it onto the display unit 24. The display color assigned to each V_n can be the same color.

Subsequently, the user performs a selecting operation of an intersection point (Step S509). For example, the user inputs a signal to select an intersection point into the region-of-interest coordinate determining unit 34 via the user interface 6, such as a lever.

The X-ray diagnosis apparatus 100 then displays the voxel V of the selected intersection point by changing its color (Step S510). For example, the region-of-interest coordinate determining unit 34 assigns a display color having good visibility and meaning that it is selected to the voxel V_n selected by the user, and displays it onto the display unit 24. The user can confirm on the display unit 24 that the currently selected region of interest is displayed in color different from the color of the other region-of-interest candidates.

The user repeats Step S509, and determines an intersection point to be region-of-interest coordinates (Step S511). For example, the user inputs a determination signal into the region-of-interest coordinate determining unit 34 via the user interface 6.

The X-ray diagnosis apparatus 100 then stores the region-of-interest coordinates (Step S512). For example, the region-of-interest coordinate determining unit 34 stores the intersection point C_n determined at Step S511 into the memory 32 as region-of-interest coordinates.

As a result, even when there is a plurality of intersection points, region-of-interest coordinates can be correctly selected.

Although the voxel V_n is displayed in different color according to the modification 2-3, it can be configured such that, for example, each voxel V_n is displayed by sequentially assigning it an identifier like a serial number, and then the user specifies the number. Therefore, according to a modification 2-4 of the second embodiment, when there is a plurality of intersection points, an identifier is sequentially assigned to each of the intersection points and then it is displayed, thereby allowing the user to select one. FIG. 13 is a flowchart of a process procedure during an examination performed by an X-ray diagnosis apparatus according to the modification 2-4.

As a result, even when there is a plurality of intersection points, and a region of interest has poor characteristics, region-of-interest coordinates can be correctly selected. Steps S601 to S605 in FIG. 13 are the same as Steps S101 to S105 in FIG. 8A, therefore a process procedure afterward is described below.

To begin with, the X-ray diagnosis apparatus 100 calculates intersection coordinates of the central axis line and the three-dimensional blood-vessel image data (Step S606). For example, the intersection-point computing unit 31 acquires current state information about the supporting device 9 from the mechanism-state monitoring unit 4 at first, and calculates a central axis line. The intersection-point computing unit 31 then acquires the three-dimensional blood-vessel image data from the display-image changing unit 22, and calculates a section that has a pixel value on the central axis line. The intersection-point computing unit 31 then calculates a midpoint of the section, and determines that the calculated midpoint is an intersection point. When there are a number of sections, the intersection-point computing unit 31 calculates a midpoint with respect to each of the sections as an intersection point C_n.

The X-ray diagnosis apparatus 100 then displays an identifier with respect to each intersection point (Step S607). For example, the region-of-interest coordinate determining unit 34 reads the three-dimensional blood-vessel image data and the intersection point C_n from the intersection-region computing unit 33, sequentially assigns it, for example, a serial number N, and displays it onto the display unit 24.

Subsequently, the user selects an intersection point based on the identifier (Step S608). For example, the user inputs the number N corresponding to the region of interest into the region-of-interest coordinate determining unit 34 via the user interface 6, such as a number button.

The X-ray diagnosis apparatus 100 then determines an intersection point to be region-of-interest coordinates (Step S609), and stores the region-of-interest coordinates (Step S610). For example, the region-of-interest coordinate determining unit 34 determines the intersection point C_n specified at Step S608 as region-of-interest coordinates, and stores it into the memory 32.

As a result, even when there is a plurality of intersection points, region-of-interest coordinates can be correctly selected.

As described above, according to the second embodiment, in the X-ray diagnosis apparatus 100, at first, the region-of-interest coordinate estimating unit 30 estimates region-of-interest coordinates that indicate the position of a region of interest in a three-dimensional space based on information specified about a display image. Then, the mechanism-control input-value calculating unit 5 calculates an amount of control to be used for control of the supporting device 9 and/or the couch 10 by using the region-of-interest coordinates estimated by the region-of-interest coordinate estimating unit 30. The mechanism control unit 3 then controls the supporting device 9 and/or the couch 10 in accordance with the amount of control calculated by the mechanism-control input-value calculating unit 5.

In other words, the region-of-interest coordinate estimating unit 30 estimates the position of a region of interest as region-of-interest coordinates based on pixel information about three-dimensional medical image data present on a line connecting the focus point of the X-ray generating tube and the substantial center of the detector surface. The mechanism-control input-value calculating unit 5 calculates an amount of control to be used for control of a certain device by using the region-of-interest coordinates estimated by the region-of-interest coordinate estimating unit 30. The mechanism control unit 3 controls the certain device in accordance with the amount of control calculated by the mechanism-control input-value calculating unit 5.

In this way, when the operator changes the angle and/or the position of the supporting device 9, the X-ray diagnosis apparatus 100 according to the second embodiment controls the supporting device 9 and/or the couch 10 such that the region of interest is not to be dislocated from the field of view. Accordingly, the operator can constantly capture a region of interest in the center of the field of view, and saves time and effort for manually adjusting the X-ray diagnosis apparatus 100, thereby improving operation efficiency. Consequently, a time of imaging irrelevant to the essence of a treatment is shortened, and exposure to radiation can be also reduced.

Moreover, in the X-ray diagnosis apparatus 100 according to the second embodiment, the intersection-point computing unit 31 estimates region-of-interest coordinates by calculating the central axis that connects the image reception area of the plane detector 8, the focus point of the X-ray generating tube 7a, and the iso center, and calculating the center point with respect to an aggregation of pixels continuously present on the central axis (an aggregation of pixels each having a pixel value in a certain range). In other words, the intersection-point computing unit 31 estimates region-of-interest coordinates by calculating the center point of an aggregation of pixels continuously present on the line connecting the focus point of the X-ray generating tube and the substantial center of the detector surface as an aggregation of pixels each having a value in a certain range. In this way, region-of-interest coordinates can be appropriately estimated.

Furthermore, in the X-ray diagnosis apparatus 100 according to the second embodiment, when the intersection-point computing unit 31 calculates a plurality of intersection points, the intersection-region computing unit 33 calculates the volume of a region having a pixel value within a certain range from an intersection point (a region sectioned with pixels present within a certain range from an intersection point and each having a pixel value in a certain range) with respect to each of the intersection points, and the region-of-interest coordinate determining unit 34 estimates that an intersection point of the largest value of the calculated volume is region-of-interest coordinates. Accordingly, even when there is a plurality of intersection points, region-of-interest coordinates can be correctly selected.

Moreover, according to the X-ray diagnosis apparatus 100 according to the second embodiment, when the intersection-point computing unit 31 calculates a plurality of intersection points, the intersection-region computing unit 33 calculates a distance between an intersection point and the end point on the central axis on the side of the plane detector 8 with respect to each of the intersection points, and the region-of-interest coordinate determining unit 34 estimates that an intersection point of the smallest value of the calculated distances is region-of-interest coordinates. Accordingly, even when there is a plurality of intersection points, region-of-interest coordinates can be correctly selected.

Furthermore, in the X-ray diagnosis apparatus 100 according to the second embodiment, when the intersection-point computing unit 31 calculates a plurality of intersection points, the user interface 6 receives from the operator a selection instruction to select a certain intersection point from among the intersection points. Accordingly, even when there is a plurality of intersection points, and a region of interest has poor characteristics, region-of-interest coordinates can be correctly selected.

Moreover, in the X-ray diagnosis apparatus 100 according to the second embodiment, the region-of-interest coordinate estimating unit 30 displays pixels in a region within a certain range from estimated region-of-interest coordinates and each having a pixel value in a certain range, with at least one of a color, a pattern, and a brightness different from those of the other pixels.

Furthermore, in the X-ray diagnosis apparatus 100 according to the second embodiment, when no aggregation of pixels each having a pixel value in a certain range is present on the line connecting the focus point of X-ray generating tube and the substantial center of the detector surface, the region-of-interest coordinate estimating unit 30 estimates region-of-interest coordinates by calculating the center point of an aggregation of pixels present within a certain distance range from the line that is an aggregation of pixels each having a pixel value in a certain range.

Moreover, in the X-ray diagnosis apparatus 100 according to the second embodiment, when a plurality of aggregations of pixels each having a pixel value in a certain range is present on the line connecting the focus point of the X-ray generating tube and the substantial center of the detector surface, the region-of-interest coordinate estimating unit 30 calculates respective lengths of the aggregations of pixels, and estimates region-of-interest coordinates based on the respective calculated lengths.

Furthermore, in the X-ray diagnosis apparatus 100 according to the second embodiment, when a plurality of aggregations of pixels each having a pixel value in a certain range is present on the line connecting the focus point of the X-ray generating tube and the substantial center of the detector surface, the region-of-interest coordinate estimating unit 30 calculates a length of each of the aggregations of pixels, calculates a total volume of aggregations of pixels in the certain range that are aggregations of pixels present within a spherical region having the center at the center point and a radius that is a half of the calculated length, calculates a value that the calculated total volume is divided by the third power of the radius, and estimates region-of-interest coordinates based on each of the calculated values.

Moreover, in the X-ray diagnosis apparatus 100 according to the second embodiment, when a plurality of aggregations of pixels each having a pixel value in a certain range is present on the line connecting the focus point of the X-ray generating tube and the substantial center of the detector surface, the region-of-interest coordinate estimating unit 30 displays a region within a certain range from among the aggregations in a differentiated manner with at least one of a color, a pattern, and a brightness different from those of the other aggregations. Furthermore, in the X-ray diagnosis apparatus 100 according to the second embodiment, the user interface 6 receives a selection instruction to select one from among information displayed in a differentiated manner.

Although according to the second embodiment, region-of-interest coordinates are used for control of the supporting device and the couch, in an X-ray diagnosis apparatus of the bi plane type that includes a second supporting device, region-of-interest coordinates can be used for initial positioning control of the second supporting device. Conventionally, when using an X-ray diagnosis apparatus of the bi plane type during a treatment, the operator needs to position a region of interest of the subject in the center of the field of view while manually adjusting the X-ray diagnosis apparatus. By contrast, according to a third embodiment of the present invention, manual adjustment is not required.

Figure 14A:
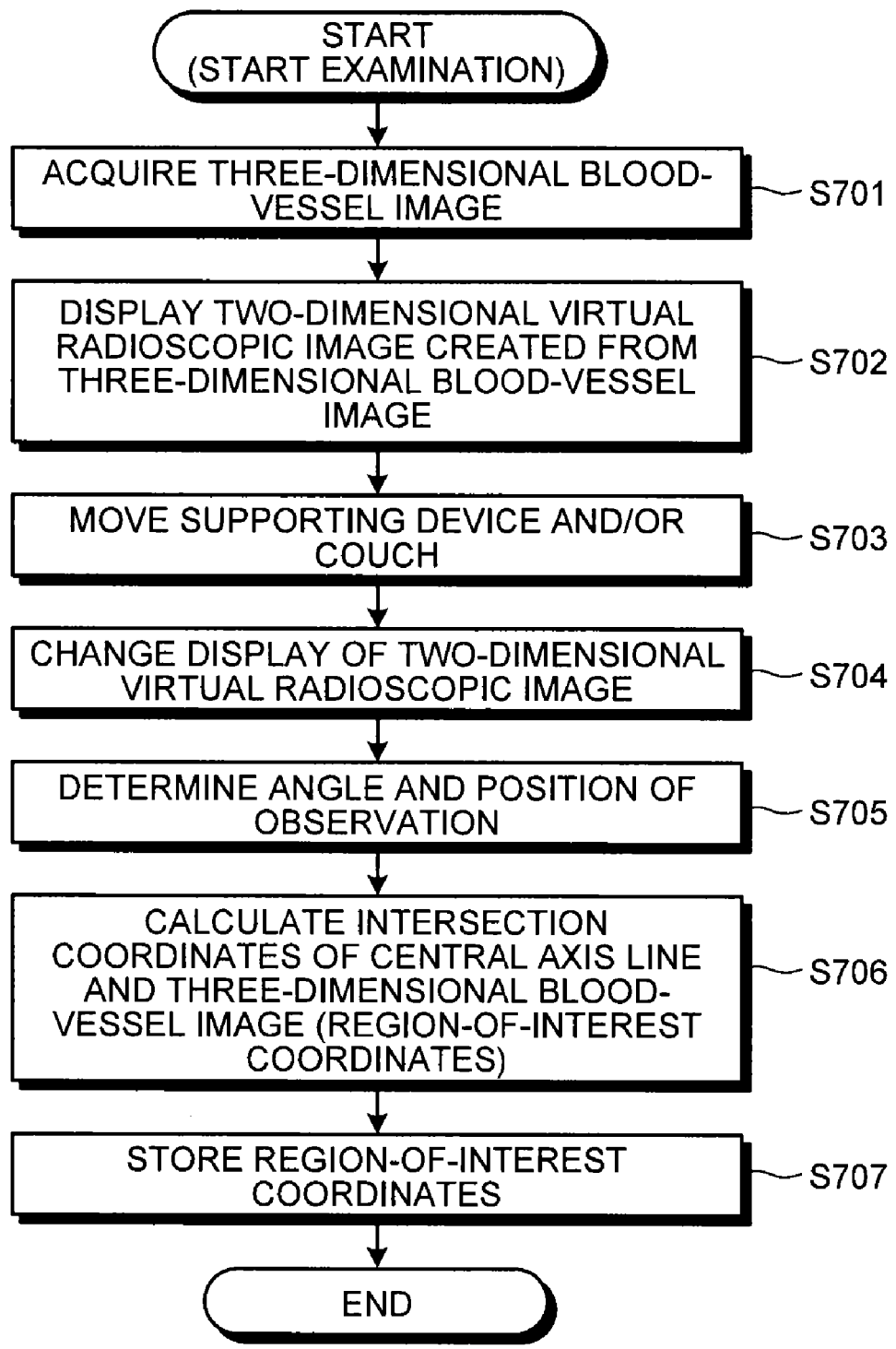

A process procedure by an X-ray diagnosis apparatus according to the third embodiment is explained below with reference to FIGS. 14A and 14B. FIG. 14A is a flowchart of a process procedure during an examination performed by the X-ray diagnosis apparatus according to the third embodiment; and FIG. 14B is a flowchart of a process procedure during a treatment performed by the X-ray diagnosis apparatus according to the third embodiment. Steps S701 to S707 in FIG. 14A are the same as Steps S101 to S107 in FIG. 8A, therefore explanations of them are omitted.

According to the third embodiment, when a treatment is started, in order to carry out an observation simultaneously from two directions, the doctor presses a setting start button of the second supporting device 9-2 via the operation unit 1.

The X-ray diagnosis apparatus 100 then starts setting of the second supporting device 9-2 as shown in FIG. 14B (Step S801).

The X-ray diagnosis apparatus 100 then calculates a distance Δ between the rotation center of the second supporting device 9-2 and the region-of-interest coordinates (Step S802). For example, the mechanism-control input-value calculating unit 5 acquires current state information about the second supporting device 9-2 from the mechanism-state monitoring unit 4, and calculates rotation center coordinates. Moreover, the mechanism-control input-value calculating unit 5 reads the region-of-interest coordinates from the memory 32. The mechanism-control input-value calculating unit 5 then calculates the shortest distance from the region-of-interest coordinates to the rotation center coordinates. Furthermore, the mechanism-control input-value calculating unit 5 calculates an amount of control of the second supporting device 9-2 to make the distance Δ=0.

Subsequently, the X-ray diagnosis apparatus 100 moves the second supporting device 9-2 so as to make the distance Δ=0 (Step S803). For example, the mechanism control unit 3 reads the amount of control of the second supporting device 9-2 from the mechanism-control input-value calculating unit 5, and moves the second supporting device 9-2 in accordance with the amount of control.

The setting of the second supporting device 9-2 is then completed (Step S804).

In this way, the doctor can save time and effort for manually adjusting the second supporting device 9-2, thereby improving operation efficiency, consequently, because the second supporting device 9-2 can be set so as to capture the region of interest in the center of the field of view without exposing the subject P to unnecessary radiation, an effect of reduction in radiation exposure can be expected.

According to the second embodiment, region-of-interest coordinates are used for control of the supporting device and the couch, and according to the third embodiment, region-of-interest coordinates are used for initial positioning control of the second supporting device; however, region-of-interest coordinates can be used for control of the diaphragm. Conventionally, if the angle and/or the position of observation is changed after the diaphragm is once inserted, it overlaps a region of interest, resulting in time and effort for manual adjustment. By contrast, according to a fourth embodiment of the present invention, manual adjustment is not required. According to the fourth embodiment, it is assumed that control of the supporting device and the couch as performed in the second embodiment is not carried out.

A process procedure by an X-ray diagnosis apparatus according to the fourth embodiment is explained below with reference to FIGS. 15A to 16D. FIG. 15A is a flowchart of a process procedure during an examination performed by the X-ray diagnosis apparatus according to the fourth embodiment; and FIG. 15B is a flowchart of a process procedure during a treatment performed by the X-ray diagnosis apparatus according to the fourth embodiment. FIGS. 16A to 16D are schematic diagram for explaining a closest distance. Steps S901 to S907 in FIG. 15A are the same as Steps S101 to S107 in FIG. 8A, therefore explanations of them are omitted.

From a point of view of reduction in unnecessary radiation exposure, sometimes the diaphragm is inserted into a part other than a region of interest in some cases. For this reason, according to the fourth embodiment, when a treatment is started, the doctor starts setting of the diaphragm (Step S1001).

The doctor then specifies an aperture range of the diaphragm (Step S1002), and subsequently selects a diaphragm control mode (Step S1003). If the diaphragm control mode is not selected (No at Step S1003), the processing is directly terminated.

By contrast, if the diaphragm control mode is selected (Yes at Step S1003), the X-ray diagnosis apparatus 100 projects the region-of-interest coordinates onto a plane on which the diaphragm is present (Step S1004). For example, the mechanism-control input-value calculating unit 5 acquires current state information about the supporting device 9 from the mechanism-state monitoring unit 4. Moreover, the mechanism-control input-value calculating unit 5 reads the region-of-interest coordinates from the memory 32. The mechanism-control input-value calculating unit 5 then obtains a straight line that connects the focus point of the X-ray generating tube 7a and the region-of-interest coordinates. The mechanism-control input-value calculating unit 5 then acquires current state information about the X-ray beam-limiting device 7b, and obtains intersection coordinates of the obtained straight line and the plane on which the diaphragm is present (see FIG. 16A).

Figure 16A:
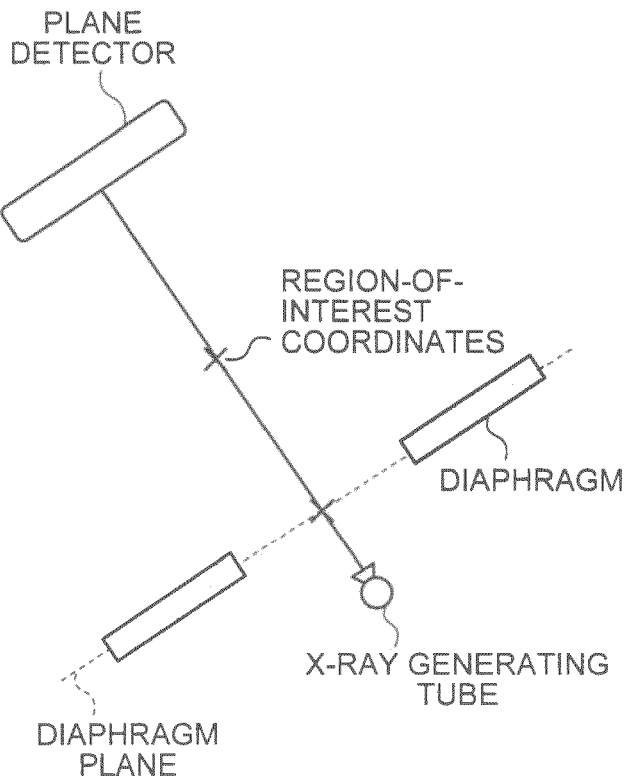
FIGS. 16A to 16D are schematic diagrams for explaining a closest distance.
Figure 16B:
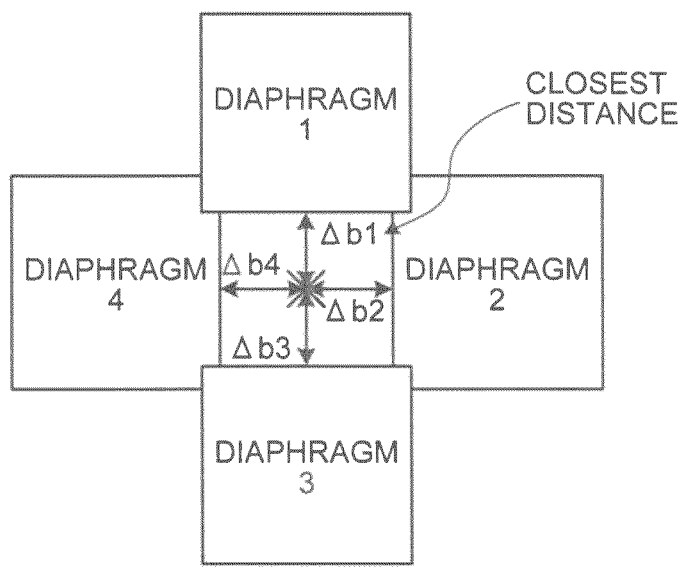
Figure 16C:
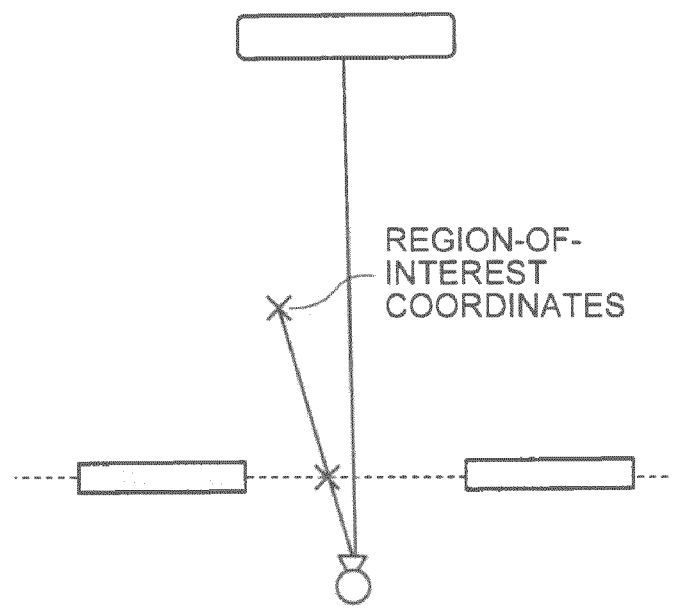

The X-ray diagnosis apparatus 100 then calculates the closest distance Δ_b between the projected point and the diaphragm (Step S1005). For example, the mechanism-control input-value calculating unit 5 calculates the closest distance Δ_bn between the intersection coordinates and the diaphragm. When there is a plurality of diaphragms, as shown in FIG. 16B, it is calculated with respect to each of the diaphragms.

The doctor moves the supporting device 9 to change the angle and/or the position of observation, then the supporting device 9 moves (Step S1006).

The X-ray diagnosis apparatus 100 then projects region-of-interest coordinates again onto the plane on which the diaphragm is present (Step S1007). For example, the mechanism-control input-value calculating unit 5 acquires current state information about the supporting device 9 from the mechanism-state monitoring unit 4. Moreover, the mechanism-control input-value calculating unit 5 reads the region-of-interest coordinates from the memory 32. The mechanism-control input-value calculating unit 5 then obtains a straight line that connects the focus point of the X-ray generating tube 7a and the region-of-interest coordinates. The mechanism-control input-value calculating unit 5 then acquires current state information about the X-ray beam-limiting device 7b, and obtains intersection coordinates of the obtained straight line and the plane on which the diaphragm is present (see FIG. 16C).

Figure 16D:
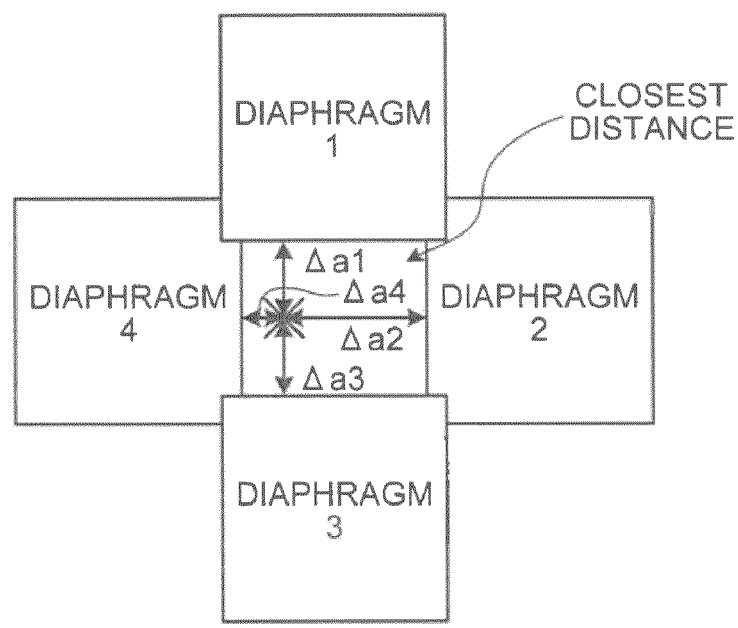

The X-ray diagnosis apparatus 100 then calculates the closest distance $\Delta\_a$ between the projected point and the diaphragm (Step S1008). For example, the mechanism-control input-value calculating unit 5 calculates the closest distance $\Delta\_an$ between the intersection coordinates and the diaphragm. When there is a plurality of diaphragms, as shown in FIG. 16D, it is calculated with respect to each of the diaphragms.

Subsequently, the X-ray diagnosis apparatus 100 moves the X-ray beam-limiting device 7b so as to make the closest distance $\Delta\_an=\Delta\_bn$ (Step S1009). For example, the mechanism-control input-value calculating unit 5 calculates an amount of control of the X-ray beam-limiting device 7b for making the closest distance $\Delta\_an=\Delta\_bn$; and the mechanism control unit 3 reads the amount of control of the X-ray beam-limiting device 7b from the mechanism-control input-value calculating unit 5, and moves the X-ray beam-limiting device 7b in accordance with the amount of control.

In this way, the X-ray diagnosis apparatus 100 repeats Step S1003 to Step S1010, until the diaphragm control mode is terminated (No at Step S1003).

The X-ray diagnosis apparatus 100 according to the third embodiment can be configured to calculate an amount of control to be used for control of the compensating filter as a certain device, and to control the compensating filter in accordance with the calculated amount of control. Moreover, the X-ray diagnosis apparatus 100 according to the third embodiment can be configured to identify a point on the X-ray detector that anatomically matches region-of-interest coordinates, and to control the X-ray beam-limiting device and/or the compensating filter so as to vary X-ray incident strengths in a region within a certain range from the identified point and the other regions. The certain range is a predetermined value or a range in which an X-ray strength distribution used in advance is to be reproduced.

In this way, the doctor does not need adjustment of the diaphragm position arising from change in the observation angle, so that reduction in the manual operation time can be expected.

Although according to the second to fourth embodiments, region-of-interest coordinates are used for control of the X-ray diagnosis apparatus, region-of-interest coordinates can be used for control of display by the image-computation/storage unit. Conventionally, even if the image-computation/storage unit displays three-dimensional image data onto a display unit, it does not always display a region of interest. For this reason, the operator manually selects a region of interest from among three-dimensional image data, and enlarges and/or turns the region of interest in order to observe the region of interest more precisely, resulting in time and effort. By contrast, according to a fifth embodiment of the present invention, neither manual selection nor manual adjustment is required.

Figure 17A:
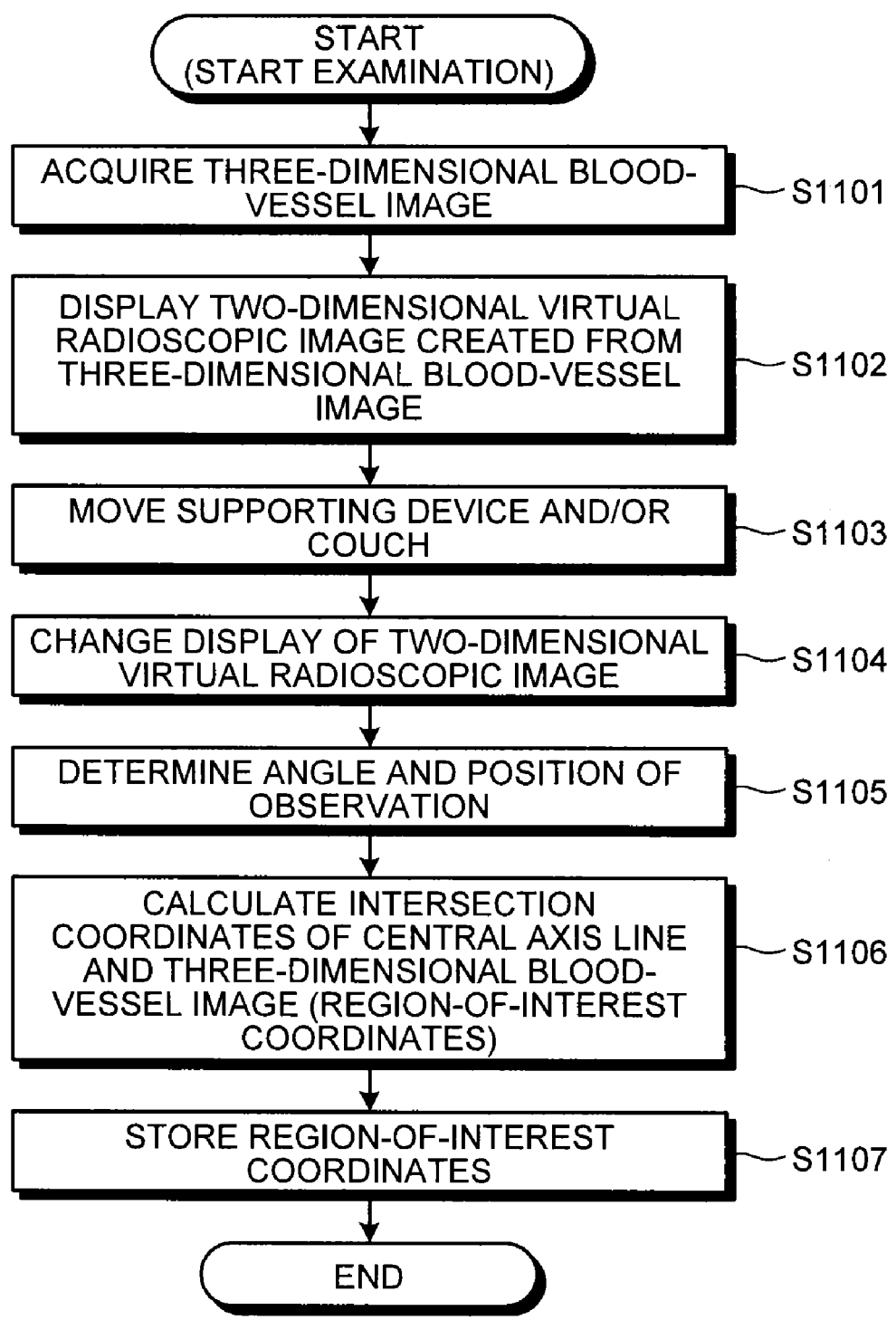
FIGS. 17A and 17B are flowcharts of process procedures during an examination performed by an X-ray diagnosis apparatus according to a fifth embodiment of the present invention.
Figure 17B:
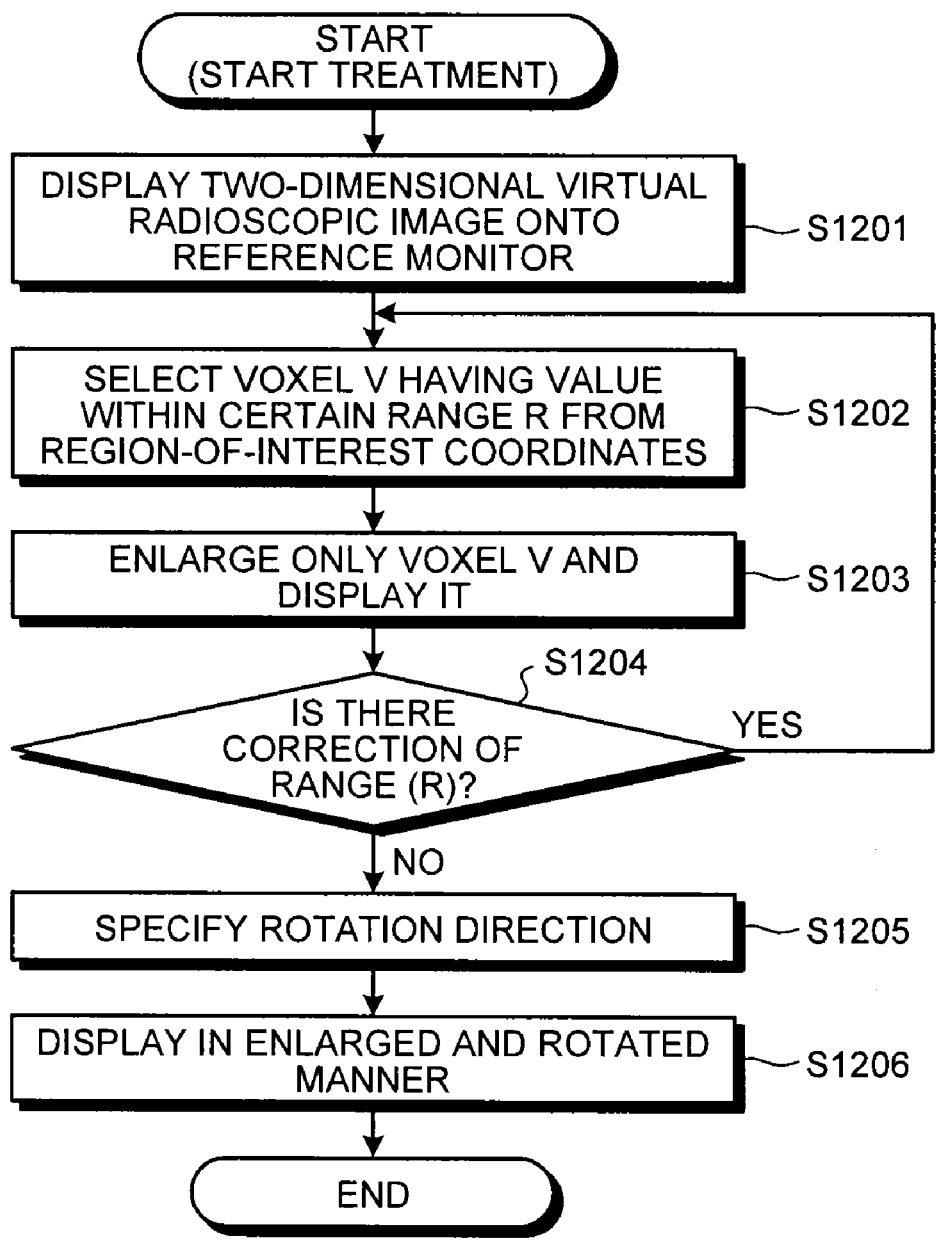

A process procedure by an X-ray diagnosis apparatus according to the fifth embodiment is explained below with reference to FIGS. 17A and 17B. FIG. 17A is a flowchart of a process procedure during an examination performed by the X-ray diagnosis apparatus according to the fifth embodiment; and FIG. 17B is a flowchart of a process procedure during a treatment performed by the X-ray diagnosis apparatus according to the fifth embodiment. Steps S1101 to S1107 in FIG. 17A are the same as Steps S101 to S107 in FIG. 8A, therefore explanations of them are omitted.

The X-ray diagnosis apparatus 100 displays the three-dimensional blood-vessel image data that is acquired during an examination onto the display unit 24 in accordance with an instruction by the operator (Step S1201).

The X-ray diagnosis apparatus 100 then selects a voxel V having a pixel value within a certain range from the region-of-interest coordinates (Step S1202). For example, the display-image changing unit 22 acquires three-dimensional blood-vessel image data from the image database 11, reads the region-of-interest coordinates from the memory 32, and then selects a voxel V having a pixel value within the range R preliminarily set by the operator. It is assumed in this example that the range R is, for example, 30 millimeters as a standard.

The X-ray diagnosis apparatus 100 then enlarges only the voxel V and displays it (Step S1203). For example, the display-image creating unit 23 enlarges only the voxel V selected at Step S1202, and displays it onto the display unit 24.

Subsequently, the X-ray diagnosis apparatus 100 determines whether correction of the range R is received (Step S1204). For example, the display-image changing unit 22 receives a correction signal that designates a correction of the range R by using the user interface 6, such as a lever.

If the correction is received (Yes at Step S1204), the X-ray diagnosis apparatus 100 again corrects the range R in accordance with the received correction signal, reselects the voxel V (Step S1202), enlarges only the reselected voxel V, and displays it onto the display unit 24.

Figure 18:
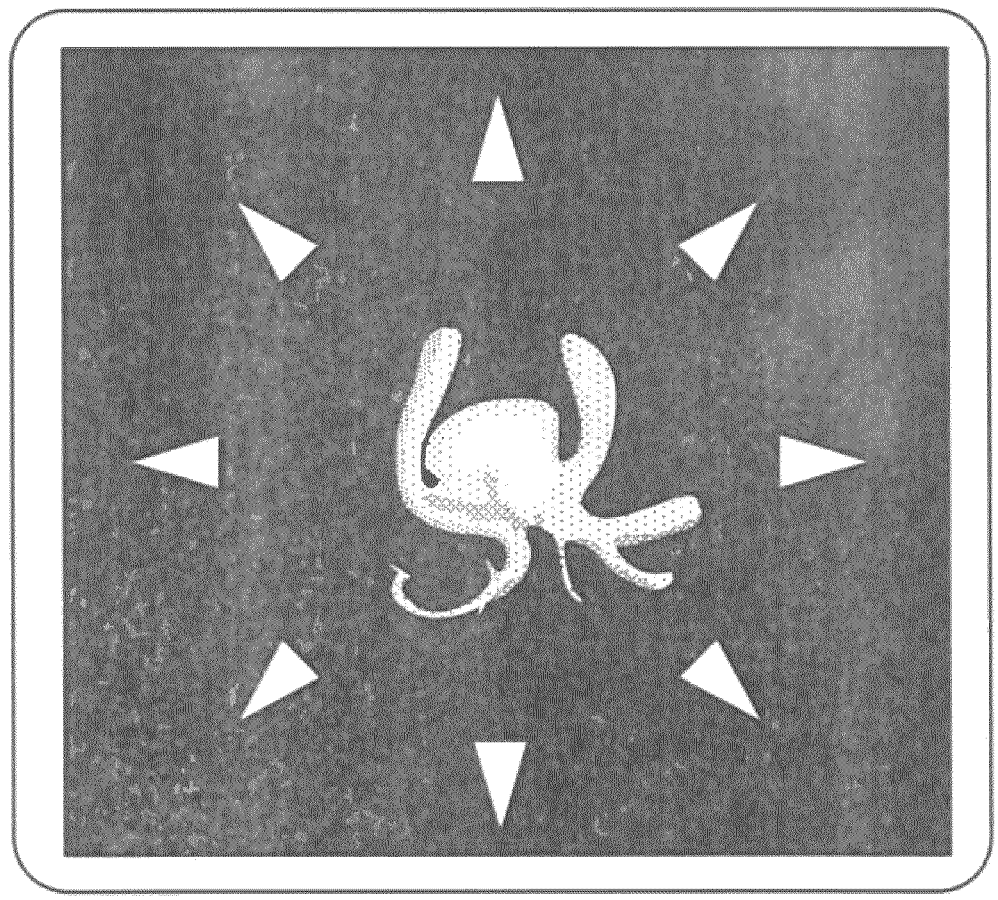
FIG. 18 is a schematic diagram for explaining a display screen of a region of interest.

By contrast, if the correction is not received (No at Step S1204), the X-ray diagnosis apparatus 100 receives designation of a rotation direction (Step S1205). For example, the display-image changing unit 22 receives designation of a rotation direction via the user interface 6 on the screen like a lever, as shown in FIG. 18. As designation of the rotation directions, it is assumed that, for example, eight directions can be selected as a standard.

The X-ray diagnosis apparatus 100 then displays an image in an enlarged and rotated manner (Step S1206). For example, the display-image changing unit 22 receives a rotation direction signal from the user interface 6, and creates rotated image data with respect to each angle preliminarily specified by the operator. The display-image creating unit 23 then receives image data from the display-image changing unit 22, and displays it onto the display unit 24.

Accordingly, the operator can display the region of interest in an enlarged and rotated manner through a simple operation, so that reduction in the manual operation time can be expected.

Although the fifth embodiment is explained above with reference to an example of image data acquired by the X-ray diagnosis apparatus, image data is not limited to this, and image data acquired by one of various modalities, such as an ultrasound diagnosis apparatus, a Computed Radiography (CR) apparatus, or a Magnetic Resonance Imaging (MRI) apparatus, can be similarly applied. In other words, for example, supposing a modality is connected to a Picture Archiving and Communication System (PACS) via a network, the modality can transmit acquired image data to a medical-image display device connected to the network. Consequently, the medical-image display device can display three-dimensional image data received from the modality onto a display unit.

Accordingly, for example, as any of the modalities estimates region-of-interest coordinates and transmits image data as well as the region-of-interest coordinates to the medical-image display device, and as the medical-image display device includes each unit corresponding to the image-computation/storage unit 20 described above, an operator who operates the medical-image display device can display a region of interest in an enlarged and rotated manner through a simple operation, so that reduction in the manual operation time can be expected. Alternatively, it can be configured such that any of the modalities transmits image data together with mechanism state information to the medical-image display device, and the medical-image display device estimates region-of-interest coordinates.

Although according to the fifth embodiment, enlarged and rotated display of image data is controlled, it can be configured to display by changing color of only a region of interest in order to improve visibility. According to a sixth embodiment of the present invention, visibility of a region of interest is improved and confirmation becomes easier, thereby bringing efficiency to manual operations, so that reduction in the manual operation time can be expected.

A process procedure by an X-ray diagnosis apparatus according to the sixth embodiment is explained below with reference to FIGS. 19A and 19B. FIG. 19A is a flowchart of a process procedure during an examination performed by the X-ray diagnosis apparatus according to the sixth embodiment; and FIG. 19B is a flowchart of a process procedure during a treatment performed by the X-ray diagnosis apparatus according to the sixth embodiment. Steps S1301 to S1307 in FIG. 19A are the same as Steps S101 to S107 in FIG. 8A, therefore explanations of them are omitted.

The X-ray diagnosis apparatus 100 displays the three-dimensional blood-vessel image data that is acquired during an examination onto the display unit 24 in accordance with an instruction by the operator (Step S1401).

The X-ray diagnosis apparatus 100 then selects a voxel V having a pixel value within a certain range from the region-of-interest coordinates (Step S1402). For example, the display-image changing unit 22 acquires the three-dimensional blood-vessel image data from the image database 11, reads the region-of-interest coordinates from the memory 32, and then selects a voxel V having a pixel value within the range R preliminarily set by the operator. It is assumed in this example that the range R is, for example, 30 millimeters as a standard.

The X-ray diagnosis apparatus 100 then displays the voxel V in a color that is different from the color of the other voxels and has good visibility (Step S1403). For example, the display-image creating unit 23 displays the voxel V selected at Step S1402 in a color that is different from the color of the other voxels and has good visibility, onto the display unit 24.

Subsequently, the X-ray diagnosis apparatus 100 determines whether correction of the range R is received (Step S1404). For example, the display-image changing unit 22 receives a correction signal that designates a correction of the range R by using the user interface 6, such as a lever.

If the correction is received (Yes at Step S1404), the X-ray diagnosis apparatus 100 again corrects the range R in accordance with the received correction signal, reselects a voxel V (Step S1402), displays the reselected voxel V in a color that is different from the color of the other voxels and has good visibility, onto the display unit 24.

By contrast, if the correction is not received (No at Step S1404), the X-ray diagnosis apparatus 100 displays the voxel V in the color having good visibility as it is onto the display unit 24 (Step S1405).

Accordingly, visibility of a region of interest is improved and confirmation becomes easier, thereby bringing efficiency to manual operations, so that reduction in the manual operation time can be expected.

The first to sixth embodiments according to the present invention have been explained above. According to the embodiments, a display image in a two-dimensional space is virtually created from medical image data in a three-dimensional, region-of-interest coordinates are estimated based on information specified about the virtually created display image (hereinafter, "virtual radioscopic image"), and the devices are controlled by using the estimated region-of-interest coordinates.

For example, according to the first embodiment, when receiving designation of an imaging position from a certain direction (for example, the press of the confirmation button indicating determination of the angle and the position of observation), a central axis line (a line connecting the focus point of the X-ray generating tube 7a and the iso center) is specified from a virtual radioscopic image that has been created when receiving the designation of the imaging position, and it is estimated that region-of-interest coordinates are the midpoint of a section having a pixel value in a certain range on the central axis line in medical image data in a three-dimensional space.

Regarding this point, according to a seventh embodiment of the present invention, a method of estimating region-of-interest coordinates (estimation by the region-of-interest coordinate estimating unit 30) is different from the above embodiments. Specifically, although the X-ray diagnosis apparatus 100 according to the seventh embodiment creates a virtual radioscopic image from medical image data in a three-dimensional space similarly to the above embodiments, the X-ray diagnosis apparatus 100 receives designation of imaging positions from at least two different directions. The X-ray diagnosis apparatus 100 then estimates region-of-interest coordinates based on the designation of the imaging positions of the at-least-two received directions. For example, the X-ray diagnosis apparatus 100 specifies at least two central axis lines from at least two virtual radioscopic images that have been created when receiving designation of imaging positions, and estimates region-of-interest coordinates based on the at-least-two specified central axis lines.

At first, a process procedure by the X-ray diagnosis apparatus 100 according to the seventh embodiment is explained below with reference to FIG. 20. FIG. 20 is a flowchart of a process procedure by the X-ray diagnosis apparatus 100 according to the seventh embodiment. The process procedure by the X-ray diagnosis apparatus 100 according to the seventh embodiment is not necessarily clearly divided into "a process procedure during an examination" and "a process procedure during a treatment". In other words, according to the seventh embodiment, designation of imaging positions is received from at least two different directions. For this reason, even though the first time designation is received in "the process procedure during an examination", in which of "the process procedure during an examination" and "the process procedure during a treatment" the second time and later designation is received vary depending on a concrete case. Although it is assumed in the following description a case where it is preliminarily set so as to estimate region-of-interest coordinates when receiving designation of imaging positions from three directions, and all of the three times of the designation are received in "the process procedure during an examination", the present invention is not limited to this.

As shown in FIG. 20, at first, similarly to the second embodiment, the X-ray diagnosis apparatus 100 rotationally images the head of the subject P, and acquires three-dimensional blood-vessel image data (Step S1501). Then, similarly to the second embodiment, the X-ray diagnosis apparatus 100 creates a virtual radioscopic image from the acquired three-dimensional blood-vessel image data, displays the created virtual radioscopic image onto the display unit (Step S1502).

Subsequently, the doctor moves the supporting device 9 and/or the couch 10 (Step S1503). For example, after checking a state of the shape and the position of an aneurysm, the doctor moves the supporting device 9 and/or the couch 10 by using the operation unit 1 such that a region of interest comes to the center of the field of view (the center of the image reception area).

Similarly to the first embodiment, the X-ray diagnosis apparatus 100 then changes the display of the virtual radioscopic image (Step S1504). In other words, the X-ray diagnosis apparatus 100 virtually creates three-dimensional blood-vessel image data in accordance with operation by the doctor, then creates a virtual radioscopic image in a two-dimensional space from the virtually created three-dimensional blood-vessel image data, and displays it onto the display unit 24.

After accordingly determining the angle and the position of observation, the doctor presses the confirmation button included in the operation unit 1 (Step S1505). The press of the confirmation button at this moment means that the X-ray diagnosis apparatus 100 according to the seventh embodiment receives designation of an imaging position with respect to one direction.

Consequently, the X-ray diagnosis apparatus 100 calculates a central axis line from the virtual radioscopic image that has been created when receiving the designation of the imaging position (Step S1506). For example, the X-ray diagnosis apparatus 100 acquires current state information about the supporting device 9 and other devices from the mechanism-state monitoring unit 4, and calculates a central axis line.

According to the seventh embodiment, the X-ray diagnosis apparatus 100 does not estimates region-of-interest coordinates at this stage, and continuously waits designation of an imaging position. Specifically, the X-ray diagnosis apparatus 100 determines whether designation of imaging positions has been received from three directions (Step S1507), if it has not been fully received yet (No at Step S1507), the process control goes back to Step S1503.

In other words, the doctor moves again the supporting device 9 and/or the couch 10 during the examination or the treatment (Step S1503). The X-ray diagnosis apparatus 100 then changes the display of the virtual radioscopic image (Step S1504), and after determining the angle and the position of observation, the doctor presses the confirmation button included in the operation unit 1 (Step S1505). The press of the confirmation button this time means that the X-ray diagnosis apparatus 100 according to the seventh embodiment receives designation of an imaging position with respect to a second direction. The X-ray diagnosis apparatus 100 then calculates a central axis line with respect to the second direction, from a virtual radioscopic image that has been created when receiving the designation of the imaging position (Step S1506).

In this way, until designation of imaging positions from three directions has been received, the X-ray diagnosis apparatus 100 repeats Steps S1503 to S1506, receives designation of imaging positions from three different directions, and calculates three central axis lines from three virtual radioscopic images.

Figure 21:
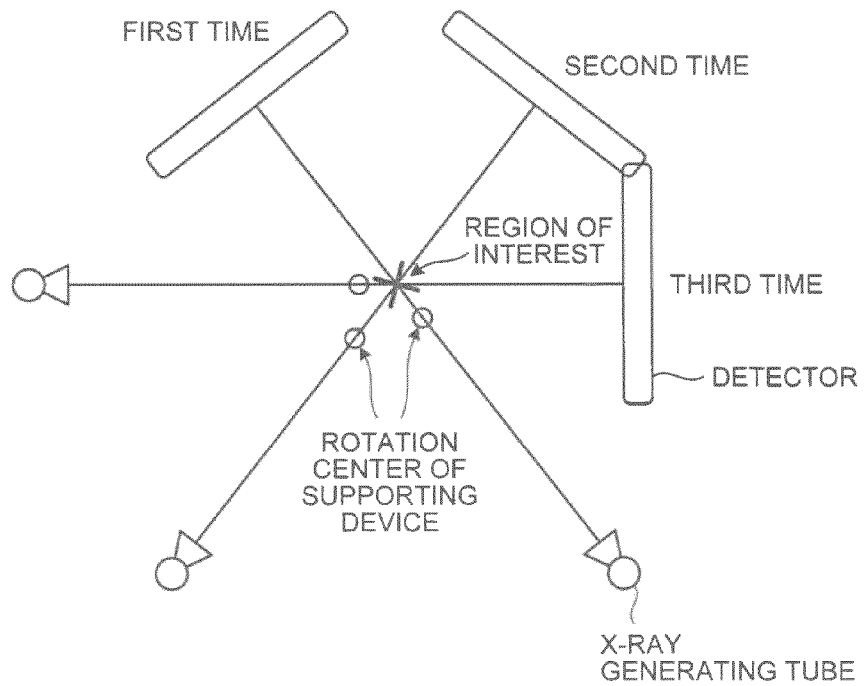
FIG. 21 is a schematic diagram for explaining an estimation of region-of-interest coordinates according to the seventh embodiment.
Figure 22:
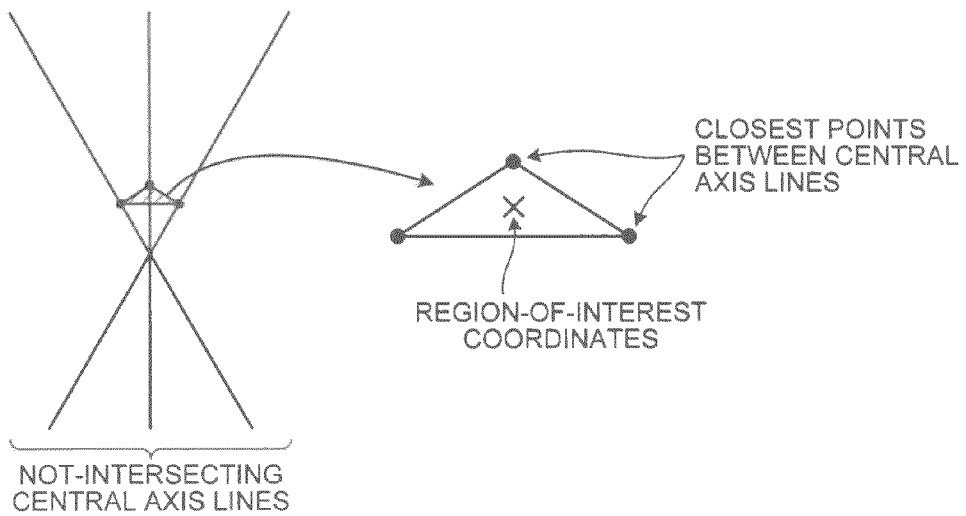
FIG. 22 is a schematic diagram for explaining an estimation of region-of-interest coordinates according to the seventh embodiment.

Subsequently, when the designation of imaging positions with respect to three directions is completed (Step S1507), the X-ray diagnosis apparatus 100 estimates region-of-interest coordinates based on the calculated three central axis lines (Step S1508), and stores the region-of-interest coordinates (Step S1509). An estimation of region-of-interest coordinates according to the seventh embodiment is explained below with reference to FIGS. 21 and 22. FIGS. 21 and 22 are schematic diagrams for explaining an estimation of region-of-interest coordinates according to the seventh embodiment.

As shown in FIG. 21, the iso center (the rotation center of the supporting device 9) is present on the central axis line connecting the center of the image reception area of the plane detector 8 and the focus point of the X-ray generating tube 7a. In other words, the central axis line is a line that connects the focus point of the X-ray generating tube 7a and the iso center. Moreover, FIG. 21 depicts respective central axis lines when the supporting device 9 and/or the couch 10 is moved three times such that the region of interest comes to the center of the field of view.

Because the doctor moves the supporting device 9 and/or the couch 10 such that the region of interest comes to the center of the field of view, the region of interest is supposed to be positioned at a substantial center of the created virtual radioscopic image. However, the virtual radioscopic image is an image in a two-dimensional space. Therefore, it is difficult to match up the region of interest with the iso center even by such operation by the doctor. In other words, as long as the region of interest matches the iso center, the region of interest is constantly located in the center of the field of view even if the imaging direction is changed; however, in many cases, the region of interest often do not match the iso center, consequently, when the imaging direction is changed, the region of interest is dislocated from the field of view. As a result of dislocation of the region of interest from the field of view, the doctor moves the supporting device 9 and/or the couch 10 again such that the region of interest comes to the center of the field of view.

Because the rotation axes of three orthogonal axes of the supporting device 9 are provided so as to intersect at the iso center, the position of the iso center is supposed to match up constantly (the iso center is a fixed point) even if the imaging direction is changed by rotating the supporting device 9. However, the position of the iso center is moved in FIG. 21. This is explained below. When the doctor moves the supporting device 9 and/or the couch 10, relative positional relation between the supporting device 9 and the couch 10 is changed. For this reason, when the coordinates of the supporting device 9 is calculated based on the coordinate system of the couch 10, the coordinates of the supporting device 9 are changed along with movement of the couch 10, as a result, the position of the iso center is also moved. The coordinate system of the couch 10 is the coordinate system of the subject P, which is the coordinate system of the region of interest. Therefore, FIG. 21 depicts such that while the position of the iso center is moved, the position of the region of interest is fixed.

According to the seventh embodiment, region-of-interest coordinates are estimated based on at least two calculated central axis lines (three central axis lines in FIG. 21) by using an assumption that the region of interest is supposed to be present at least on the central axis line. For example, when central axis lines do not intersect each other, as shown in FIG. 22, the X-ray diagnosis apparatus 100 obtains respective points on the both central axis lines at which the central axis lines approach each other most closely (points at which a distance between the central axis lines is the shortest), and uses a midpoint on a line connecting the obtained points (an area in a case of three or more central axis lines) for estimation of region-of-interest coordinates. For example, according to an example shown in FIG. 22, because any of the three central axis lines intersects none of the others, the center point in the area is estimated as region-of-interest coordinates.

When the central axis lines intersect each other, the X-ray diagnosis apparatus 100 uses an intersection point for estimation of region-of-interest coordinates. For example, suppose two central axis lines among three central axis lines intersect each other, and the rest one of the central axis lines does not intersects either of the two central axis lines. In such case, a point closest to the intersection point is specified on the rest one of the central axis lines, and a midpoint on a line connecting the specified point and the intersection point is estimated as region-of-interest coordinates. The central axis lines here are lines calculated from the coordinate system of the couch 10, as described above.

The present invention is not limited to the process procedure explained above with reference to FIG. 20. For example, the calculation processing of a central axis line performed at Step S1506 can be aggregately performed after designation of the imaging positions in three directions is completed. Alternatively, for example, designation of imaging positions of the second time and later can be designation of an imaging position by using an actual radioscopic image instead of designation of an imaging position by using a virtual radioscopic image.

As described above, the X-ray diagnosis apparatus 100 according to the seventh embodiment receives designation of imaging positions from at least two different directions. Moreover, the X-ray diagnosis apparatus 100 calculates at least two central axis lines, and estimates region-of-interest coordinates based on the at-least-two calculated central axis lines.

The designation of an imaging position is a natural manual operation, for example, for a doctor, to carry out through a usual work flow. For this reason, according to the seventh embodiment, the doctor can acquire information required for estimation of region-of-interest coordinates, for example, only by simply carrying out a usual work flow, thereby being able to improve operation efficiency. In other words, the doctor does not need to perform a special operation, for example, input of information required for estimation of region-of-interest coordinates into an image displayed on a dedicated work station. As a result, for example, even when an intervention treatment is performed by one doctor, the doctor can cope with it. Moreover, estimation of region-of-interest coordinates is performed based on at least two central axis lines. For this reason, according to the seventh embodiment, estimation of region-of-interest coordinates can be precisely performed.

The X-ray diagnosis apparatus 100 according to an eighth embodiment of the present invention is explained below. Similarly to the seventh embodiment, the X-ray diagnosis apparatus 100 according to the eighth embodiment receives designation of imaging positions from at least two different directions, and estimates region-of-interest coordinates based on at least two central axis lines. However, the X-ray diagnosis apparatus 100 according to the eighth embodiment is different in a point that after region-of-interest coordinates are once estimated, while a treatment is being performed by using an actual radioscopic image instead of a virtual radioscopic image, and when designation of an imaging position is received from the same direction, the values of the region-of-interest coordinates are renewed based on the newest central axis line.

For example, according to a coil embolization that is an intervention treatment for a head aneurysm, it is assumed that a virtual radioscopic image is to be created from preliminarily acquired three-dimensional blood-vessel image data, and the three-dimensional blood-vessel image data is data acquired in a state that a catheter or any other tool is not inserted (or a state in the origin of a blood vessel). On the other hand, for example, if a catheter is inserted to the vicinity of an aneurysm, a force of curving along the blood vessel and a force of trying to recover is produced on the catheter, thereby deforming the blood vessel such that a curve of the blood vessel becomes smaller. Consequently, not only the position of the blood vessel, but also the position of the aneurysm is to be dislocated from a position at the time of acquisition of the three-dimensional blood-vessel image data.

Therefore, after region-of-interest coordinates are once estimated, while a treatment is being performed by using an actual radioscopic image instead of a virtual radioscopic image; for example, when the doctor presses the confirmation button, the X-ray diagnosis apparatus 100 according to the eighth embodiment determines whether it is a case of receiving designation of the imaging position from the same direction. For example, the X-ray diagnosis apparatus 100 stores current state information about the supporting device 9 and other devices used for estimation of region-of-interest coordinates, and determines whether it is a case that designation of the imaging position from the same direction (such as the observation angle) is received, by comparing the stored current state information and current state information about the supporting device 9 and other devices actually acquired from the mechanism-state monitoring unit 4.

If it is determined that it is the case that designation of the imaging position from the same direction (such as the observation angle) is received, the X-ray diagnosis apparatus 100 calculates a central axis line by using the current state information about the supporting device 9 and other devices actually acquired from the mechanism-state monitoring unit 4. Subsequently, the X-ray diagnosis apparatus 100 again estimates region-of-interest coordinates based on the calculated central axis and the already calculated central axis with respect to other directions. At that time, because the central axis line with respect to a certain direction has been renewed, also estimated region-of-interest coordinates are supposed to be different values. Therefore, the X-ray diagnosis apparatus 100 renews the values of region-of-interest coordinates by storing the newly estimated values of the region-of-interest coordinates into a storage unit.

Although the embodiments according to the present invention have been explained above, the present invention can be implemented to various different forms in addition to the above embodiments.

According to the first to eighth embodiments described above, it is assumed that a medical image is three-dimensional blood-vessel image data; however, the present invention is not limited to this, neither limited to three-dimensional image data, nor limited to blood-vessel image data. As long as it is medical image data of rendering a region of interest, the present invention can be similarly applied to two-dimensional image data.

The above description has explained the first to sixth embodiments, and the seventh and eighth embodiments of the present invention, and those embodiments can be combined. For example, when the doctor moves the supporting device 9 and/or the couch 10 during an examination for the first time, by using the method according to the second embodiment, the X-ray diagnosis apparatus 100 estimates region-of-interest coordinates based on information that is specified with respect to a virtual radioscopic image, and controls the devices by using the estimated region-of-interest coordinates. If, for example, the aneurysm is moved after that, and consequently if the region of interest is dislocated from the field of view even though the devices are controlled; the doctor needs to move the supporting device 9 and/or the couch 10 again. In such case, by using the method according to the seventh embodiment, the X-ray diagnosis apparatus 100 receives designation of imaging positions from at least two different directions, and estimates region-of-interest coordinates based on at least two central axis lines.

In this way, for example, even when receiving designation of an imaging position for the first time, the X-ray diagnosis apparatus 100 estimates region-of-interest coordinates, and controls the devices based on the estimated region-of-interest coordinates. Moreover, when detecting that the supporting device 9 and/or the couch 10 is operated again by the operator, the X-ray diagnosis apparatus 100 calculates in turn at least two central axis lines, and estimates region-of-interest coordinates based on the at-least-two calculated central axis lines. The X-ray diagnosis apparatus 100 needs to store information required for estimation of region-of-interest coordinates into a storage unit as required.

Furthermore, the X-ray diagnosis apparatus 100 can be configured to control the second supporting device of the bi plane type by calculating an amount of control to be used for initial setting of the second supporting device after estimating region-of-interest coordinates by using the method according to the seventh embodiment. Moreover, the X-ray diagnosis apparatus 100 can be configured to control the X-ray beam-limiting device by calculating an amount of control to be used for control of the X-ray beam-limiting device after estimating region-of-interest coordinates by using the method according to the seventh embodiment. Furthermore, the X-ray diagnosis apparatus 100 can be configured to control the display device that displays a medical image by calculating an amount of control to be used for control of the display device after estimating region-of-interest coordinates by using the method according to the seventh embodiment.

Among the processes explained above in the first to eighth embodiments, the processes explained assuming to be automatically performed can be manually performed in all or part, or the processes explained assuming to be manually performed can be automatically performed in all or part by a known method. Information including the process procedures, the specific names, the various data and parameters shown in the above description and the drawings can be arbitrarily changed unless otherwise specified.

The components of each device shown in the drawings are conceptual for describing functions, and not necessarily to be physically configured as shown in the drawings. In other words, concrete forms of distribution and integration of the units are not limited to those shown in the drawings (for example, FIG. 2), and all or part of the units can be configured to be functionally or physically distributed and integrated in arbitrary units depending on various loads and conditions of the use. All or arbitrary part of the processing functions performed by the respective units are implemented by a Central Processing Unit (CPU) and computer programs that are analyzed and executed by the CPU, or can be implemented as hardware by wired logic.

As described above, the X-ray diagnosis apparatus according to the embodiments of the present invention is useful for controlling equipment, and particularly suitable for improving operation efficiency.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray diagnosis apparatus comprising:
a display-image creating unit that creates a display image from three-dimensional medical image data such that the display image of the three-dimensional medical image data substantially matches up with an anatomical structure on an acquired image by the X-ray diagnosis apparatus;
a display-image changing unit that changes a display image so as to maintain consistency of an anatomical structure in accordance with change in an acquiring condition by the X-ray diagnosis apparatus;
a display unit that displays a display image that is at least one of created and changed by at least one of the display-image creating unit and the display-image changing unit;
a region-of-interest coordinate estimating unit that estimates a position of a region of interest as region-of-interest coordinates based on pixel information about three-dimensional medical image data present on a line connecting a focus point of an X-ray generating tube and a substantial center of a detector surface;
an amount-of-control calculating unit that calculates an amount of control to be used for control of a certain device by using region-of-interest coordinates estimated by the region-of-interest coordinate estimating unit; and
a control unit that controls the certain device in accordance with the amount of control calculated by the amount-of-control calculating unit.

2. The X-ray diagnosis apparatus according to claim 1, wherein the acquiring condition is one of or a combination of an angle of a supporting device, a position of the supporting device, a scale of image enlargement, a position of a couch, a height of the couch, an X-ray beam-limiting device, and a compensating filter.

3. The X-ray diagnosis apparatus according to claim 1, wherein at least one of the display-image creating unit and the display-image changing unit at least one of creates and changes a display image not to display a region that is made invisible by an X-ray beam-limiting device.

4. The X-ray diagnosis apparatus according to claim 1, wherein at least one of the display-image creating unit and the display-image changing unit at least one of creates and changes a display image so as to change at least one of a color, a pattern, and a brightness of a region onto which all or part of X-rays are blocked by at least one of an X-ray beam-limiting device and a compensating filter.

5. The X-ray diagnosis apparatus according to claim 1, wherein the region-of-interest coordinate estimating unit displays on a display unit a pixel in a region within a certain range from estimated region-of-interest coordinates and each having a pixel value in a certain range, with at least one of a color, a pattern, and a brightness different from those of other pixels.

6. The X-ray diagnosis apparatus according to claim 1, wherein the region-of-interest coordinate estimating unit estimates the region-of-interest coordinates by calculating a center point of an aggregation of pixels continuously present on the line as an aggregation of pixels each having a pixel value in a certain range.

7. The X-ray diagnosis apparatus according to claim 6, wherein when no aggregation of pixels each having a pixel value in a certain range is present on the line, the region-of-interest coordinate estimating unit estimates the region-of-interest coordinates by calculating a center point of an aggregation of pixels present within a certain distance range from the line that is an aggregation of pixels each having a pixel value in a certain range.

8. The X-ray diagnosis apparatus according to claim 6, wherein
the region-of-interest coordinate estimating unit estimates the region-of-interest coordinates by calculating a center point of an aggregation of pixels continuously present on the line as an aggregation of pixels each having a pixel value in a certain range, and
the amount-of-control calculating unit calculates the amount of control such that an iso center is to be positioned at the center point.

9. The X-ray diagnosis apparatus according to claim 6, wherein when a plurality of aggregations of pixels each having a pixel value in a certain range is present on the line, the region-of-interest coordinate estimating unit calculates a length with respect to each of the aggregations of pixels, calculates a total volume of aggregations of pixels in the certain range that are aggregations of pixels present within a spherical region having a center at the center point and a radius that is a half of calculated length, calculates a value that calculated total volume is divided by a third power of the radius, and estimates region-of-interest coordinates based on each of the calculated values.

10. The X-ray diagnosis apparatus according to claim 6, wherein when a plurality of aggregations of pixels each having a pixel value in a certain range is present on the line, the region-of-interest coordinate estimating unit calculates a volume of a region sectioned with a pixel present within a certain range from the center point and having a pixel value in a certain range with respect to each center point, and estimates the region-of-interest coordinates based on a value of calculated volume.

11. The X-ray diagnosis apparatus according to claim 6, wherein when a plurality of aggregations of pixels each having a pixel value in a certain range is present on the line, the region-of-interest coordinate estimating unit calculates a distance between the center point and an end point on the line on a side of a detector with respect to each center point, and estimates the region-of-interest coordinates based on a value of calculated distance.

12. The X-ray diagnosis apparatus according to claim 6, further comprising a selection-instruction receiving unit that receives a selection instruction to select a certain center point from among a plurality of center points when a plurality of aggregations of pixels each having a pixel value in a certain range is present on the line.

13. The X-ray diagnosis apparatus according to claim 6, further comprising a selection-instruction receiving unit that receives a selection instruction to select one from among information displayed in a differentiated manner by the region-of-interest coordinate estimating unit, wherein when a plurality of aggregations of pixels each having a pixel value in a certain range is present on the line, the region-of-interest coordinate estimating unit displays a region within a certain range from among the aggregations in a differentiated manner with at least one of a color, a pattern, and a brightness different from those of other aggregations.

14. The X-ray diagnosis apparatus according to claim 1, wherein when a plurality of aggregations of pixels each having a pixel value in a certain range is present on the line, the region-of-interest coordinate estimating unit estimates the region-of-interest coordinates based on one of two sets of information, namely, a set of information about each of the aggregations of pixels present on the line, and a set of information about each of aggregations of pixels further including pixels present in a vicinity of each of the aggregations of pixels present on the line.

15. The X-ray diagnosis apparatus according to claim 1, wherein when a plurality of aggregations of pixels each having a pixel value in a certain range is present on the line, the region-of-interest coordinate estimating unit calculates respective lengths of the aggregations of pixels, and estimates the region-of-interest coordinates based on respective calculated lengths.

16. The X-ray diagnosis apparatus according to claim 1, wherein
the amount-of-control calculating unit calculates an amount of control to be used for control of at least one of a supporting device, a couch, a reading-region of an X-ray detector, an X-ray beam-limiting device, and a compensating filter, as the certain device, and
the control unit controls at least one of the supporting device, the couch, the reading-region of the X-ray detector, the X-ray beam-limiting device, and the compensating filter, in accordance with the amount of control calculated by the amount-of-control calculating unit.

17. The X-ray diagnosis apparatus according to claim 1, wherein
the X-ray diagnosis apparatus is a bi plane type,
the amount-of-control calculating unit calculates an amount of control to be applied to a second supporting device as the certain device based on the region-of-interest coordinates estimated by the region-of-interest coordinate estimating unit, and
the control unit controls the second supporting device in accordance with the amount of control calculated by the amount-of-control calculating unit.

18. The X-ray diagnosis apparatus according to claim 1, wherein
the amount-of-control calculating unit calculates an amount of control to be used for control of at least one of an X-ray beam-limiting device and a compensating filter as the certain device, and
the control unit controls at least one of the X-ray beam-limiting device and the compensating filter, in accordance with the amount of control calculated by the amount-of-control calculating unit.

19. The X-ray diagnosis apparatus according to claim 18, wherein
the amount-of-control calculating unit identifies a point on an X-ray detector that anatomically matches up with the region-of-interest coordinates, and
the control unit controls at least one of the X-ray beam-limiting device and the compensating filter so as to vary X-ray incident strengths in a region within a certain range from identified point and other regions.

20. The X-ray diagnosis apparatus according to claim 19, wherein the certain range is one of a predetermined value and a range in which an X-ray strength distribution used in advance is to be reproduced.

21. The X-ray diagnosis apparatus according to claim 1, wherein at least one the display-image creating unit and the display-image changing unit extracts a region within a certain range from the region-of-interest coordinates estimated by the region-of-interest coordinate estimating unit, from the three-dimensional medical image data, and at least one of creates and changes a display image by using only extracted region.

22. The X-ray diagnosis apparatus according to claim 1, further comprising:
- a region-of-interest coordinate estimating unit that identifies a line connecting a focus point of an X-ray generating tube and a substantial center of a detector surface with respect to at least two different directions, and estimates positional coordinates that is closest to identified line as region-of-interest coordinates,
- an amount-of-control calculating unit that calculates an amount of control to be used for control of a certain device by using the region-of-interest coordinates estimated by the region-of-interest coordinate estimating unit; and
- a control unit that controls the certain device in accordance with the amount of control calculated by the amount-of-control calculating unit.

23. The X-ray diagnosis apparatus according to claim 22, wherein when designation of an imaging position is performed by using at least one of a radioscopic image actually taken from a subject, and an image displayed on a display unit by at least one of the display-image creating unit and the display-image changing unit, and is in a same direction as a direction of an observation position already used for estimation by the region-of-interest coordinate estimating unit, the region-of-interest coordinate estimating unit newly identifies a line that connects a focus point of the X-ray generating tube and a substantial center of the detector surface based on the designation of the imaging position, and newly estimates the region-of-interest coordinates based on identified new line and a line that is already specified with respect to another direction.

* * * * *